United States Patent
Kalkan et al.

(10) Patent No.: US 12,410,406 B2
(45) Date of Patent: Sep. 9, 2025

(54) METHOD OF GENERATING HEPATIC CELLS

(71) Applicant: Bit Bio Limited, Cambridge (GB)

(72) Inventors: Tüzer Kalkan, Cambridge (GB); Thomas Pierre Michel Moreau, Cambridge (GB); Carl Ward, Birmingham (GB); Tildon Grant Belgard, Niceville, FL (US); Fabian Bachinger, Cambridge (GB)

(73) Assignee: Bit Bio Limited, Cambridge (GB)

( * ) Notice: Subject to any disclaimer, the term of this patent is extended or adjusted under 35 U.S.C. 154(b) by 525 days.

(21) Appl. No.: 17/666,334

(22) Filed: Feb. 7, 2022

(65) Prior Publication Data
US 2022/0235321 A1 Jul. 28, 2022

Related U.S. Application Data

(60) Division of application No. 17/206,451, filed on Mar. 19, 2021, now Pat. No. 11,274,279, which is a continuation of application No. PCT/GB2021/050622, filed on Mar. 11, 2021.

(60) Provisional application No. 62/988,349, filed on Mar. 11, 2020.

(51) Int. Cl.
*C12N 5/071* (2010.01)
*A61K 35/407* (2015.01)
*C12N 5/074* (2010.01)
*C12N 5/10* (2006.01)
*C12Q 1/02* (2006.01)

(52) U.S. Cl.
CPC ............ *C12N 5/067* (2013.01); *A61K 35/407* (2013.01); *C12N 5/0696* (2013.01); *C12N 5/10* (2013.01); *C12Q 1/025* (2013.01); *C12N 2501/60* (2013.01); *C12N 2506/02* (2013.01); *C12N 2506/03* (2013.01); *C12N 2506/45* (2013.01)

(58) Field of Classification Search
CPC ........ C12N 5/067; C12N 5/0696; C12N 5/10; A61K 35/407
USPC ..................................................... 424/93.21
See application file for complete search history.

(56) References Cited

U.S. PATENT DOCUMENTS

| | | |
|---|---|---|
| 5,837,234 A | 11/1998 | Gentile et al. |
| 6,582,955 B2 | 6/2003 | Martinez et al. |
| 7,473,555 B2 | 1/2009 | Mandalam et al. |
| 7,824,912 B2 | 11/2010 | Sherley et al. |
| 8,148,151 B2 | 4/2012 | Zhao et al. |
| 8,481,317 B2 | 7/2013 | Yu et al. |
| 8,802,432 B2 | 8/2014 | Zaret et al. |
| 8,835,163 B2 | 9/2014 | Zhao et al. |
| 9,057,051 B2 | 6/2015 | Pauwelyn et al. |
| 9,181,529 B2 | 11/2015 | Kattman et al. |
| 9,213,999 B2 | 12/2015 | Sakurada |
| 9,260,722 B2 | 2/2016 | Yu et al. |
| 9,334,479 B2 | 5/2016 | Herrera Sanchez et al. |
| 9,394,522 B2 | 7/2016 | Brolen et al. |
| 9,402,944 B2 | 8/2016 | Selden et al. |
| 9,555,061 B2 | 1/2017 | Shiota et al. |
| 9,623,048 B2 | 4/2017 | Hui et al. |
| 9,677,085 B2 | 6/2017 | Guye et al. |
| 9,845,458 B2 | 12/2017 | Matsuyama et al. |
| 10,000,739 B2 | 6/2018 | Kume et al. |
| 10,004,767 B2 | 6/2018 | Peltz et al. |
| 10,072,242 B2 | 9/2018 | Kanemura et al. |
| 10,072,248 B2 | 9/2018 | Lee et al. |
| 10,081,609 B2 | 9/2018 | Bhatia et al. |
| 10,093,903 B2 | 10/2018 | Kannemeier et al. |
| 10,100,284 B2 | 10/2018 | Tanaka et al. |
| 10,266,806 B2 | 4/2019 | Khetani et al. |
| 10,294,457 B2 | 5/2019 | Kuppers-Munther et al. |
| 10,323,228 B2 | 6/2019 | Yu et al. |
| 10,370,638 B2 | 8/2019 | Takebe et al. |
| 10,443,071 B2 | 10/2019 | Tomizawa |
| 10,513,685 B2 | 12/2019 | Itchoda et al. |
| 10,590,389 B2 | 3/2020 | Kamei et al. |
| 10,688,221 B2 | 6/2020 | Mazza et al. |
| 10,711,249 B2 | 7/2020 | Osafune et al. |
| 2011/0086379 A1 | 4/2011 | Blak et al. |
| 2013/0212722 A1 | 8/2013 | West |
| 2014/0087416 A1 | 3/2014 | Simeonov et al. |
| 2017/0107486 A1 | 4/2017 | Yu et al. |
| 2017/0218333 A1 | 8/2017 | Deng et al. |
| 2017/0304369 A1 | 10/2017 | Ang et al. |
| 2018/0072988 A1 | 3/2018 | Sun et al. |
| 2018/0085407 A1 | 3/2018 | Stolen et al. |
| 2018/0127714 A1 | 5/2018 | Ko |
| 2018/0135023 A1 | 5/2018 | Wang et al. |
| 2018/0251735 A1 | 9/2018 | Ko |
| 2018/0320186 A1 | 11/2018 | Kanemaki et al. |
| 2019/0010490 A1 | 1/2019 | Cowan et al. |
| 2019/0048320 A1 | 2/2019 | Ko |

(Continued)

FOREIGN PATENT DOCUMENTS

| | | |
|---|---|---|
| EP | 1516924 A1 | 3/2005 |
| EP | 1516925 A1 | 3/2005 |

(Continued)

OTHER PUBLICATIONS

Aizarani et al. "A human liver cell atlas reveals heterogeneity and epithelial progenitors," Nature, 2019, 572(7768):199-204.

(Continued)

*Primary Examiner* — Valarie E Bertoglio
(74) *Attorney, Agent, or Firm* — Goodwin Procter LLP

(57) ABSTRACT

The invention relates to methods of generating hepatic cells by overexpressing combinations of transcription factors, in particular for use in cellular reprogramming methods.

12 Claims, 29 Drawing Sheets

(56) References Cited

U.S. PATENT DOCUMENTS

| | | |
|---|---|---|
| 2019/0071314 A1 | 3/2019 | Min et al. |
| 2019/0076551 A1 | 3/2019 | Bogorad et al. |
| 2019/0112353 A1 | 4/2019 | Yang et al. |
| 2019/0185903 A1 | 6/2019 | Dezawa |
| 2019/0298775 A1 | 10/2019 | Takebe et al. |
| 2020/0140821 A1 | 5/2020 | Elfenbein et al. |
| 2020/0199528 A1 | 6/2020 | Boon et al. |
| 2020/0199537 A1 | 6/2020 | Takebe et al. |
| 2020/0199538 A1 | 6/2020 | Ng et al. |

FOREIGN PATENT DOCUMENTS

| | | |
|---|---|---|
| EP | 1436381 B1 | 5/2005 |
| EP | 1414947 B1 | 9/2008 |
| EP | 1442115 B1 | 8/2009 |
| EP | 1404816 B1 | 2/2010 |
| EP | 1888742 B1 | 10/2010 |
| EP | 1438418 B1 | 11/2010 |
| EP | 1692275 B1 | 12/2010 |
| EP | 1711597 B1 | 3/2012 |
| EP | 1697500 B1 | 3/2013 |
| EP | 1491093 B1 | 7/2013 |
| EP | 2155860 B1 | 8/2014 |
| EP | 1644486 B1 | 9/2014 |
| EP | 1969118 B2 | 9/2014 |
| EP | 2169051 B1 | 2/2016 |
| EP | 2374871 B1 | 4/2016 |
| EP | 2550355 B1 | 11/2016 |
| EP | 2024492 B1 | 3/2017 |
| EP | 2367931 B1 | 5/2017 |
| EP | 2970178 B1 | 6/2017 |
| EP | 2601289 B1 | 7/2017 |
| EP | 2699593 B1 | 8/2017 |
| EP | 2588592 B1 | 9/2017 |
| EP | 2609192 B1 | 12/2017 |
| EP | 2698365 B1 | 12/2017 |
| EP | 2281875 B1 | 3/2018 |
| EP | 1970068 B1 | 4/2018 |
| EP | 2836591 B1 | 6/2018 |
| EP | 2644694 B1 | 7/2018 |
| EP | 2206778 B1 | 8/2018 |
| EP | 2956538 B1 | 11/2018 |
| EP | 2421954 B1 | 12/2018 |
| EP | 2980207 B1 | 12/2018 |
| EP | 2495320 B1 | 2/2019 |
| EP | 2356213 B1 | 5/2019 |
| EP | 2598633 B1 | 5/2019 |
| EP | 3097186 B1 | 5/2019 |
| EP | 3151875 B1 | 8/2019 |
| EP | 3046628 B1 | 11/2019 |
| EP | 3088415 B1 | 11/2019 |
| EP | 3119879 B1 | 12/2019 |
| EP | 2488631 B1 | 1/2020 |
| EP | 3064575 B1 | 2/2020 |
| EP | 3060652 B1 | 3/2020 |
| EP | 3365429 B1 | 3/2020 |
| EP | 3272855 B1 | 4/2020 |
| EP | 3366687 B1 | 4/2020 |
| EP | 3702444 A1 | 9/2020 |
| KR | 101535070 B1 | 7/2015 |
| WO | 2001/019182 A1 | 3/2001 |
| WO | 2001/059076 A2 | 8/2001 |
| WO | 2002/073188 A1 | 9/2002 |
| WO | 2003/089631 A1 | 10/2003 |
| WO | 2004/007683 A2 | 1/2004 |
| WO | 2004/046310 A2 | 6/2004 |
| WO | 2005/026332 A1 | 3/2005 |
| WO | 2005/040391 A1 | 5/2005 |
| WO | 2005/097980 A2 | 10/2005 |
| WO | 2005/118779 A1 | 12/2005 |
| WO | 2006/083133 A2 | 8/2006 |
| WO | 2006/131543 A1 | 12/2006 |
| WO | 2007/014275 A2 | 2/2007 |
| WO | 2008/035169 A2 | 3/2008 |
| WO | 2008/060792 A2 | 5/2008 |
| WO | 2008/088863 A2 | 7/2008 |
| WO | 2009/080794 A1 | 7/2009 |
| WO | 2010/007031 A2 | 1/2010 |
| WO | 2010/109187 A1 | 9/2010 |
| WO | 2010/117464 A1 | 10/2010 |
| WO | 2010/130446 A1 | 11/2010 |
| WO | 2011/084747 A2 | 7/2011 |
| WO | 2011/119942 A1 | 9/2011 |
| WO | 2011/130402 A2 | 10/2011 |
| WO | 2012/005690 A1 | 1/2012 |
| WO | 2013/062140 A1 | 5/2013 |
| WO | 2013/068557 A1 | 5/2013 |
| WO | 2013/156954 A1 | 10/2013 |
| WO | 2013/190013 A1 | 12/2013 |
| WO | 2014/006228 A1 | 1/2014 |
| WO | 2014/053709 A1 | 4/2014 |
| WO | 2014/174047 A1 | 10/2014 |
| WO | 2015/073751 A1 | 5/2015 |
| WO | 2015/164228 A1 | 10/2015 |
| WO | 2016/163958 A1 | 10/2016 |
| WO | 2016/183041 A2 | 11/2016 |
| WO | 2017/093418 A1 | 6/2017 |
| WO | 2017/109757 A1 | 6/2017 |
| WO | 2017/117333 A1 | 7/2017 |
| WO | 2017/149025 A1 | 9/2017 |
| WO | 2017/179021 A1 | 10/2017 |
| WO | 2018/007871 A1 | 1/2018 |
| WO | 2018/096343 A1 | 5/2018 |
| WO | 2018/154380 A1 | 8/2018 |
| WO | 2019/055345 A1 | 3/2019 |
| WO | 2019/126626 A1 | 6/2019 |
| WO | 2019/177936 A1 | 9/2019 |
| WO | 2019/213366 A1 | 11/2019 |
| WO | 2019/222487 A1 | 11/2019 |
| WO | 2019/222853 A1 | 11/2019 |
| WO | 2019/237124 A1 | 12/2019 |
| WO | 2019/241705 A1 | 12/2019 |
| WO | 2020/056158 A1 | 3/2020 |
| WO | 2020/081716 A2 | 4/2020 |
| WO | 2020/139914 A1 | 7/2020 |

OTHER PUBLICATIONS

Ang et al. "A Roadmap for Human Liver Differentiation from Pluripotent Stem Cells," Cell Reports, 2018, 22(8):2190-2205.

Anonymous: "Introduction to Tet expression systems", eNews, Apr. 1, 2015 (Apr. 1, 2015), pp. 1-2, XP055713341, The Jackson Laboratory, Retrieved from the Internet: URL:https://www.jax.org/news-and-insights/2015/april/introduction-to-tetA-expression-systems#, 3 pages.

Anonymous: "Introduction to Tet expression systems", The Jackson Laboratory, Retrieved from the Internet: URL: https://https://www.jax.org/news-and-insights/2015/april/introduction-to-tet-expression-systems, accessed Sep. 5, 2020, 2 pages.

Banerjee et al. "Targeting xenobiotic receptors PXR and CAR in human diseases," In Drug Discovery Today, 2015, 20(5):618-628. Elsevier Ltd.

Becht et al. "Dimensionality reduction for visualizing single-cell data using UMAP," Nature Biotechnology, 2019, 37(1):38-47.

Bertero et al., "Optimized inducible shRNA and CRISPR/Cas9 platforms for in vitro studies of human development usinq hPSCs", Development, vol. 143, No. 23, pp. 4405-4418 (2016).

Bulutoglu et al. "A comparison of hepato-cellular in vitro platforms to study CYP3A4 induction, " Plos One, 2020, 15(2):e0229106, 17 pages.

Backman et al., "Generalized tetracycline induced Cre recombinase expression through the ROSA26 locus of recombinant mice." Journal of neuroscience methods 176, No. 1 (2009): 16-23.

Cerbini et al. "Transcription Activator-Like Effector Nuclease (TALEN)-Mediated CLYBL Targeting Enables Enhanced Transgene Expression and One-Step Generation of Dual Reporter Human Induced Pluripotent Stem Cell (PSC) and Neural Stem Cell (NSC) Lines," PLOS One, 2015, 10(1):e0116032.

Dekelver et al., "Functional genomics, proteomics, and regulatory DNA analysis in isogenic settings using zinc finger nuclease-driven

(56) References Cited

OTHER PUBLICATIONS transgenesis into a safe harbor locus in the human genome", Genome Research, vol. 20, No. 3, pp. 1133-1142 (2010).
EP 17807909.1-1118—Office Action, Sep. 21, 2020, 8 pages.
Golson et al. "Fox transcription factors: From development to disease," Development (Cambridge), 2016, 143(24):4558-4570.
Gossen et al. "Tight control of gene expression in mammalian cells by tetracycline-responsive promoters," Proc. Natl. Acad. Sci. U.S. A., 1992, 89(12):5547-51.
Haque et al. "A practical guide to single-cell RNA-sequencing for biomedical research and clinical applications," Genome Medicine, 2017, 9(75):1-12.
Iacovino et al., "Inducible cassette exchange: a rapid and efficient system enabling conditional gene expression in embryonic stem and primary cells." Stem cells 29, No. 10 (2011): 1580-1588.
Ansante et al. "Human hepatocyte transplantation for liver disease: current status and future perspectives," Pediatric Research, 2018, 83(1-2):232-240.
Wafuchi-Doi et al. "The Pioneer Transcription Factor FoxA Maintains an Accessible Nucleosome Configuration at Enhancers for Tissue-Specific Gene Activation," Molecular Cell, 2016, 62(1):79-91.
Kaestner et al. "Inactivation of the winged helix transcription factor HNF3? affects glucose homeostasis and islet glucagon gene expression in vivo," Genes and Development, 1999, 13(4):495-504.
Khan et al. "The role of mammalian Creb3-like transcription factors in response to nutrients," In Frontiers in Genetics, 2019, 10(591):1-9.
Kietzmann. "Metabolic zonation of the liver: The oxygen gradient revisited," Redox Biology, 2017, 11:622-630.
Lee et al. "Foxa2 is required for the differentiation of pancreatic ?-cells," Developmental Biology, 2005, 278(2):484-495.
Macparland et al. "Single cell RNA sequencing of human liver reveals distinct intrahepatic macrophage populations," Nature Communications, 2018, 9(1):4383, 21 pages.
Nishikawa et al. "Resetting the transcription factor network reverses terminal chronic hepatic failure," Journal of Clinical Investigation, 2015, 125(4):1533-44.
Papapetrou and Schambach, "Gene Insertion Into Genomic Safe Harbors for Human Gene Therapy", Molecular Therapy, vol. 24, No. 4, DD. 678-684 (2016).
Papapetrou et al. "Genomic safe harbors permit high beta-globin transgene expression in thalassemia induced pluripotent stem cells," Nature Biotechnology, 2011, 29(1):73-8.
Pawlowski et al., "Inducible and Deterministic Forward Programming of Human Pluripotent Stem Cells into Neurons, Skeletal Myocytes, and Oligodendrocytes", Stem Cell Reports, vol. 8, No. 4, pp. 803-812 (2017).
PCT/GB2017/053531—International Search Report, Mar. 26, 2018, 9 pages.
Pei et al., "A platform for rapid generation of single and multiplexed reporters in human iPSC lines." Scientific reports 6, No. 1 (2015): 1-10.
Petersen et al., "UW-Madison Human Stem Cell Gene Editing Service A Campus Resource For Applying CRISPR/Cas9in Human Pluripotent Stem Cells", University of Wisonsin. Retreived from the Internet: https://waisman. wiscweb.wisc.edu/wp-content/uploads/sites/69/2017/08/GeneEditingServiceSept2016.pdf (2016).
Popescu et al. "Decoding human fetal liver haematopoiesis," Nature, 2011, 574(7778):365-371.
Qian et al. "In vivo reprogramming of murine cardiac fibroblasts into induced cardiomyocytes," Nature, 2012, 485(7400):593-8.
Qian et al., "A simple and efficient system for regulating gene expression in human pluripotent stem cells and derivatives", Stem Cells, vol. 32, No. 5, DD. 1230-1238 (2014).
Ramachandra et al. "Efficient recombinase-mediated cassette exchange at the AAVS1 locus in human embryonic stem cells using baculoviral vectors." Nucleic acids research 39, No. 16 (2011): e107-e107, 13 pages.
Sadelain et al., "Safe harbours for the integration of new DNA in the human genome", Nature Rev. Cancer, vol. 12, No. 1, pp. 51-58 (2011).
Segal et al. "Single cell analysis of human fetal liver captures the transcriptional profile of hepatobiliary hybrid progenitors," Nature Communications, 2019, 10(1):3350, 14 pages.
Selden et al. "A clinical-scale BioArtificial Liver, developed for GMP, improved clinical parameters of liver function in borcine liver failure," Scientific Reports, 2017, 7(1):14518, 19 pages.
Shen et al. "Foxa3 (Hepatocyte Nuclear Factor 3?) is Required for the Regulation of Hepatic GLUT2 Expression and the Maintenance of Glucose Homeostasis during a Prolonged Fast," Journal of Biological Chemistry, 2001, 276 (46):42812-42817.
Swift et al. "Sandwich-cultured hepatocytes: An in vitro model to evaluate hepatobiliary transporter-based drug interactions and hepatotoxicity," Drug Metabolism Reviews, 2010, 42(3):446-471.
Wang et al. "A regulatory system for use in gene transfer," Proc. Natl. Acad. Sci. USA, 1994, 91(17):8180-8184.
Williams. "Application of hepatocyte-like cells to enhance hepatic safety risk assessment in drug discovery," Philosophical Transactions The Royal Society B Biological Sciences, 2018, 373(1750):20170228, 4 pages.
Xiang et al. "Long-term functional maintenance of primary human hepatocytes in vitro," Science, 2019, 364(6438):399-402.
Bochkis et al. "Genome-wide location analysis reveals distinct transcriptional circuitry by paralogous regulators Foxa1 and Foxa2," PLOS Genetics, 2012, 8(6):e1002770, 10 pages.
Wederell et al. "Global analysis of in vivo Foxa2-binding sites in mouse adult liver using massively parallel sequencing," Nucleic Acids Research, 2008, 36(14):4549-4564.
Pournasr et al. "Transcription factor-mediated reprograming of fibroblasts to hepatocyte-like cells," European Journal of Cell Biology, 2015, 94(2015):603-310.
Notification of Transmittal of the International Search Report and the Written Opinion of the International Searching Authority, or the Declaration, Int'l Application No. PCT/GB2021/050622, mailed Jun. 22, 2021, 12 pages.

E

| Bit Bio reprogrammed cells | iPSC |
|---|---|
| Day 2 | 18.42 |
| Day 7 ALB- | 32.25 |
| Day 7 ALB+ | 1.95 |
| Day 11 ALB-/CYP3A4- | 31.77 |
| Day 11 ALB+/CYP3A4- | 4.48 |
| Day 11 ALB+/CYP3A4+ | 1.07 |
| Day 10 ALB+/CYP3A4+ | 0.85 |

| non-Hepatocyte | Fetal Hepatocyte | Adult Hepatocyte |
|---|---|---|
| 73.58 | 7.23 | 0.76 |
| 22.63 | 23.30 | 0.02 |
| 1.69 | 72.50 | 1.77 |
| 62.23 | 5.89 | 0.14 |
| 50.28 | 40.71 | 4.52 |
| 9.93 | 75.59 | 13.41 |
| 7.67 | 69.41 | 22.08 |

(D) Table 5

| | Combination | % of cells with the combination |
|---|---|---|
| 0 | ('eTF007-CREB3L3', 'eTF008-FOXA1', 'eTF010-FOXA3', 'eTF011-GATA4') | 36 |
| 1 | ('eTF007-CREB3L3', 'eTF010-FOXA3', 'eTF011-GATA4', 'eTF092-KLF9') | 34 |
| 2 | ('eTF007-CREB3L3', 'eTF010-FOXA3', 'eTF011-GATA4', 'eTF033-HHEX') | 33 |
| 3 | ('eTF007-CREB3L3', 'eTF008-FOXA1', 'eTF011-GATA4', 'eTF092-KLF9') | 31 |
| 4 | ('eTF007-CREB3L3', 'eTF008-FOXA1', 'eTF010-FOXA3', 'eTF092-KLF9') | 31 |
| 5 | ('eTF007-CREB3L3', 'eTF008-FOXA1', 'eTF010-FOXA3', 'eTF033-HHEX') | 31 |
| 6 | ('eTF007-CREB3L3', 'eTF010-FOXA3', 'eTF011-GATA4', 'eTF018-NR1I2') | 31 |
| 7 | ('eTF007-CREB3L3', 'eTF008-FOXA1', 'eTF011-GATA4', 'eTF033-HHEX') | 30 |
| 8 | ('eTF007-CREB3L3', 'eTF008-FOXA1', 'eTF010-FOXA3', 'eTF018-NR1I2') | 29 |
| 9 | ('eTF007-CREB3L3', 'eTF010-FOXA3', 'eTF033-HHEX', 'eTF092-KLF9') | 29 |
| 10 | ('eTF007-CREB3L3', 'eTF008-FOXA1', 'eTF011-GATA4', 'eTF018-NR1I2') | 29 |
| 11 | ('eTF007-CREB3L3', 'eTF008-FOXA1', 'eTF033-HHEX', 'eTF092-KLF9') | 28 |
| 12 | ('eTF007-CREB3L3', 'eTF011-GATA4', 'eTF033-HHEX', 'eTF092-KLF9') | 28 |
| 13 | ('eTF008-FOXA1', 'eTF010-FOXA3', 'eTF011-GATA4', 'eTF092-KLF9') | 27 |
| 14 | ('eTF006-ATF5', 'eTF007-CREB3L3', 'eTF010-FOXA3', 'eTF011-GATA4') | 27 |
| 15 | ('eTF008-FOXA1', 'eTF010-FOXA3', 'eTF011-GATA4', 'eTF033-HHEX') | 27 |
| 16 | ('eTF007-CREB3L3', 'eTF011-GATA4', 'eTF018-NR1I2', 'eTF092-KLF9') | 26 |
| 17 | ('eTF007-CREB3L3', 'eTF010-FOXA3', 'eTF018-NR1I2', 'eTF092-KLF9') | 26 |
| 18 | ('eTF007-CREB3L3', 'eTF011-GATA4', 'eTF018-NR1I2', 'eTF033-HHEX') | 26 |
| 19 | ('eTF010-FOXA3', 'eTF011-GATA4', 'eTF033-HHEX', 'eTF092-KLF9') | 26 |
| 20 | ('eTF008-FOXA1', 'eTF010-FOXA3', 'eTF011-GATA4', 'eTF018-NR1I2') | 26 |
| 21 | ('eTF004-MLXIPL', 'eTF007-CREB3L3', 'eTF010-FOXA3', 'eTF011-GATA4') | 26 |
| 22 | ('eTF007-CREB3L3', 'eTF008-FOXA1', 'eTF018-NR1I2', 'eTF092-KLF9') | 25 |
| 23 | ('eTF006-ATF5', 'eTF007-CREB3L3', 'eTF011-GATA4', 'eTF092-KLF9') | 25 |
| 24 | ('eTF010-FOXA3', 'eTF011-GATA4', 'eTF018-NR1I2', 'eTF092-KLF9') | 25 |
| 25 | ('eTF006-ATF5', 'eTF007-CREB3L3', 'eTF008-FOXA1', 'eTF011-GATA4') | 25 |
| 26 | ('eTF007-CREB3L3', 'eTF010-FOXA3', 'eTF018-NR1I2', 'eTF033-HHEX') | 25 |
| 27 | ('eTF010-FOXA3', 'eTF011-GATA4', 'eTF018-NR1I2', 'eTF033-HHEX') | 25 |
| 28 | ('eTF007-CREB3L3', 'eTF008-FOXA1', 'eTF018-NR1I2', 'eTF033-HHEX') | 25 |
| 29 | ('eTF008-FOXA1', 'eTF011-GATA4', 'eTF033-HHEX', 'eTF092-KLF9') | 25 |
| 30 | ('eTF008-FOXA1', 'eTF010-FOXA3', 'eTF033-HHEX', 'eTF092-KLF9') | 24 |
| 31 | ('eTF006-ATF5', 'eTF007-CREB3L3', 'eTF008-FOXA1', 'eTF010-FOXA3') | 24 |
| 32 | ('eTF006-ATF5', 'eTF007-CREB3L3', 'eTF010-FOXA3', 'eTF092-KLF9') | 24 |
| 33 | ('eTF006-ATF5', 'eTF007-CREB3L3', 'eTF008-FOXA1', 'eTF092-KLF9') | 23 |
| 34 | ('eTF008-FOXA1', 'eTF010-FOXA3', 'eTF018-NR1I2', 'eTF092-KLF9') | 23 |
| 35 | ('eTF008-FOXA1', 'eTF011-GATA4', 'eTF018-NR1I2', 'eTF092-KLF9') | 23 |
| 36 | ('eTF004-MLXIPL', 'eTF007-CREB3L3', 'eTF008-FOXA1', 'eTF010-FOXA3') | 23 |
| 37 | ('eTF004-MLXIPL', 'eTF007-CREB3L3', 'eTF008-FOXA1', 'eTF011-GATA4') | 23 |
| 38 | ('eTF006-ATF5', 'eTF010-FOXA3', 'eTF011-GATA4', 'eTF092-KLF9') | 23 |

FIGURE 12 (continued)

(D) Table 5 (continued)

| | Combination | % of cells with the combination |
|---|---|---|
| 39 | ('eTF007-CREB3L3', 'eTF018-NR1I2', 'eTF033-HHEX', 'eTF092-KLF9') | 23 |
| 40 | ('eTF008-FOXA1', 'eTF011-GATA4', 'eTF018-NR1I2', 'eTF033-HHEX') | 23 |
| 41 | ('eTF004-MLXIPL', 'eTF007-CREB3L3', 'eTF010-FOXA3', 'eTF092-KLF9') | 22 |
| 42 | ('eTF004-MLXIPL', 'eTF007-CREB3L3', 'eTF011-GATA4', 'eTF092-KLF9') | 22 |
| 43 | ('eTF006-ATF5', 'eTF007-CREB3L3', 'eTF011-GATA4', 'eTF033-HHEX') | 22 |
| 44 | ('eTF011-GATA4', 'eTF018-NR1I2', 'eTF033-HHEX', 'eTF092-KLF9') | 22 |
| 45 | ('eTF006-ATF5', 'eTF007-CREB3L3', 'eTF010-FOXA3', 'eTF033-HHEX') | 22 |
| 46 | ('eTF006-ATF5', 'eTF008-FOXA1', 'eTF010-FOXA3', 'eTF011-GATA4') | 22 |
| 47 | ('eTF004-MLXIPL', 'eTF010-FOXA3', 'eTF011-GATA4', 'eTF092-KLF9') | 22 |
| 48 | ('eTF006-ATF5', 'eTF007-CREB3L3', 'eTF008-FOXA1', 'eTF033-HHEX') | 21 |
| 49 | ('eTF004-MLXIPL', 'eTF008-FOXA1', 'eTF010-FOXA3', 'eTF011-GATA4') | 21 |
| 50 | ('eTF006-ATF5', 'eTF008-FOXA1', 'eTF011-GATA4', 'eTF092-KLF9') | 21 |
| 51 | ('eTF008-FOXA1', 'eTF010-FOXA3', 'eTF018-NR1I2', 'eTF033-HHEX') | 21 |
| 52 | ('eTF004-MLXIPL', 'eTF007-CREB3L3', 'eTF010-FOXA3', 'eTF018-NR1I2') | 21 |
| 53 | ('eTF004-MLXIPL', 'eTF007-CREB3L3', 'eTF010-FOXA3', 'eTF033-HHEX') | 21 |
| 54 | ('eTF006-ATF5', 'eTF007-CREB3L3', 'eTF033-HHEX', 'eTF092-KLF9') | 21 |
| 55 | ('eTF006-ATF5', 'eTF008-FOXA1', 'eTF010-FOXA3', 'eTF092-KLF9') | 21 |
| 56 | ('eTF008-FOXA1', 'eTF018-NR1I2', 'eTF033-HHEX', 'eTF092-KLF9') | 21 |
| 57 | ('eTF004-MLXIPL', 'eTF007-CREB3L3', 'eTF008-FOXA1', 'eTF092-KLF9') | 20 |
| 58 | ('eTF006-ATF5', 'eTF010-FOXA3', 'eTF011-GATA4', 'eTF033-HHEX') | 20 |
| 59 | ('eTF010-FOXA3', 'eTF018-NR1I2', 'eTF033-HHEX', 'eTF092-KLF9') | 20 |
| 60 | ('eTF007-CREB3L3', 'eTF009-FOXA2', 'eTF010-FOXA3', 'eTF011-GATA4') | 20 |

FIGURE 12 (continued)

(E) Table 6

| | Combination | % of cells with the combination |
|---|---|---|
| 0 | ('eTF007-CREB3L3', 'eTF010-FOXA3', 'eTF011-GATA4') | 42 |
| 1 | ('eTF007-CREB3L3', 'eTF008-FOXA1', 'eTF010-FOXA3') | 38 |
| 2 | ('eTF007-CREB3L3', 'eTF008-FOXA1', 'eTF011-GATA4') | 38 |
| 3 | ('eTF007-CREB3L3', 'eTF010-FOXA3', 'eTF033-HHEX') | 35 |
| 4 | ('eTF007-CREB3L3', 'eTF010-FOXA3', 'eTF092-KLF9') | 34 |
| 5 | ('eTF007-CREB3L3', 'eTF011-GATA4', 'eTF092-KLF9') | 33 |
| 6 | ('eTF008-FOXA1', 'eTF010-FOXA3', 'eTF011-GATA4') | 33 |
| 7 | ('eTF007-CREB3L3', 'eTF011-GATA4', 'eTF033-HHEX') | 32 |
| 8 | ('eTF007-CREB3L3', 'eTF008-FOXA1', 'eTF092-KLF9') | 32 |
| 9 | ('eTF007-CREB3L3', 'eTF010-FOXA3', 'eTF018-NR1I2') | 32 |
| 10 | ('eTF007-CREB3L3', 'eTF008-FOXA1', 'eTF033-HHEX') | 31 |
| 11 | ('eTF010-FOXA3', 'eTF011-GATA4', 'eTF092-KLF9') | 31 |
| 12 | ('eTF007-CREB3L3', 'eTF011-GATA4', 'eTF018-NR1I2') | 31 |
| 13 | ('eTF010-FOXA3', 'eTF011-GATA4', 'eTF033-HHEX') | 31 |
| 14 | ('eTF007-CREB3L3', 'eTF008-FOXA1', 'eTF018-NR1I2') | 30 |
| 15 | ('eTF010-FOXA3', 'eTF011-GATA4', 'eTF018-NR1I2') | 30 |
| 16 | ('eTF007-CREB3L3', 'eTF033-HHEX', 'eTF092-KLF9') | 29 |
| 17 | ('eTF008-FOXA1', 'eTF010-FOXA3', 'eTF092-KLF9') | 28 |
| 18 | ('eTF008-FOXA1', 'eTF011-GATA4', 'eTF092-KLF9') | 28 |
| 19 | ('eTF008-FOXA1', 'eTF010-FOXA3', 'eTF018-NR1I2') | 27 |
| 20 | ('eTF006-ATF5', 'eTF007-CREB3L3', 'eTF011-GATA4') | 27 |
| 21 | ('eTF008-FOXA1', 'eTF010-FOXA3', 'eTF033-HHEX') | 27 |
| 22 | ('eTF008-FOXA1', 'eTF011-GATA4', 'eTF033-HHEX') | 27 |
| 23 | ('eTF006-ATF5', 'eTF007-CREB3L3', 'eTF010-FOXA3') | 27 |
| 24 | ('eTF008-FOXA1', 'eTF011-GATA4', 'eTF018-NR1I2') | 27 |
| 25 | ('eTF010-FOXA3', 'eTF033-HHEX', 'eTF092-KLF9') | 27 |
| 26 | ('eTF007-CREB3L3', 'eTF018-NR1I2', 'eTF092-KLF9') | 26 |
| 27 | ('eTF011-GATA4', 'eTF033-HHEX', 'eTF092-KLF9') | 26 |
| 28 | ('eTF004-MLXIPL', 'eTF007-CREB3L3', 'eTF010-FOXA3') | 26 |
| 29 | ('eTF007-CREB3L3', 'eTF018-NR1I2', 'eTF033-HHEX') | 25 |
| 30 | ('eTF010-FOXA3', 'eTF018-NR1I2', 'eTF092-KLF9') | 25 |
| 31 | ('eTF008-FOXA1', 'eTF033-HHEX', 'eTF092-KLF9') | 25 |
| 32 | ('eTF011-GATA4', 'eTF018-NR1I2', 'eTF033-HHEX') | 25 |
| 33 | ('eTF006-ATF5', 'eTF010-FOXA3', 'eTF011-GATA4') | 25 |
| 34 | ('eTF011-GATA4', 'eTF018-NR1I2', 'eTF092-KLF9') | 25 |
| 35 | ('eTF006-ATF5', 'eTF007-CREB3L3', 'eTF008-FOXA1') | 25 |
| 36 | ('eTF004-MLXIPL', 'eTF007-CREB3L3', 'eTF011-GATA4') | 24 |
| 37 | ('eTF004-MLXIPL', 'eTF010-FOXA3', 'eTF011-GATA4') | 24 |
| 38 | ('eTF006-ATF5', 'eTF007-CREB3L3', 'eTF092-KLF9') | 24 |

FIGURE 12 (continued)

(E) Table 6 (continued)

| | Combination | % of cells with the combination |
|---|---|---|
| 39 | ('eTF008-FOXA1', 'eTF018-NR1I2', 'eTF092-KLF9') | 24 |
| 40 | ('eTF010-FOXA3', 'eTF018-NR1I2', 'eTF033-HHEX') | 23 |
| 41 | ('eTF004-MLXIPL', 'eTF007-CREB3L3', 'eTF008-FOXA1') | 23 |
| 42 | ('eTF006-ATF5', 'eTF011-GATA4', 'eTF092-KLF9') | 23 |
| 43 | ('eTF006-ATF5', 'eTF008-FOXA1', 'eTF010-FOXA3') | 22 |
| 44 | ('eTF006-ATF5', 'eTF008-FOXA1', 'eTF011-GATA4') | 22 |
| 45 | ('eTF006-ATF5', 'eTF010-FOXA3', 'eTF092-KLF9') | 22 |
| 46 | ('eTF008-FOXA1', 'eTF018-NR1I2', 'eTF033-HHEX') | 22 |
| 47 | ('eTF006-ATF5', 'eTF007-CREB3L3', 'eTF033-HHEX') | 21 |
| 48 | ('eTF004-MLXIPL', 'eTF008-FOXA1', 'eTF010-FOXA3') | 21 |
| 49 | ('eTF004-MLXIPL', 'eTF007-CREB3L3', 'eTF092-KLF9') | 21 |
| 50 | ('eTF018-NR1I2', 'eTF033-HHEX', 'eTF092-KLF9') | 21 |
| 51 | ('eTF006-ATF5', 'eTF008-FOXA1', 'eTF092-KLF9') | 21 |
| 52 | ('eTF004-MLXIPL', 'eTF008-FOXA1', 'eTF011-GATA4') | 20 |
| 53 | ('eTF004-MLXIPL', 'eTF010-FOXA3', 'eTF092-KLF9') | 20 |
| 54 | ('eTF007-CREB3L3', 'eTF009-FOXA2', 'eTF010-FOXA3') | 20 |
| 55 | ('eTF004-MLXIPL', 'eTF007-CREB3L3', 'eTF018-NR1I2') | 20 |
| 56 | ('eTF007-CREB3L3', 'eTF008-FOXA1', 'eTF009-FOXA2') | 20 |

FIGURE 12 (continued)

METHOD OF GENERATING HEPATIC CELLS

CROSS REFERENCE TO RELATED APPLICATIONS

This application is a divisional of U.S. patent application Ser. No. 17/206,451, filed Mar. 19, 2021, which is a continuation of International Application PCT/GB2021/050622, filed Mar. 11, 2021, which claims the benefit of U.S. Provisional Application No. 62/988,349 filed Mar. 11, 2020.

FIELD OF THE INVENTION

The invention relates to methods of generating hepatic cells by overexpressing combinations of transcription factors.

BACKGROUND OF THE INVENTION

Hepatocytes are the main functional cells of the liver. They provide a wide array of essential functions, including regulation of glucose and lipid metabolism, detoxification of various metabolites and drugs, protein synthesis, and bile synthesis.

In drug screens it is essential to determine if a potential drug candidate may cause hepatotoxicity. Currently, screens for hepatotoxicity and drug dose typically use a range of immortalised hepatic cell lines and human primary hepatocytes. However, immortalized cells do not possess key hepatic drug metabolizing functions. Primary hepatocytes are limited in supply, subject to isolation and cryopreservation stress and show batch-to-batch variation, and therefore are not ideal for high throughput screens. Moreover, the drug metabolizing functions of human primary hepatocytes can vary significantly according to genetic background. The availability of a consistent and scalable supply of functional human hepatocytes would greatly facilitate both drug development and clinical application to liver failure therapies. Generation of hepatic cells from induced pluripotent stem cells (iPSC) has previously been investigated, however current state-of-the-art methods do not provide the level of functionality, consistency and scalability required for high throughput drug screens. Moreover, iPSC-derived hepatic cells made with current methods remain metabolically deficient and therefore are not suitable as a predictive physiological model (Williams, 2018).

iPSC-derived hepatic cells can advance drug discovery and cell therapy in many ways. Mature hepatocytes can be used in drug discovery as surrogates for primary hepatocytes to test the effects of drugs on the liver (Williams, 2018). An added benefit of iPSC-derived hepatocytes is their ability to model liver disease. Thus, they provide unique tools to test efficacy of drugs on patient-derived cells. Transplantation of immature or mature hepatocytes, or hepatic progenitors can be an alternative to whole liver transplantation for patients suffering from acute liver failure, or liver-borne metabolic diseases when combined with gene therapy (Iansante et al., 2018).

There is therefore a need in the art to provide methods for generating hepatic cells suitable for use as research tools and as potential therapeutic agents.

SUMMARY OF THE INVENTION

According to a first aspect of the invention, there is provided a method of generating hepatic cells comprising increasing the expression of at least three or more transcription factors, wherein the three or more transcription factors are selected from the group consisting of: FOXA1 or FOXA3; NR1I2 or NR1I3; HHEX; CREB3L3; GATA4; KLF9; ATF5; MLXIPL; FOXA2; AR; ARID3C; CEBPA; CUX2; EPAS1; HLF; HNF1A; HNF4A; HNF4G; KLF15; NCOA2; NR0B2; NR1H4; NR5A2; ONECUT1; ONECUT2; PPARA; PROX1; RORA; RORC; RXRA; SALL1; SMAD1; SREBF1; STAT3; TSHZ2; XBP1; ZBTB16; and variants thereof, in a non-hepatic cell population and culturing the cell population to obtain hepatic cells.

According to a further aspect of the invention, there is provided a method for the production of hepatic cells from a source cell, comprising the steps of:
 a) targeted insertion of a gene encoding a transcriptional regulator protein into a first genetic safe harbour site of the source cell; and
 b) targeted insertion of at least three or more transcription factors, wherein the three or more transcription factors are selected from the group consisting of: FOXA1 or FOXA3; NR1I2 or NR1I3; HHEX; CREB3L3; GATA4; KLF9; ATF5; MLXIPL; FOXA2; AR; ARID3C; CEBPA; CUX2; EPAS1; HLF; HNF1A; HNF4A; HNF4G; KLF15; NCOA2; NR0B2; NR1H4; NR5A2; ONECUT1; ONECUT2; PPARA; PROX1; RORA; RORC; RXRA; SALL1; SMAD1; SREBF1; STAT3; TSHZ2; XBP1; ZBTB16; and variants thereof, operably linked to an inducible promoter into a second genetic safe harbour site of the source cell, wherein said inducible promoter is regulated by the transcriptional regulator protein; and
 c) culturing the source cell(s) comprising the insertions to obtain hepatic cells.

According to a further aspect of the invention, there is provided a use of at least three or more transcription factors wherein the three or more transcription factors are selected from the group consisting of: FOXA1 or FOXA3; NR1I2 or NR1I3; HHEX; CREB3L3; GATA4; KLF9; ATF5; MLXIPL; FOXA2; AR; ARID3C; CEBPA; CUX2; EPAS1; HLF; HNF1A; HNF4A; HNF4G; KLF15; NCOA2; NR0B2; NR1H4; NR5A2; ONECUT1; ONECUT2; PPARA; PROX1; RORA; RORC; RXRA; SALL1; SMAD1; SREBF1; STAT3; TSHZ2; XBP1; ZBTB16; and variants thereof, to generate hepatic cells.

According to a further aspect of the invention, there is provided a cell obtainable by any one of the methods defined herein.

According to a further aspect of the invention, there is provided a cell comprising one or more exogenous expression cassettes encoding at least three or more transcription factors, wherein the three or more transcription factors are selected from the group consisting of: FOXA1 or FOXA3; NR1I2 or NR1I3; HHEX; CREB3L3; GATA4; KLF9; ATF5; MLXIPL; FOXA2; AR; ARID3C; CEBPA; CUX2; EPAS1; HLF; HNF1A; HNF4A; HNF4G; KLF15; NCOA2; NR0B2; NR1H4; NR5A2; ONECUT1; ONECUT2; PPARA; PROX1; RORA; RORC; RXRA; SALL1; SMAD1; SREBF1; STAT3; TSHZ2; XBP1; ZBTB16; and variants thereof.

According to a further aspect of the invention, there is provided a cell as defined herein, for use in therapy.

According to a further aspect of the invention, there is provided a kit for differentiating a cell into a hepatic cell comprising:
 (i) a source cell and an agent that activates or increases the expression or amount of at least three or more transcription factors; and/or (ii) one or more expression cassettes encoding at least three or more transcription factors, wherein the three or more transcription factors is selected from the group consisting of: FOXA1 or FOXA3; NR1I2 or NR1I3; HHEX; CREB3L3; GATA4; KLF9; ATF5; MLXIPL; FOXA2; AR; ARID3C; CEBPA; CUX2; EPAS1; HLF; HNF1A; HNF4A; HNF4G; KLF15; NCOA2; NR0B2; NR1H4; NR5A2; ONECUT1; ONECUT2; PPARA; PROX1; RORA; RORC; RXRA; SALL1; SMAD1; SREBF1; STAT3; TSHZ2; XBP1; ZBTB16; and variants thereof.

According to a further aspect of the invention, there is provided a use of a kit as defined herein, for differentiating a cell into a hepatic cell.

According to a further aspect of the invention, there is provided a method of drug screening comprising contacting a hepatic cell generated using the method as defined herein, or a hepatic cell as defined herein, with the drug and observing a change in the hepatic cells induced by the drug.

According to a further aspect of the invention, there is provided a method for treating a subject having or at risk of a liver disease or dysfunction comprising administering to the subject a therapeutically effective amount of hepatic cells generated using the method as defined herein, or hepatic cells as defined herein.

Human iPSCs carrying the albumin gene fused to red fluorescent protein (ALB:RFP) and the cytochrome P450 3A4 gene fused to green fluorescent protein (CYP3A4:GFP) double reporters were transduced with a pool of lentiviral vectors each carrying a single transcription factor. The lentiviral vector dosage was adjusted to result in 6 or fewer unique transcription factors per cell in most cells. On day 11 post-LV transduction, cells expressing both reporters were isolated by fluorescence activated cell sorting and subjected to single cell RNA sequencing.

Figure 2:
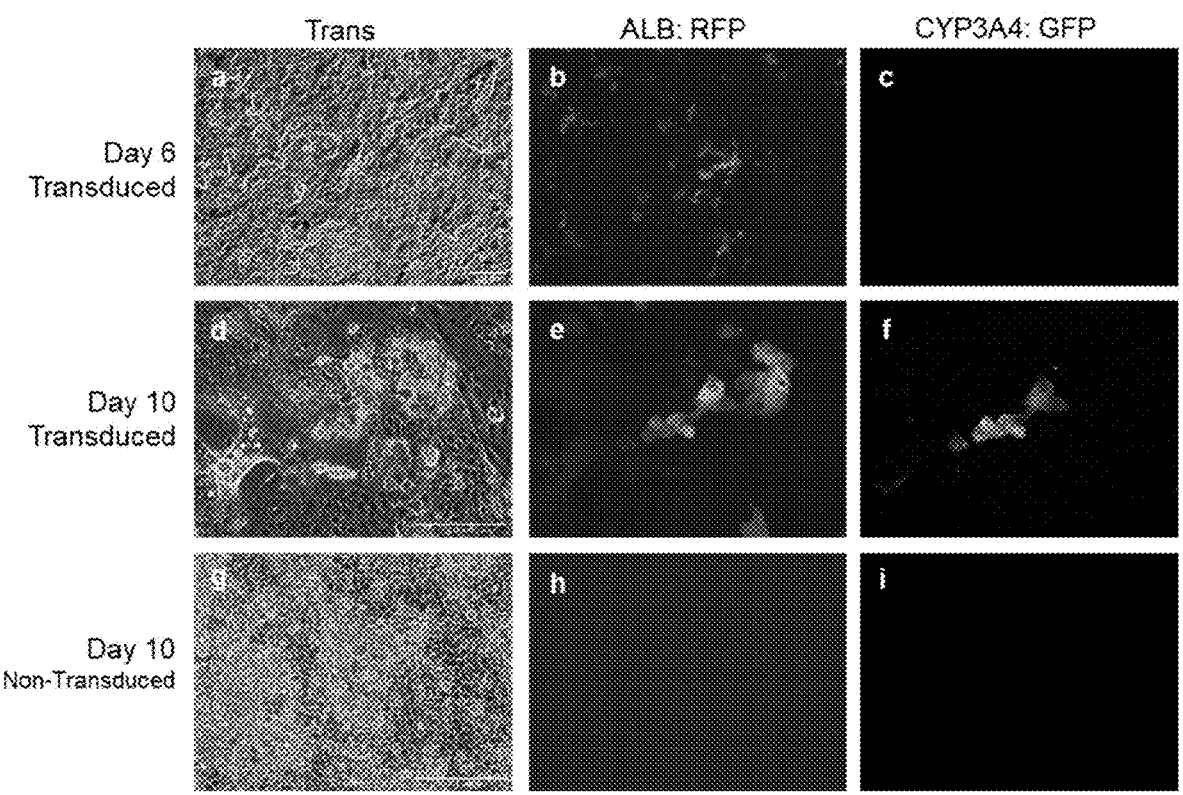

FIG. 2. Generation of ALB+ and CYP3A4+ cells from 39 TFs

Transmitted light (Trans) and epifluorescence images of day 6 (a-c) and day 10 (d-f) post-LV transduction and day 10 non-transduced (g-i) cells.

Figure 3:
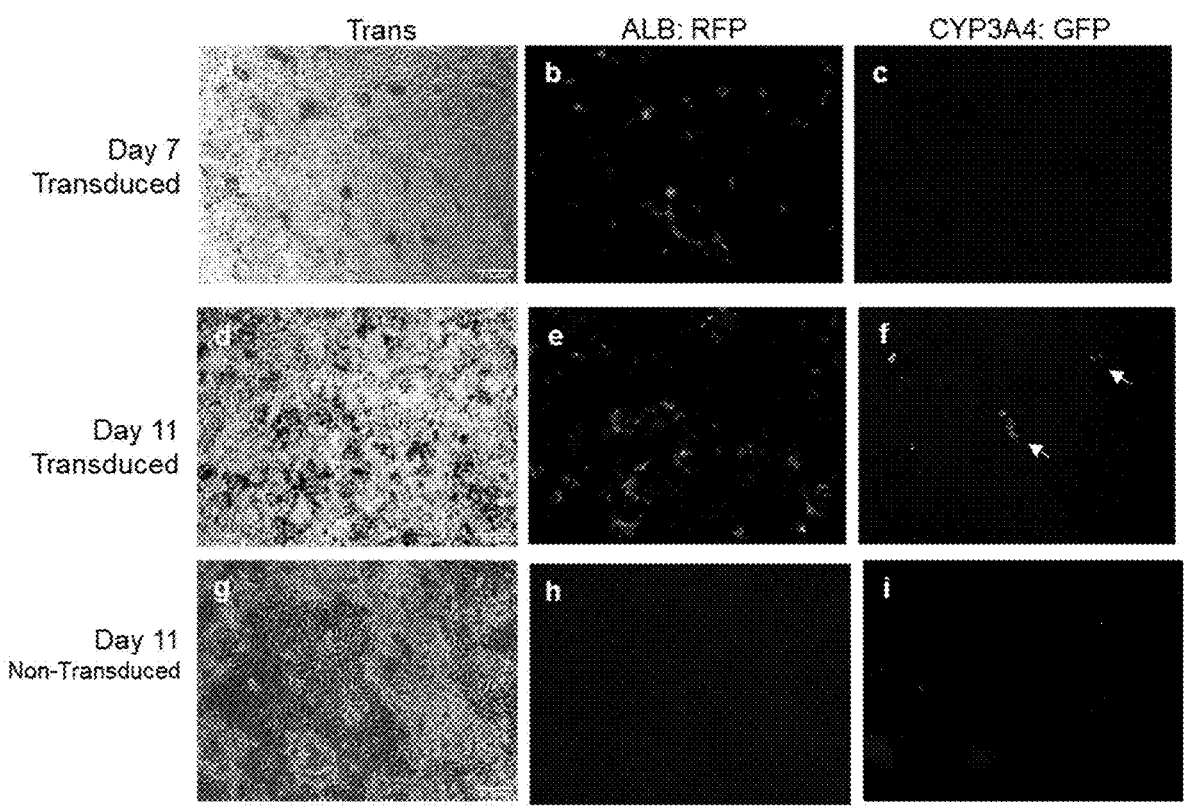

FIG. 3. Generation of ALB+ and CYP3A4+ cells from 34 TFs

Transmitted light (Trans) and epifluorescence images of day 7 (a-c) and day 11 (d-f) post-LV transduction and day 11 non-transduced (g-i) cells.

Figure 4:
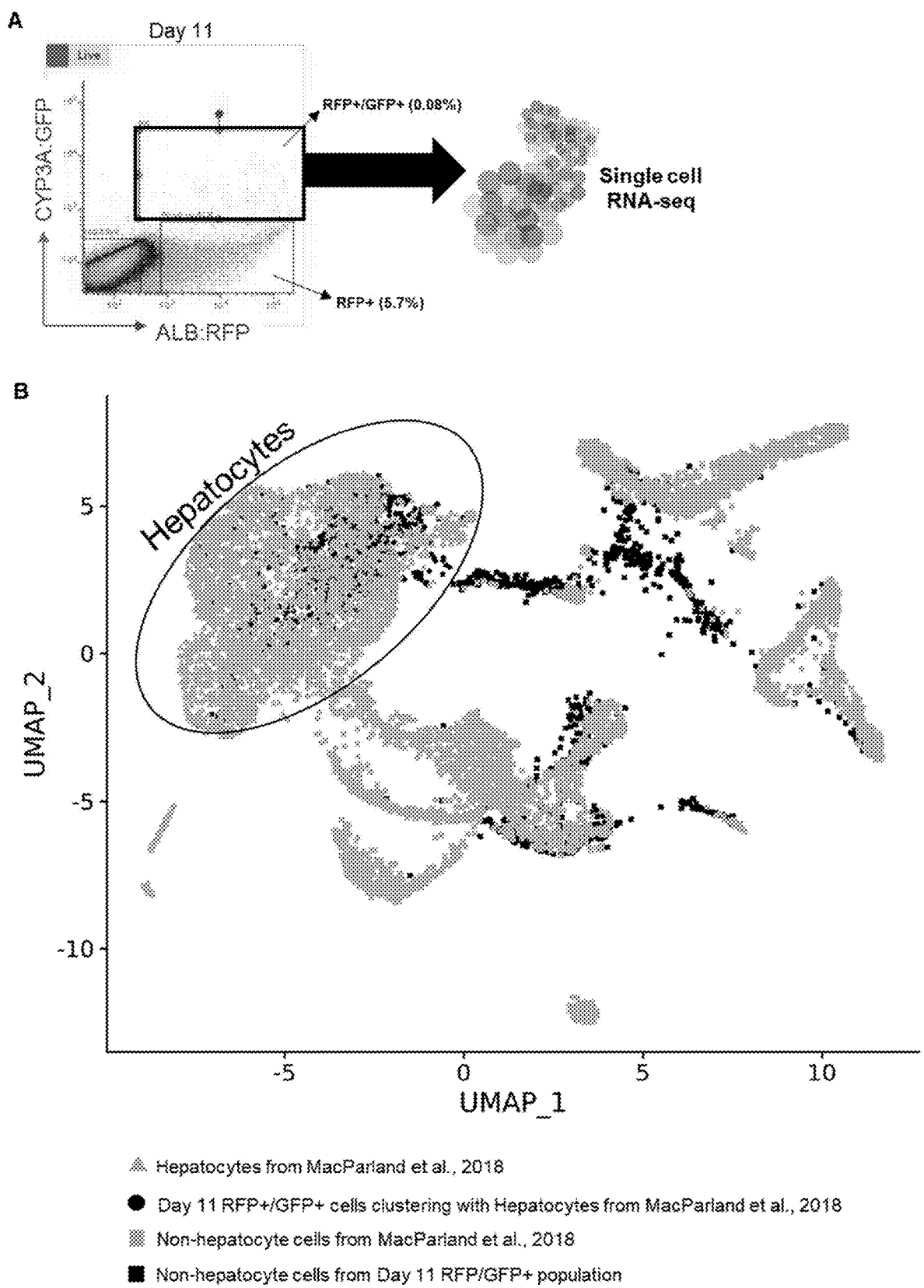

FIG. 4. Single cell RNA sequencing of Day 11 ALB-RFP+/CYP3A4-GFP+ cells (A) Flow cytometry dot-plot of day 11 cells transduced with 34 TFs. ALB:RFP+/CYP3A4:GFP+ cells were sorted and subjected to single cell RNA-seq.

(B) Clustering of sorted day 11 cells and liver cells from MacParland et al., 2018, using Uniform Manifold Approximation and Projection (UMAP), based on expression levels of all genes expressed in two datasets. Non-hepatocyte cell types residing in human liver such as cholangiocytes, Kuppfer cells, stellate cells, endothelial cells and immune cells, which are included in MacParland et al., 2018 dataset are denoted by gray squares.

Figure 5:
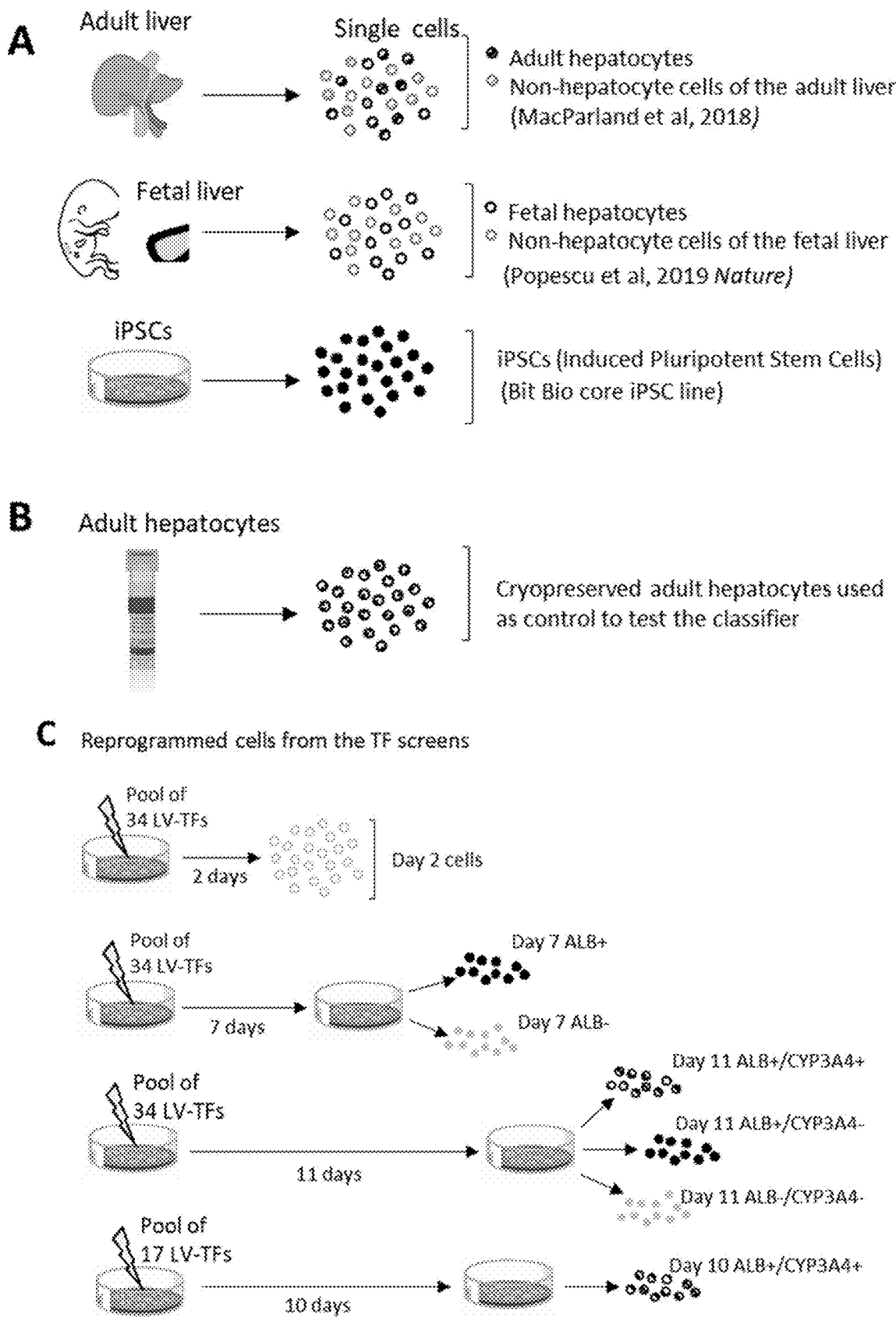

FIG. 5. Single cell RNA-seq (scRNA-seq) datasets used to decode transcription factor combinations that induce hepatocyte reprogramming. (A) Summary of reference cells: Adult hepatocytes (MacParland et al, 2018), fetal hepatocytes (Popescu et al, 2019), non-hepatocyte cells of the adult and fetal liver (MacParland et al, 2018 and Popescu et al, 2019) and induced pluripotent stem cells (iPSCs). (B) Cryopreserved adult hepatocytes used as control to test the cell classifier. (C) Summary of strategy for reprogramming cells from transcription factor (TF) screens in which TFs were introduced into iPSCs from a pool of 34 (TFs in Table 2) or 17 (TFs in Table 3 plus PROX1) using lentiviruses each carrying a single TF: On days 7, 10 and 11 of reprogramming, cells were sorted by flow cytometry based on expression of the ALB and/or CYP3A4 reporters. Day 2, 7 and 11 cells were obtained from the 34 TF screen. Day 10 ALB+/CYP3A4+ cells were obtained from the 17 TF screen.

Figure 6:
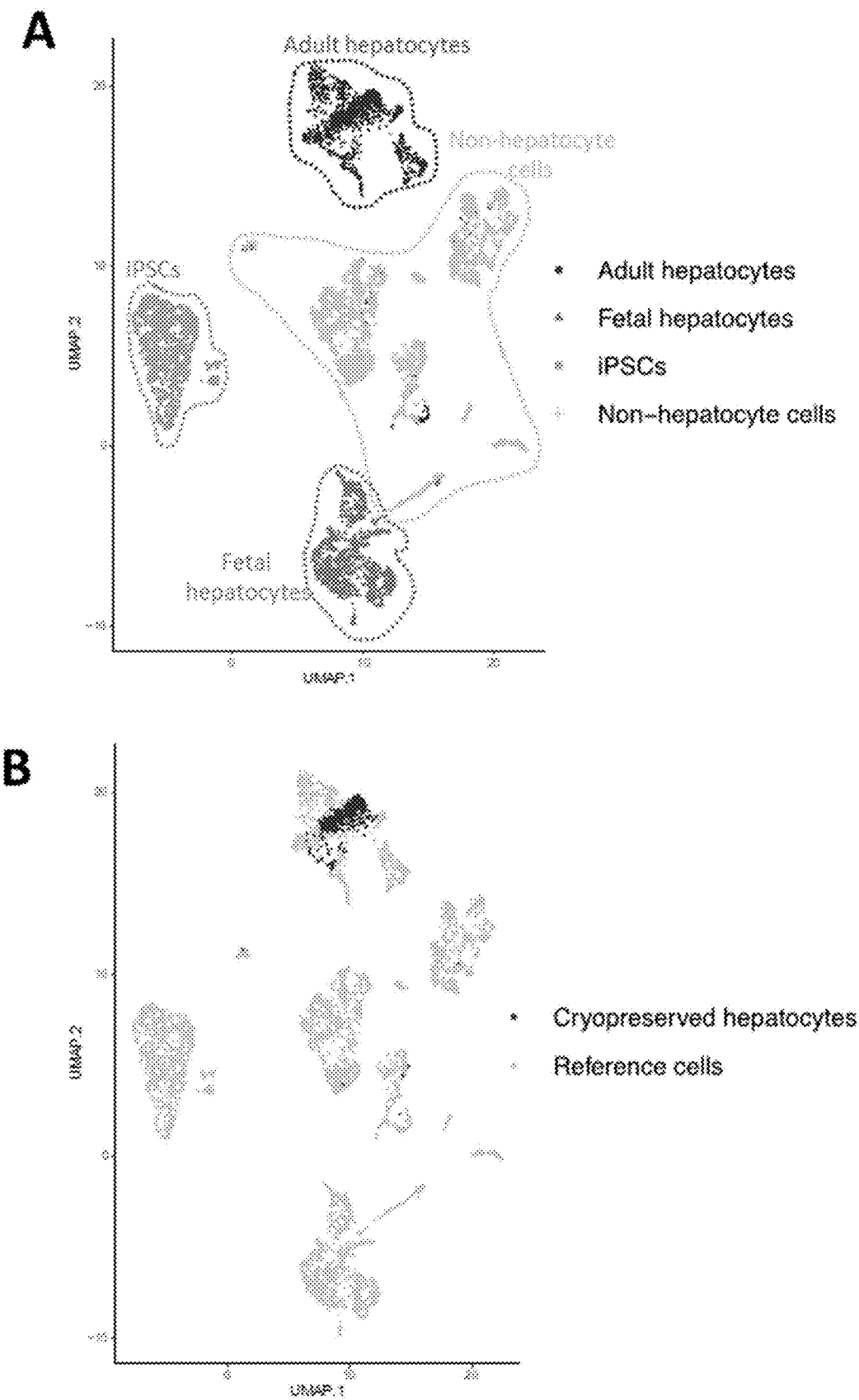
Figure 6:
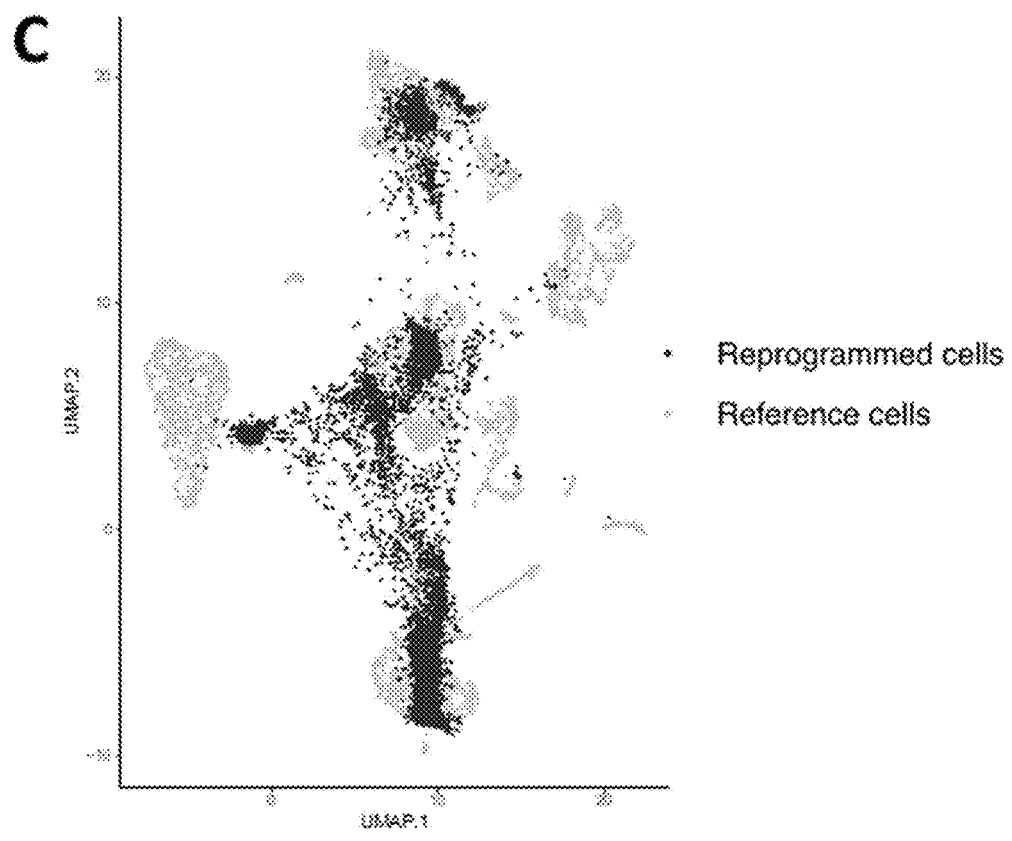
Figure 6:
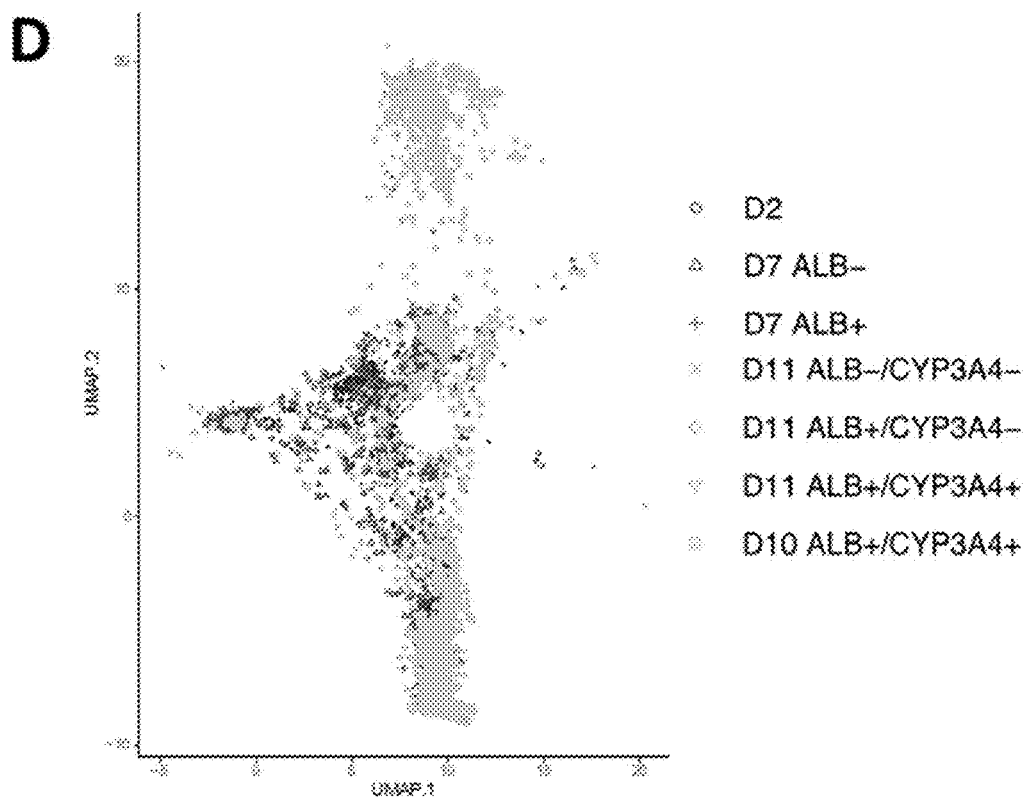

FIG. 6. Clustering of reprogrammed cells with reference cells. (A) UMAP plot showing single cell transcriptomes of reference cells. (B) UMAP plot showing single cell transcriptomes of reference cells (grey) and cryopreserved hepatocytes (black) used as a control. (C) UMAP plot showing clustering of reference cells (grey) and reprogrammed cells (black). (D) UMAP plot showing single cell transcriptomes of reprogrammed cells from different timepoints during reprogramming sorted by flow cytometry as described in FIG. 5C. (E) Table showing the percentage of reprogrammed cells in different clusters.

Figure 7:
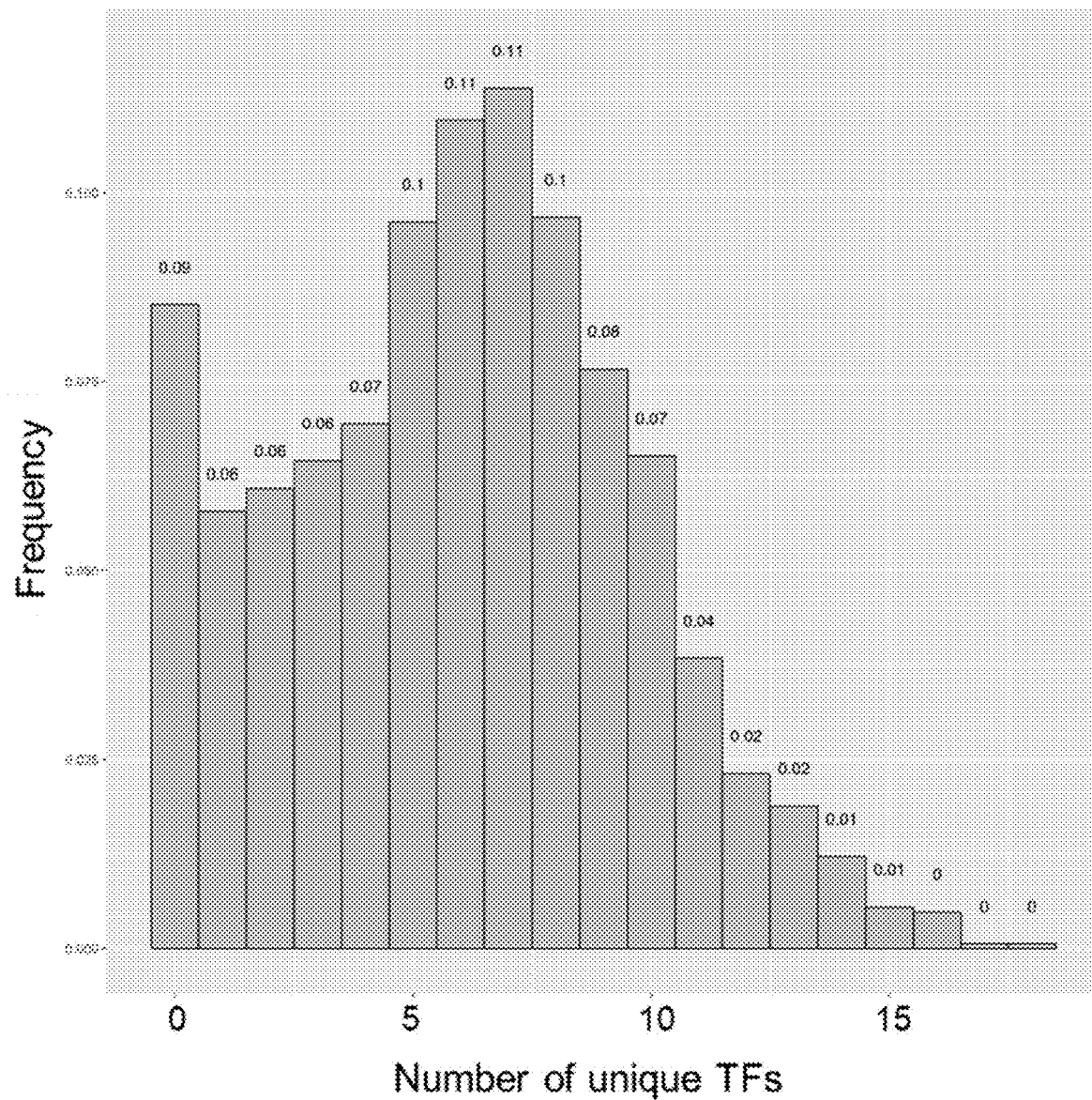

FIG. 7. Expression of exogenous transcription factors (eTFs) in single cells of Day 11 RFP+/GFP+ population Histogram showing frequency of cells expressing different number of unique exogenous TFs (eTFs)

Figure 8:
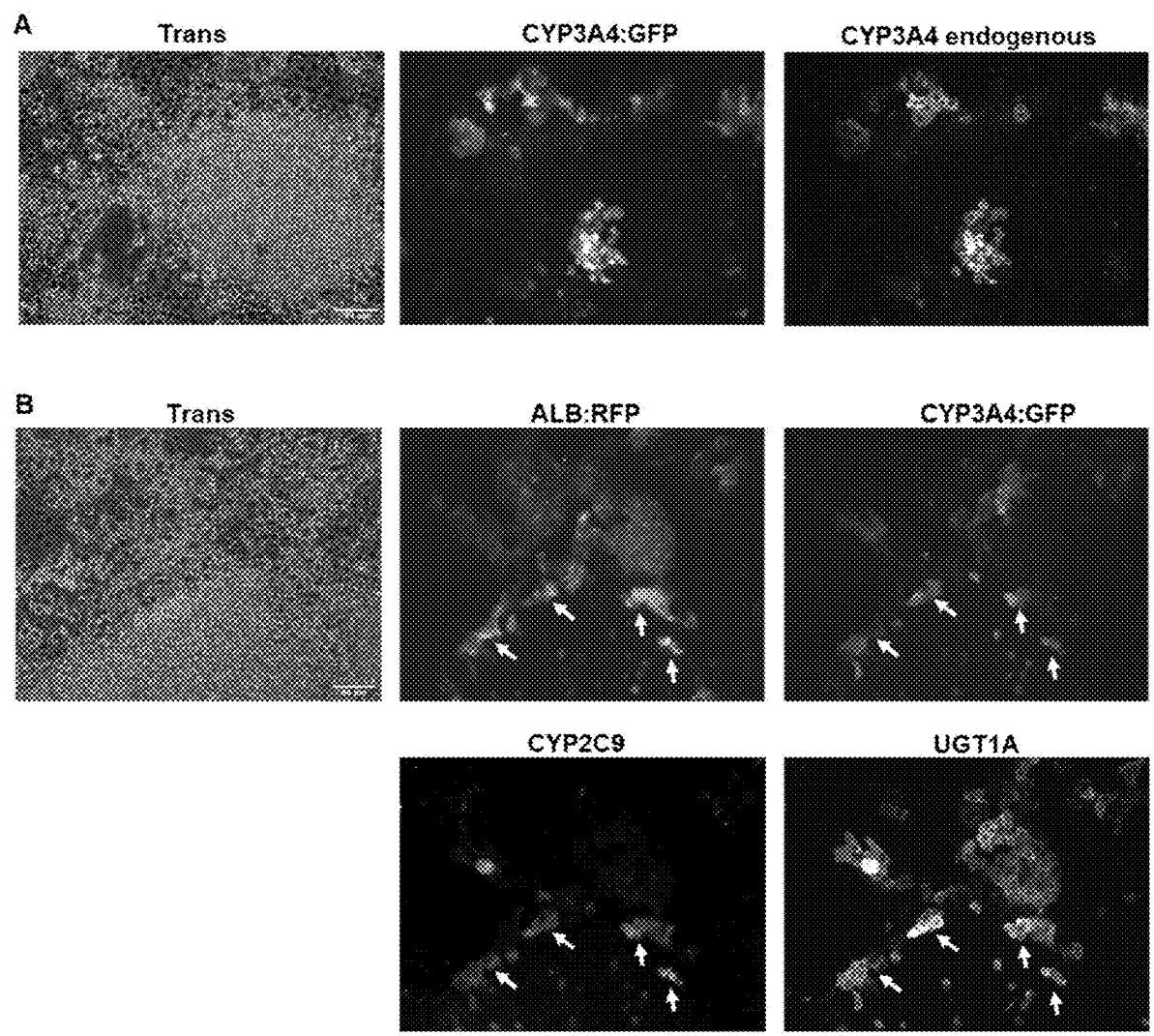

FIG. 8. Expression of mature hepatocyte markers in cells programmed with 14 TFs

Transmitted light (Trans) and epifluorescence images of cells on day 13, following transduction with a pool of lentiviral vector carrying 14 TFs listed in Table 4.

(A) Trans and epifluorescence images of cells stained with an antibody against CYP3A4 protein (B) Trans and epifluorescence images of cells stained with antibodies against CYP2C9 and UGT1A proteins. Arrowheads point at cells that co-express all 4 hepatic markers.

Figure 9:
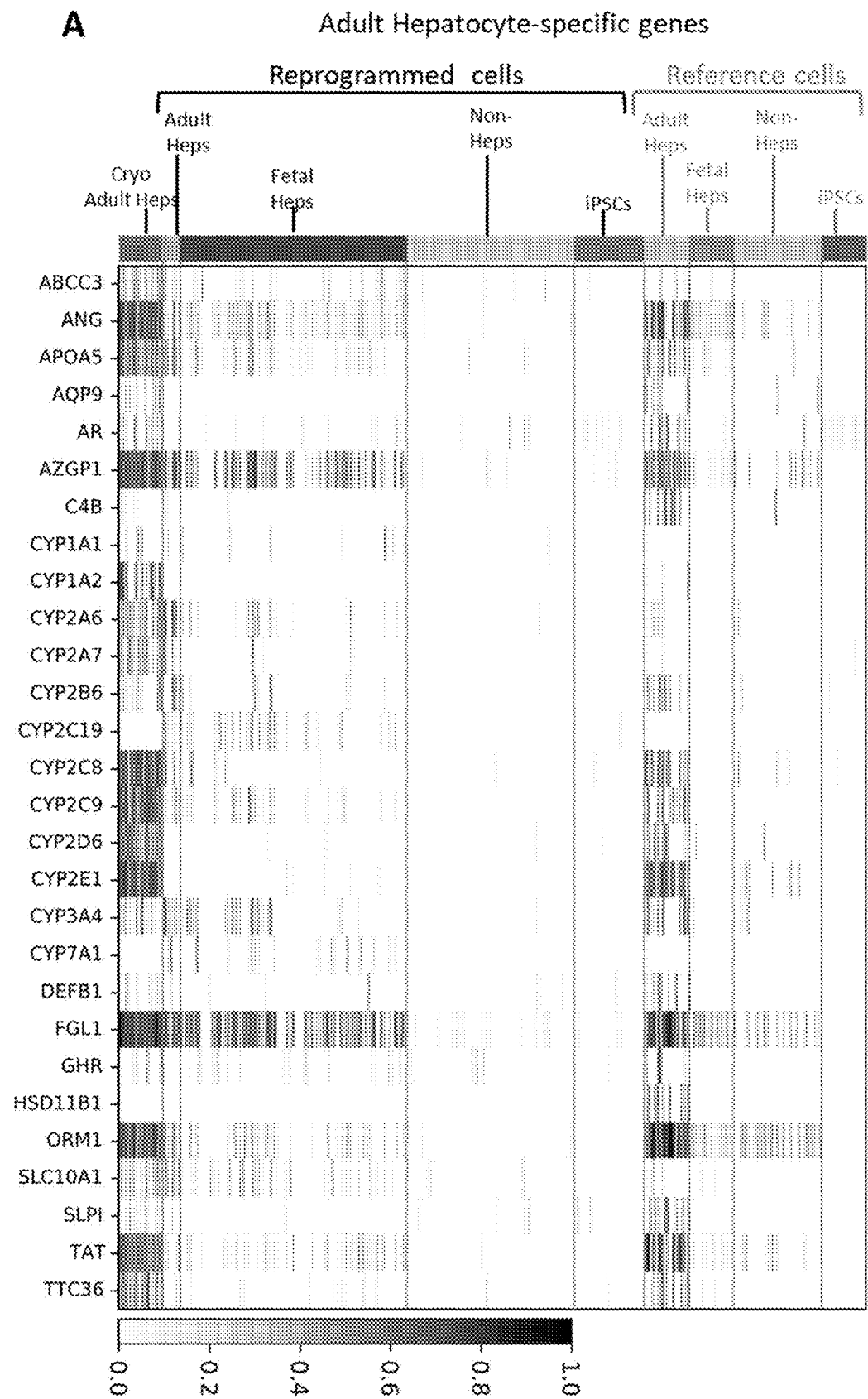
Figure 9:
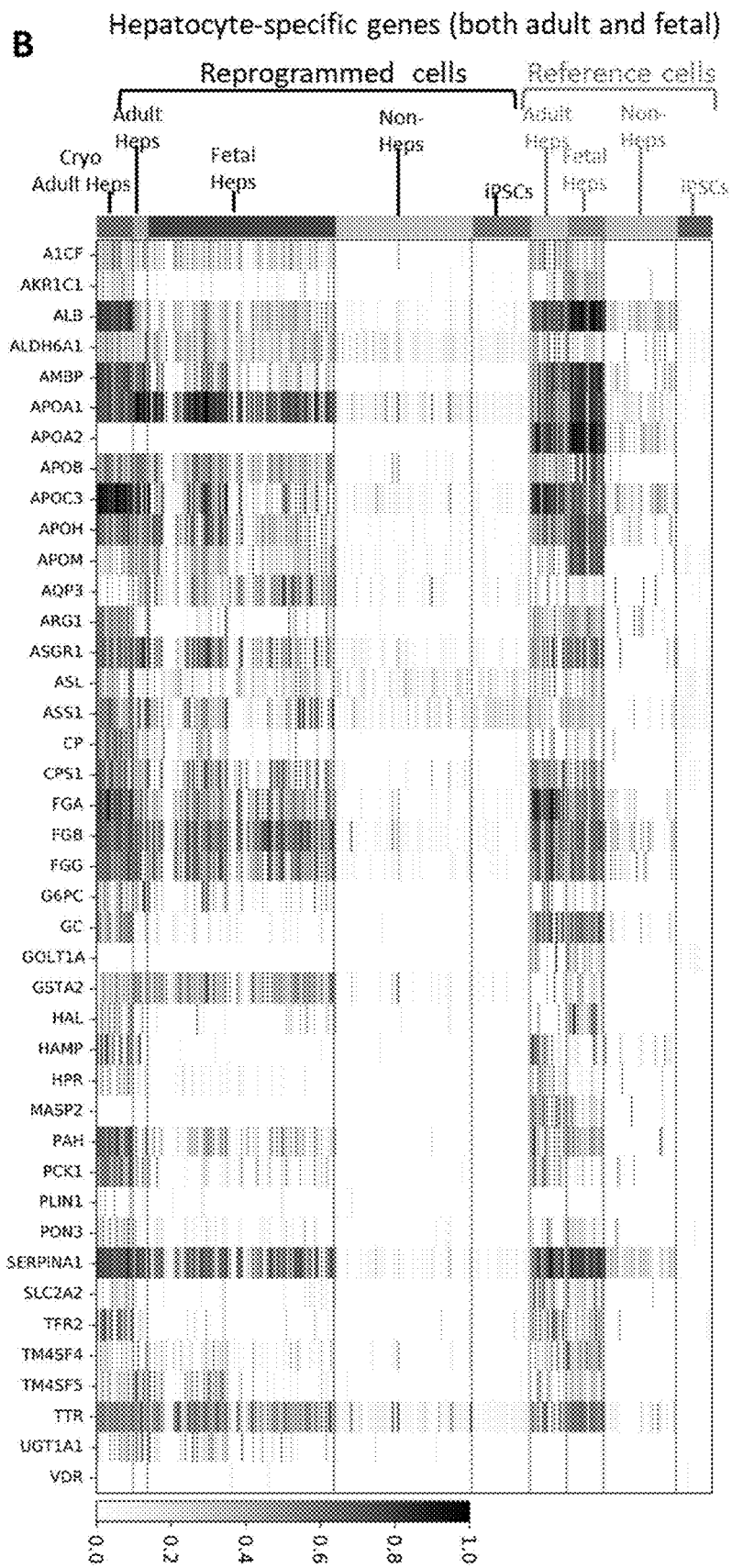
Figure 9:
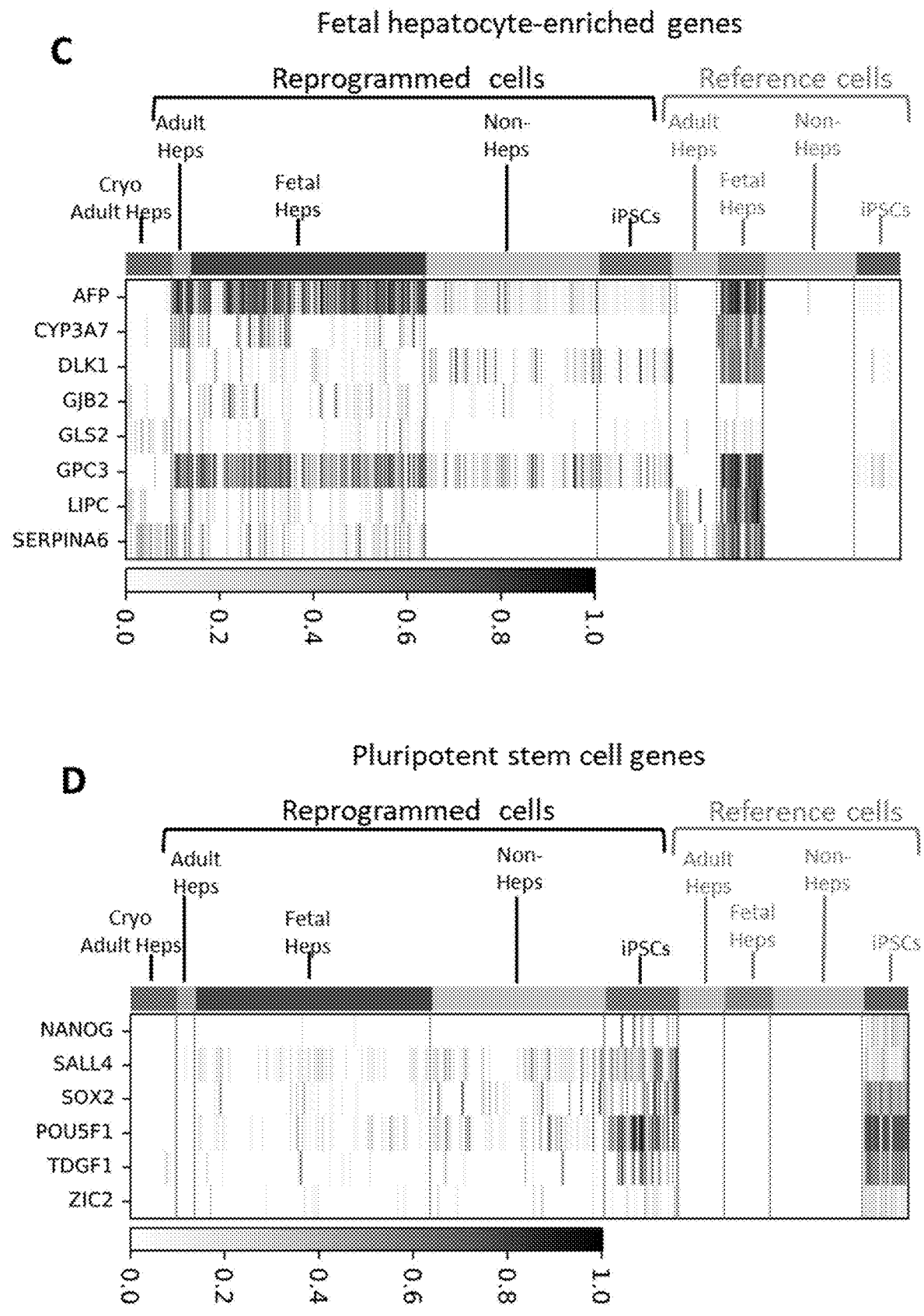

FIG. 9. Heatmap showing expression of cell type-specific genes. Cells are grouped into cell type clusters based on UMAP clustering from FIG. 6. Single cells are aligned across the horizontal axis and normalized gene expression levels are plotted. Scale at the bottom shows scaled normalized gene expression level. Cell type-specific genes are shown along the vertical axis. (A) Adult hepatocyte-specific genes; (B) genes expressed both in adult and fetal hepatocytes; (C) genes enriched in fetal hepatocytes; and (D) pluripotent stem cell genes FIG. 10. Heatmap showing expression of genes associated with hepatocyte-specific cellular functions. Single cells are aligned across the horizontal axis and normalized gene expression levels are plotted. Genes are grouped according to association with specific functions and are shown along the vertical axis. Scale at the bottom shows scaled normalized gene expression level. (A) Genes with functions in amino acid, glucose and lipid metabolism; (B) genes with functions in drug metabolism.

Figure 11:
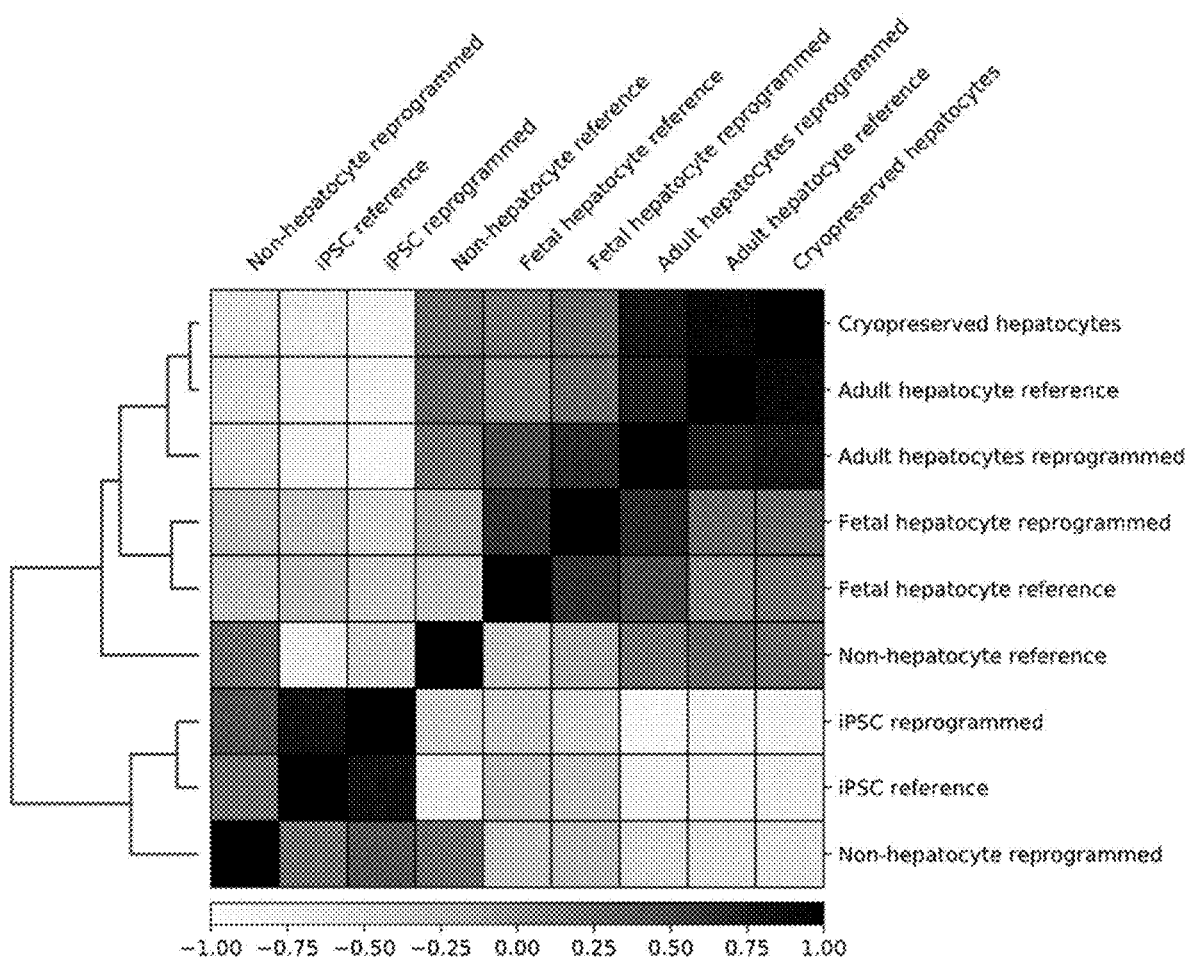

FIG. 11. Hierarchical clustering based on normalized expression of all genes detected across the datasets.

Figure 12:
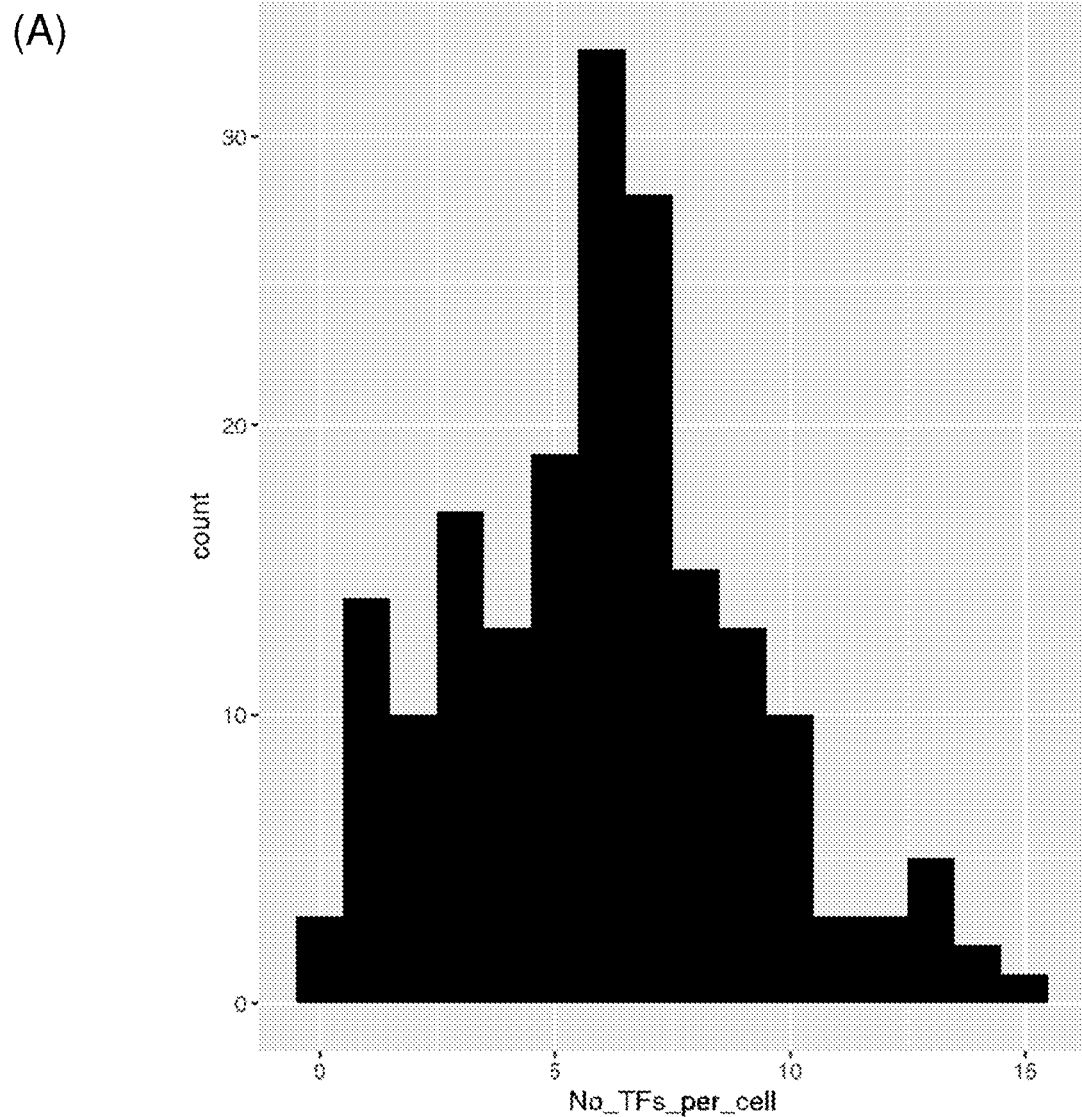
Figure 12:
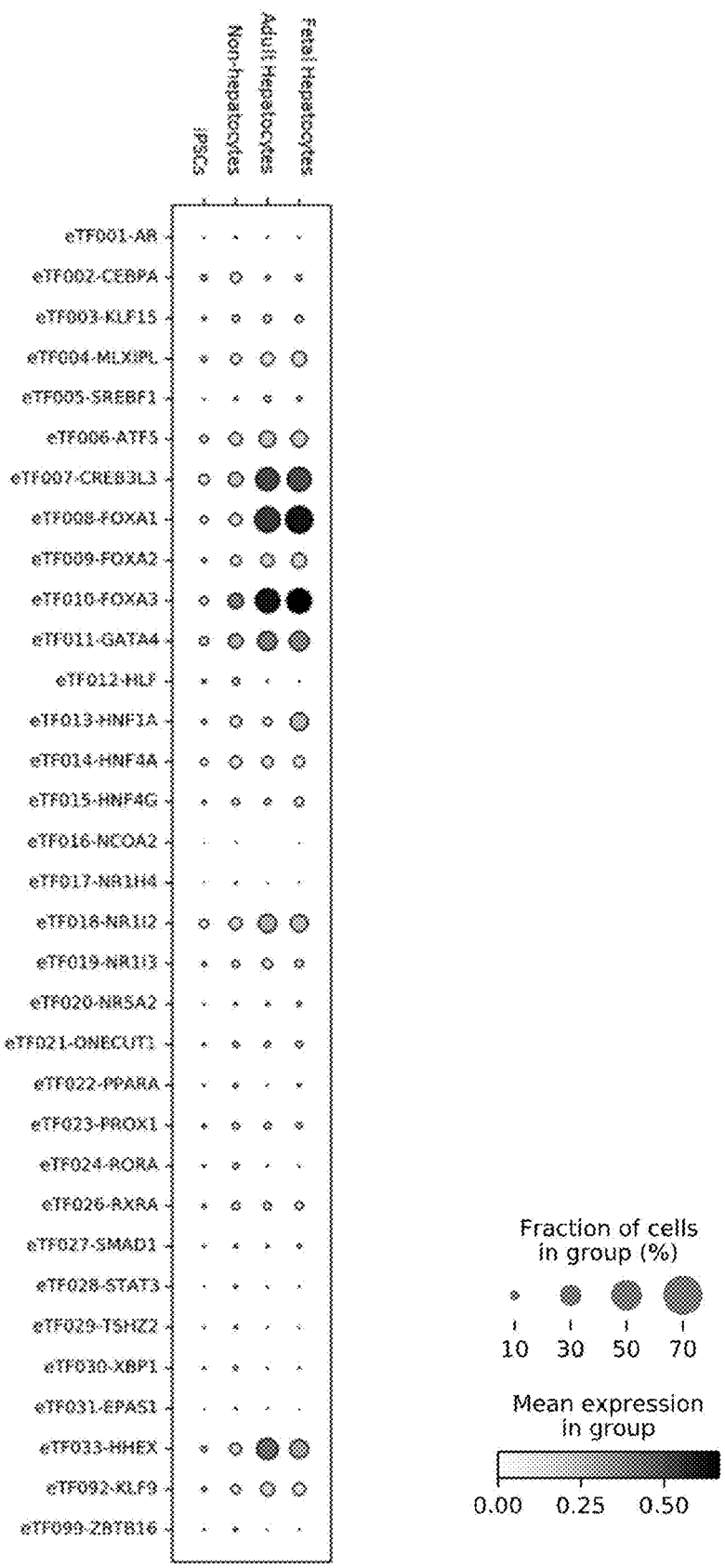
Figure 12:
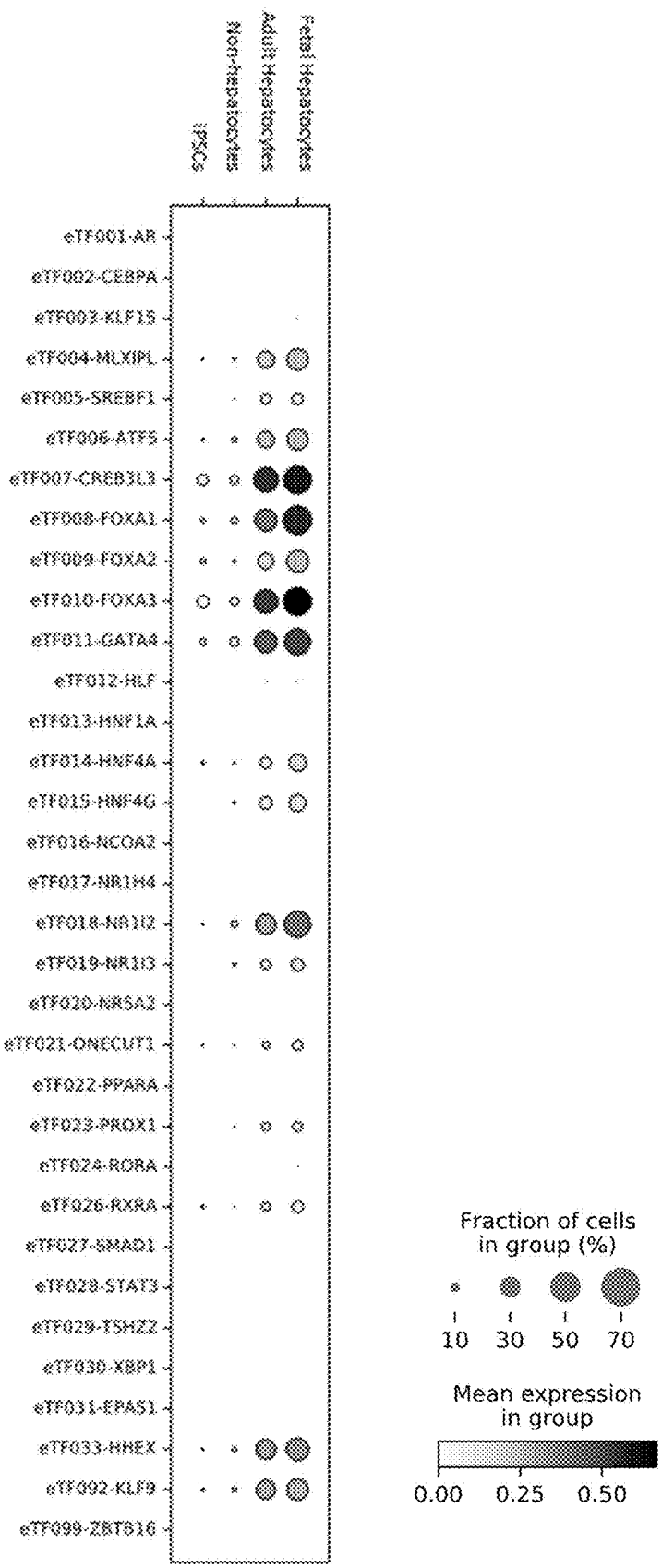

FIG. 12. Transcription factor content of reprogrammed cells that cluster with reference cell types. (A) Bar graph showing the number of unique TFs detected in cells that cluster with reference adult hepatocytes. (B) Dot plot showing single TF expression profiles in reprogrammed cells obtained from 34 TF screen. The rows (from top to bottom)

show groups of reprogrammed cells that cluster with fetal hepatocytes, adult hepatocytes, non-hepatocyte cells (other liver cells) and iPSCs. (C) Dot plot showing single TF expression profiles in reprogrammed cells obtained from 17 TF screen. The rows (from top to bottom) show groups of reprogrammed cells that cluster with fetal hepatocytes, adult hepatocytes, non-hepatocyte cells (other liver cells) and iPSCs. (D) Table 5 lists the 4 TF combinations that are enriched in adult hepatocyte cluster from the TF screens. (E) Table 6 lists the 3 TF combinations that are enriched in the adult hepatocyte cluster from both TF screens.

Figure 13:
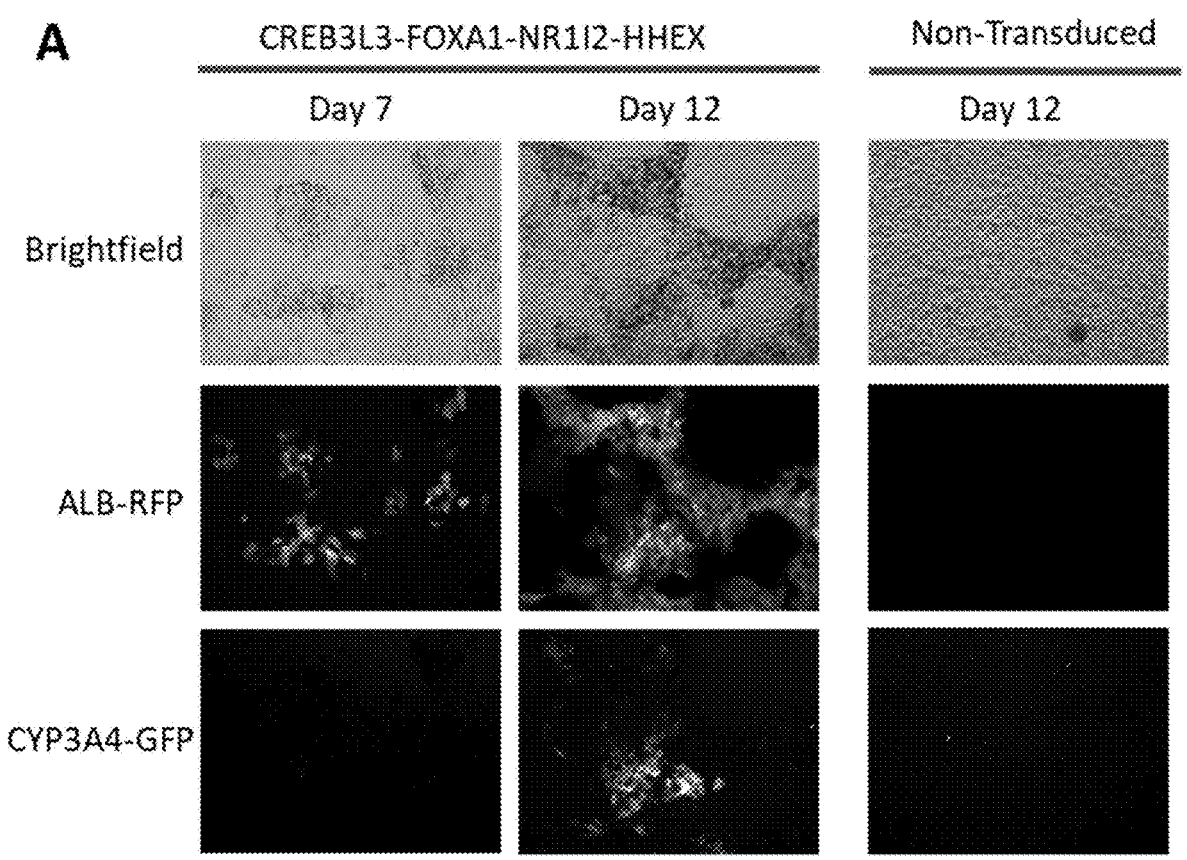
Figure 13:
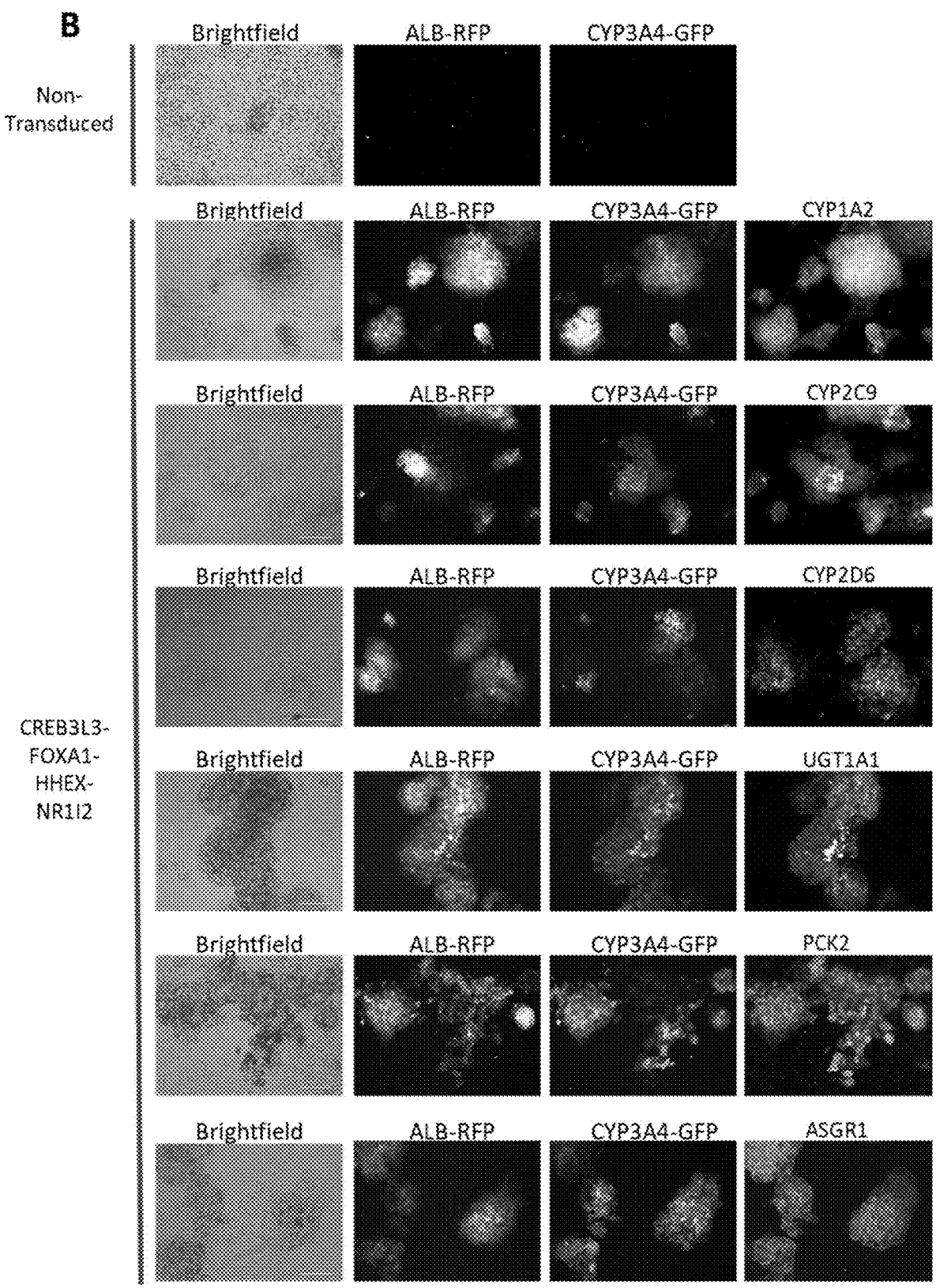
Figure 13:
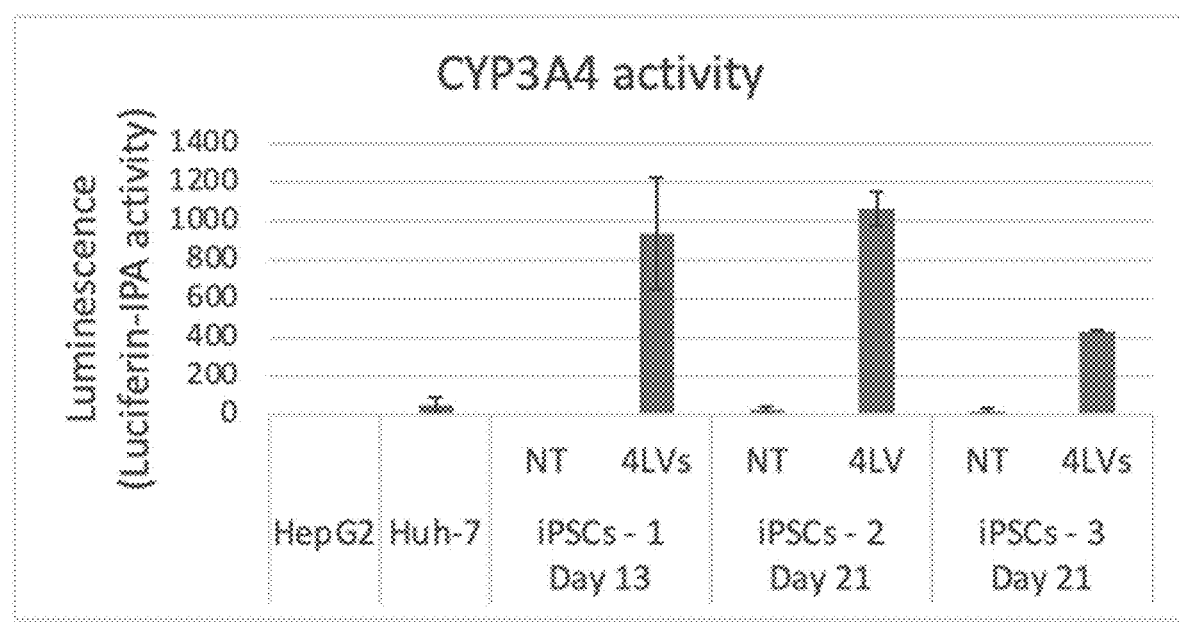

FIG. 13. Combination CREB3L3-FOXA1-NR1I2-HHEX can reprogram iPSCs to hepatocyte-like cells. (A) Live images of reprogrammed cells expressing ALB-RFP and CYP3A4-GFP reporters on day 7 and day 12 of reprogramming. Non-transduced (NT) cells cultured in the same medium in parallel do not express the reporters. (B) Images of fluorescent antibody staining for proteins involved in different hepatocyte-specific functional pathways. The stainings were performed on day 21 of reprogramming for: CYP1A2 (Phase 1 drug metabolism), CYP2C9 (Phase 1 drug metabolism), CYP2D6 (Phase 1 drug metabolism), UGT1A1 (Phase 2 drug metabolism), PCK2 (glucose metabolism), ASGR1 (serum homeostasis)(C) Functional assay for CYP3A4: CYP3A4-GLO assay. Experiment was performed on days 13 and 21 of reprogramming with 2 technical replicates. Reprogrammed cells transduced with lentiviruses expressing the specific 4 TFs (4LVs) and non-transduced controls (NT) were obtained from 3 independent iPSC lines (iPSCs 1-3) and were cultured in parallel. 2 different hepatic cell lines derived from liver tumours, Huh-7 and HepG2 were used as control. Error bars show the standard deviation between replicates.

Figure 14:
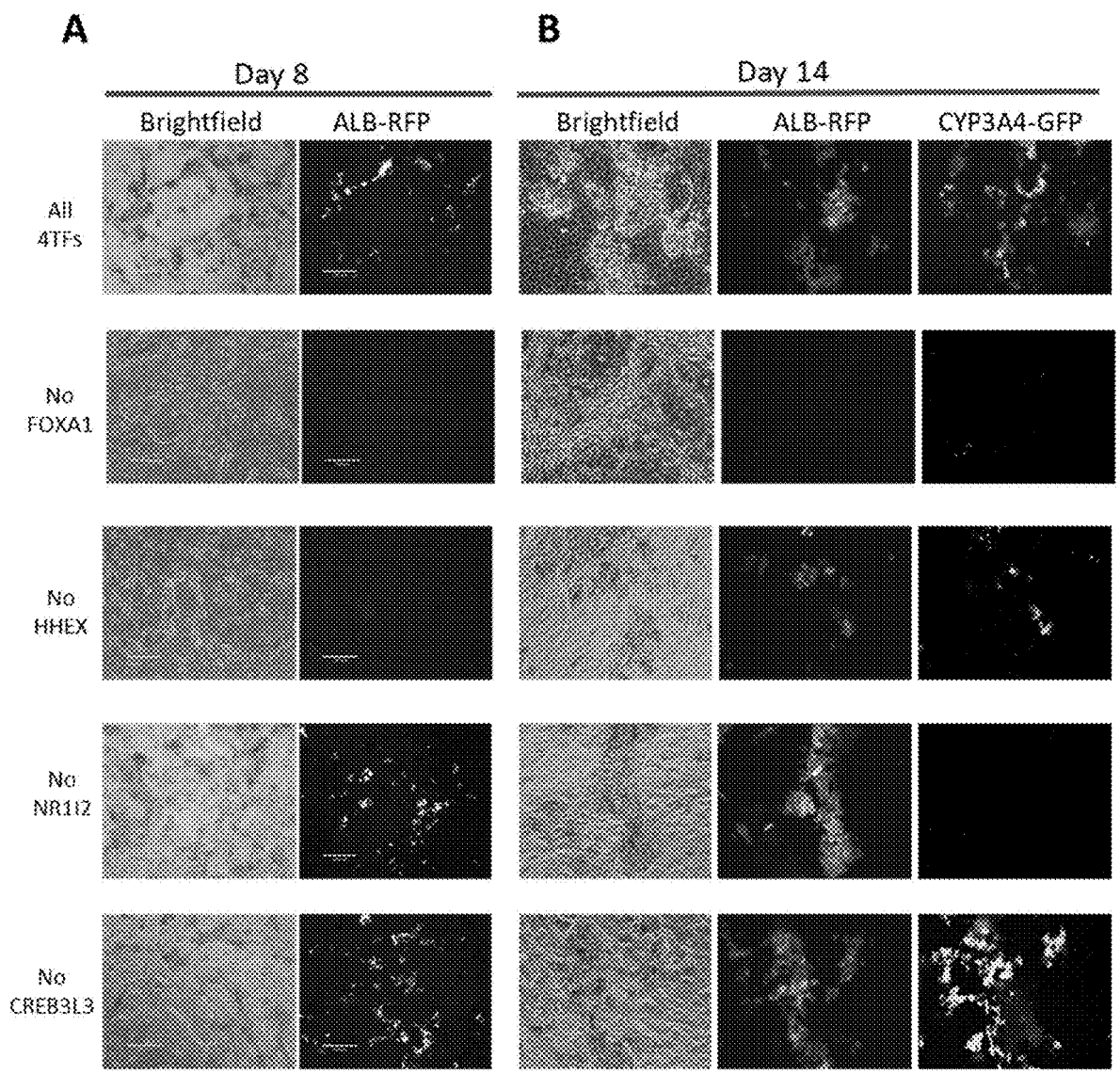

FIG. 14. FOXA1 and HHEX are required for reprogramming to ALB+ hepatic cells and NR1I2 is required for progression from ALB+ to ALB+/CYP3A4+ hepatocyte-like cells. Live images of reprogrammed cells expressing ALB-RFP and CYP3A4-GFP reporters are shown on (A) day 8 and (B) day 14 of reprogramming.

Figure 15:
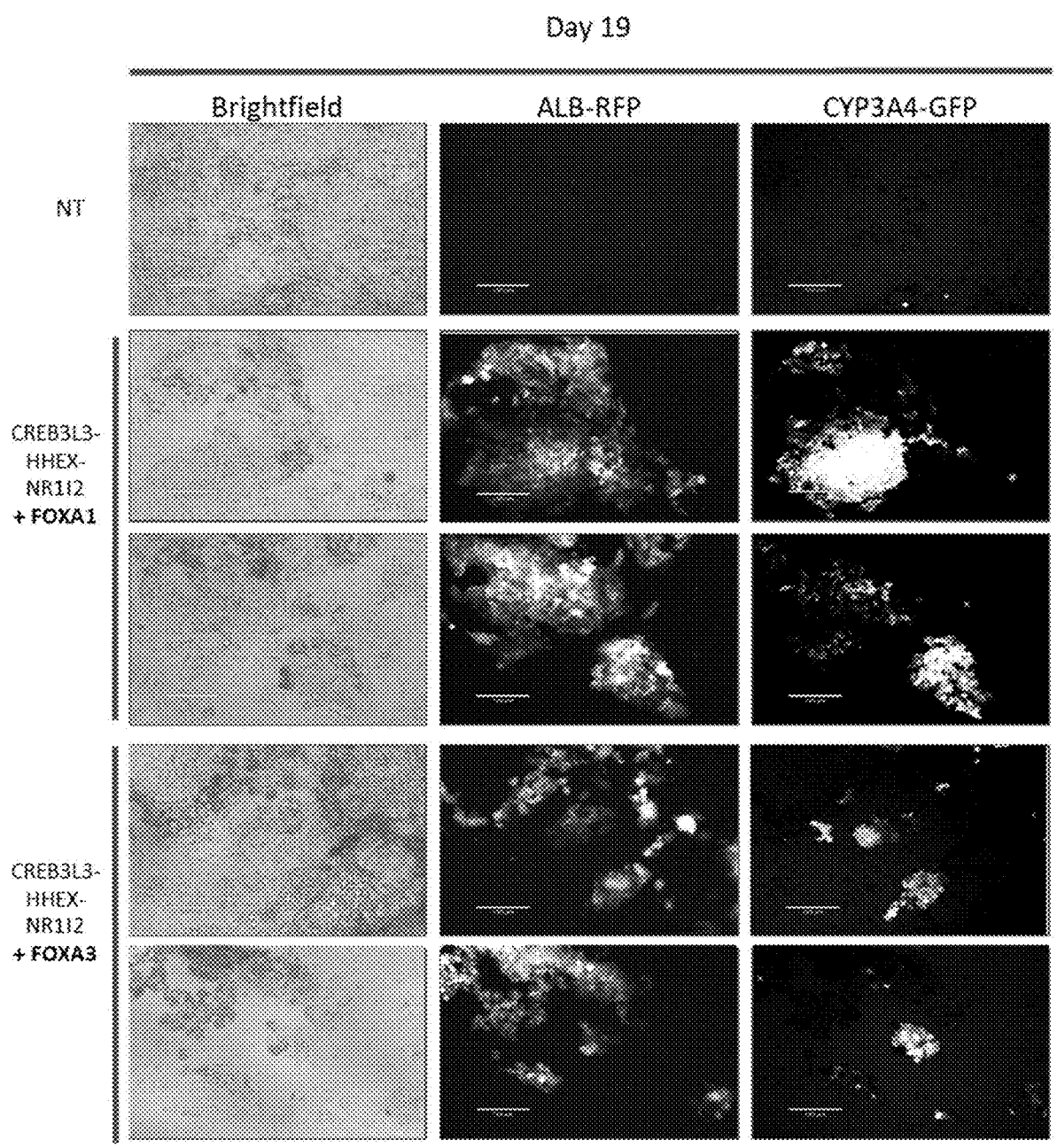

FIG. 15. FOXA3 can replace FOXA1 in reprogramming to ALB+/CYP3A4+ hepatocyte like cells. Live images of reprogrammed cells on day 19 expressing ALB-RFP and CYP3A4-GFP reporters are shown. Non-transduced (NT) cells cultured in the same medium in parallel do not express the reporters.

Figure 16:
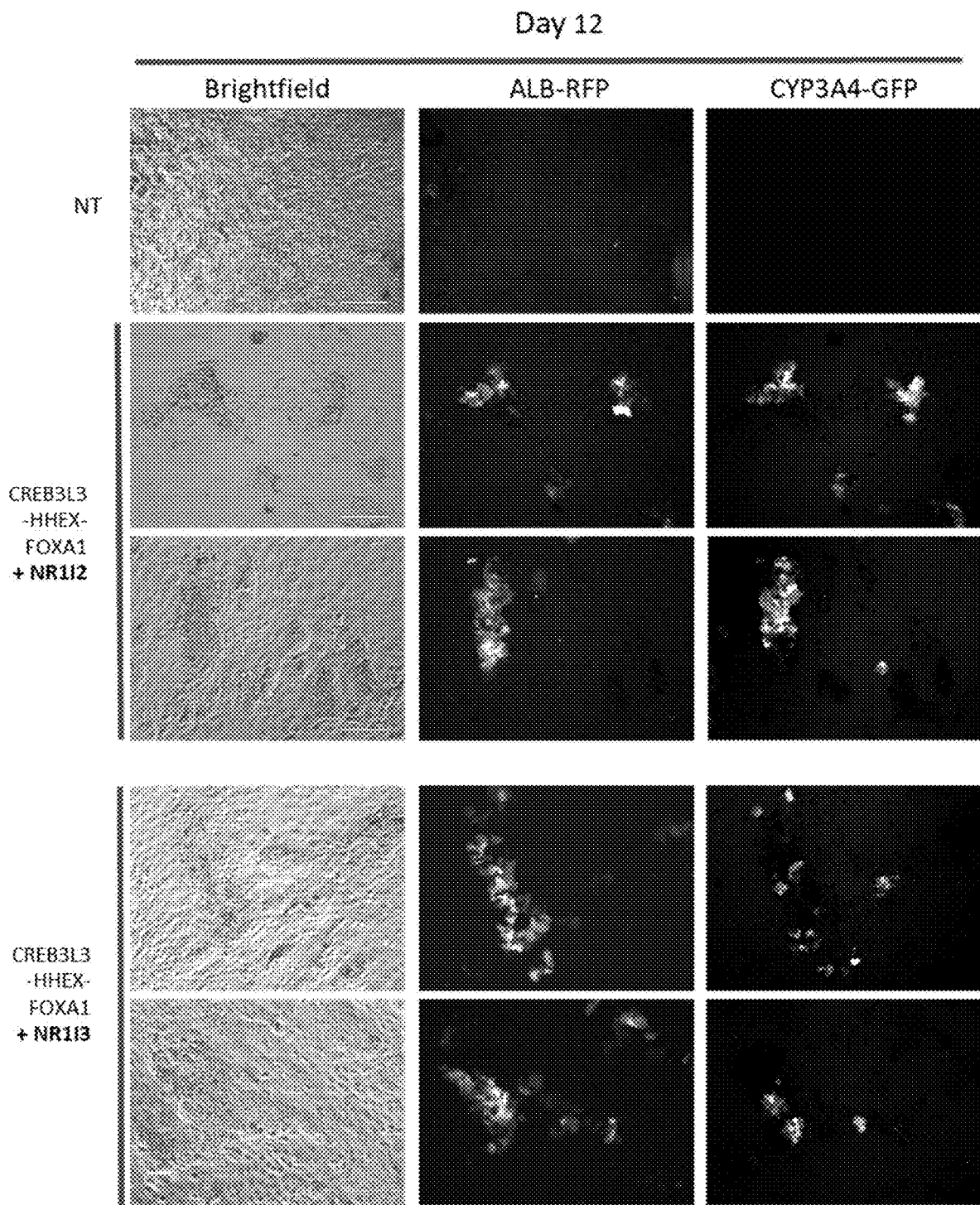

FIG. 16. NR1I3 can replace NR1I2 in reprogramming to ALB+/CYP3A4+ hepatocyte-like cells. Live images of reprogrammed cells on day 13 expressing ALB-RFP and CYP3A4-GFP reporters are shown. Non-transduced (NT) cells cultured in the same medium in parallel do not express the reporters.

DETAILED DESCRIPTION

The present invention provides methods for producing hepatic cells from source cells by increasing the expression of a select group of transcription factors which the present inventors have identified as inducing cell differentiation into hepatic cells.

Definitions

Unless defined otherwise, all technical and scientific terms used herein have the meaning commonly understood by a person skilled in the art to which this invention belongs. As used herein, the following terms have the meanings ascribed to them below.

References to "transcription factor" as used herein, refer to proteins that are involved in gene regulation in both prokaryotic and eukaryotic organisms. In one embodiment, transcription factors can have a positive effect on gene expression and, thus, may be referred to as an "activator" or a "transcriptional activation factor". In another embodiment, a transcription factor can negatively affect gene expression and, thus, may be referred to as "repressors" or a "transcription repression factor". Activators and repressors are generally used terms and their functions may be discerned by those skilled in the art.

The term "increasing the amount of" with respect to increasing an amount of a transcription factor, refers to increasing the quantity of the transcription factor in a cell of interest (e.g., a source cell). In some embodiments, the amount of transcription factor is increased in a cell (e.g., via an expression cassette directing expression of a polynucleotide encoding one or more transcription factors) when the quantity of transcription factor is at least 10%, 20%, 30%, 40%, 50%, 60%, 70%, 80%, 90%, or more relative to a control (e.g., a source cell without said expression cassette(s)). In some of the embodiments, increasing the expression comprises "overexpressing" the transcription factor, i.e., increasing the expression of the transcription factor above the endogenous expression level of the transcription factor in the cell.

Methods of the invention may be used in a "cell population", i.e., a collection of cells which may be differentiated into the desired cell type. Said cell population may comprise "source cells", also referred to as "starting cells", i.e., a cell type prior to differentiation into the desired cell type.

References herein to "pluripotent" refer to cells which have the potential to differentiate into all types of cell found in an organism. One form of pluripotent stem cell, known as induced pluripotent stem cells, are of particular interest to the present invention. "Induced pluripotent stem cells" (iPSCs) are cells that have been reprogrammed to an embryonic stem cell-like state by being forced to express genes and factors important for maintaining the defining properties of embryonic stem cells. In 2006, it was shown that overexpression of four specific transcription factors could convert adult cells into pluripotent stem cells. Oct-3/4 and certain members of the Sox gene family have been identified as potentially crucial transcriptional regulators involved in the induction process. Additional genes including certain members of the Klf family, the Myc family, Nanog, and Lin28, may increase the induction efficiency. Examples of the genes which may be used as reprogramming factors to generate iPSCs include Oct3/4, Sox2, Sox1, Sox3, Sox15, Sox17, Klf4, Klf2, c-Myc, N-Myc, L-Myc, Nanog, Lin28, Fbx15, ERas, ECAT15-2, Tcl1, beta-catenin, Lin28b, Sall4, Esrrb, Tbx3 and Glis1, GATA3, GATA6 and these reprogramming factors may be used singly, or in combination of two or more kinds thereof. In particular, the reprogramming factors may comprise at least the Yamanaka factors, i.e., Oct3/4, Sox2, Klf4 and c-Myc. These reprogramming factors may also be used in combination with the transcription factors of interest in the present invention.

References herein to "somatic" refer to any type of cell that makes up the body of an organism, excluding germ cells. Somatic cells therefore include, for example, skin, heart, muscle, bone or blood cells and their stem cells. In one embodiment, the somatic cell may be an adult cell or a cell derived from an adult which displays one or more detectable characteristics of an adult or non-embryonic cell.

Methods of the invention (e.g., cellular reprogramming of iPSCs) are for use in generating "hepatic cells", which may also be referred to as "hepatocytes". The term "hepatic" as used herein is meant to refer to cells that are related to parenchymal cells of the liver. This term includes hepatocyte-like cells that exhibit some but not all characteristics of adult hepatocytes, as well as mature, fully functional and/or metabolically active adult hepatocyte cells. This term also includes adult and fetal hepatic progenitor cells (including hepatobiliary bipotential progenitors) and fetal hepatocytes. This term includes further cells with the capacity to engraft liver tissue when transplanted in vivo. The hepatic cells produced by this method may be at least as functional as the hepatic cells produced by directed differentiation to date.

References herein to "culturing" include the addition of cells (e.g., the cell population, i.e., the source cells), to media comprising growth factors and/or essential nutrients. It will be appreciated that such culture conditions may be adapted according to the cells or cell population to be generated according to methods of the invention.

References to a "variant" when referring to a polypeptide could be, for example, an amino acid sequence at least 80%, 85%, 90%, 95%, 98%, or 99% identical to the full-length polypeptide. The variant could be a fragment of full-length polypeptide, in particular a functional fragment of the polypeptide. The fragment may be at least 50%, 60%, 70%, 80%, 85%, 90%, 95%, 98%, or 99% as long as the full-length wild type polypeptide or a domain thereof having an activity of interest such as the ability to differentiate a source cell into a hepatic cell. Variations known in the art to eliminate or substantially reduce the activity of the protein are preferably avoided. In some embodiments, the variant lacks an N- and/or C-terminal portion of the full-length polypeptide, e.g., up to 10, 20, or 50 amino acids from either terminus is lacking. In some embodiments, a functional variant or fragment has at least 50%, 60%, 70%, 80%, 90%, 95% or more of the activity of the full-length wild type polypeptide. One of skill in the art will be aware of, or will readily be able to ascertain, whether a particular polypeptide variant or fragment is functional using assays known in the art. For example, the ability of a variant of a transcription factor as listed in Tables 1-4 to generate hepatic cells can be assessed using the assays as described herein.

A "promoter" is a nucleotide sequence which is recognised by proteins involved in initiating and regulating transcription of a polynucleotide. An "inducible promoter" is a nucleotide sequence where expression of a genetic sequence operably linked to the promoter is controlled by an analyte, co-factor, regulatory protein, etc. It is intended that the term "promoter" or "control element" includes full-length promoter regions and functional (e.g., controls transcription or translation) segments of these regions.

The term "operably linked" refers to an arrangement of elements wherein the components so described are configured so as to perform their usual function. Thus, a given promoter operably linked to a genetic sequence is capable of effecting the expression of that sequence when the regulatory factors are present. The promoter need not be contiguous with the sequence, so long as it functions to direct the expression thereof. Thus, for example, intervening untranslated yet transcribed sequences can be present between the promoter sequence and the genetic sequence and the promoter sequence can still be considered "operably linked" to the genetic sequence. Thus, the term "operably linked" is intended to encompass any spacing or orientation of the promoter element and the genetic sequence in the inducible cassette which allows for initiation of transcription of the inducible cassette upon recognition of the promoter element by a transcription complex.

The term "vector", as used herein, is intended to refer to a nucleic acid molecule which is used as a vehicle to carry genetic material into a cell. One type of vector is a "plasmid", which refers to a circular double stranded DNA loop or circle into which additional DNA segments may be ligated. Another type of vector is an infectious but non-pathogenic viral vector, wherein additional DNA segments may be ligated to certain of the viral genetic elements. Certain vectors are capable of autonomous replication in a host cell into which they are introduced (e.g., bacterial vectors having a bacterial origin of replication and episomal mammalian and yeast vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. However, the invention is intended to include such other forms of expression vectors, such as viral vectors (e.g., replication defective retroviruses, lentiviral vectors, adenoviruses, Sendai viruses and adeno-associated viruses), which serve equivalent functions, and also bacteriophage and phagemid systems. Another type of vector includes RNA molecules, e.g., mRNA and stabilised RNA, to carry coding genetic information to the cells.

References to "subject", "patient" or "individual" refer to a subject, in particular a mammalian subject, to be treated. Mammalian subjects include humans, non-human primates, farm animals (such as cows), sports animals, or pet animals, such as dogs, cats, guinea pigs, rabbits, rats or mice. In some embodiments, the subject is a human. In alternative embodiments, the subject is a non-human mammal, such as a mouse.

The term "sufficient amount" means an amount sufficient to produce a desired effect. The term "therapeutically effective amount" is an amount that is effective to ameliorate a symptom of a disease or disorder. A therapeutically effective amount can be a "prophylactically effective amount" as prophylaxis can be considered therapy.

As used herein, the term "about" when used herein includes up to and including 10% greater and up to and including 10% lower than the value specified, suitably up to and including 5% greater and up to and including 5% lower than the value specified, especially the value specified. The term "between" includes the values of the specified boundaries.

It will be understood that any method as described herein may have one or more, or all, steps performed in vitro, ex vivo or in vivo.

Transcription Factors

According to a first aspect of the invention, there is provided a method of generating hepatic cells comprising increasing (or having increased) the expression of at least three or more transcription factors, wherein the three or more transcription factors are selected from the group consisting of: FOXA1 or FOXA3; NR1I2 or NR1I3; HHEX; CREB3L3; GATA4; KLF9; ATF5; MLXIPL; FOXA2; AR; ARID3C; CEBPA; CUX2; EPAS1; HLF; HNF1A; HNF4A; HNF4G; KLF15; NCOA2; NR0B2; NR1H4; NR5A2; ONECUT1; ONECUT2; PPARA; PROX1; RORA; RORC; RXRA; SALL1; SMAD1; SREBF1; STAT3; TSHZ2; XBP1; ZBTB16; and variants thereof, in a non-hepatic cell population and culturing (or having cultured) the cell population to obtain hepatic cells.

According to a another aspect of the invention, there is provided a method of generating hepatic cells comprising increasing the protein expression of one or more transcription factors selected from the group consisting of: AR, ARID3C, ATF5, CEBPA, CREB3L3, CUX2, EPAS1, FOXA1, FOXA2, FOXA3, GATA4, HHEX, HLF, HNF1A, HNF4A, HNF4G, KLF15, KLF9, MLXIPL, NCOA2, NR0B2, NR1H4, NR1I2, NR1I3, NR5A2, ONECUT1, ONECUT2, PPARA, PROX1, RORA, RORC, RXRA, SALL1, SMAD1, SREBF1, STAT3, TSHZ2, XBP1, ZBTB16, and variants thereof, in a cell population and culturing the cell population to obtain hepatic cells.

The method may comprise increasing the expression (in particular, the protein expression) of a sufficient number of the transcription factors (e.g., as listed in Tables 1, 2, 3 and 4 and variants and isoforms thereof) capable of causing differentiation of a cell population to hepatic cells, therefore differentiating the cell population into hepatic cells. In the context of the present invention, these factors may also be referred to as "reprogramming factors". As described herein, the expression of an exogenous or endogenous (in particular an exogenous) transcription factor may be increased.

In one embodiment, the (e.g., at least one or more, such as at least three or more) transcription factors are selected from the group consisting of: AR, ARID3C, ATF5, CEBPA, CREB3L3, CUX2, EPAS1, FOXA1, FOXA2, FOXA3, GATA4, HHEX, HLF, HNF1A, HNF4A, HNF4G, KLF15, KLF9, MLXIPL, NCOA2, NR0B2, NR1H4, NR1I2, NR1I3, NR5A2, ONECUT1, ONECUT2, PPARA, PROX1, RORA, RORC, RXRA, SALL1, SMAD1, SREBF1, STAT3, TSHZ2, XBP1, ZBTB16, and variants thereof, wherein the expression of at least one of AR, ATF5, CEBPA, CREB3L3, EPAS1, FOXA1, FOXA2, FOXA3, GATA4, HHEX, HLF, HNF1A, HNF4A, HNF4G, KLF15, KLF9, MLXIPL, NCOA2, NR1H4, NR1I2, NR1I3, NR5A2, ONECUT1, PPARA, PROX1, RORA, RORC, RXRA, SMAD1, SREBF1, STAT3, TSHZ2, XBP1, ZBTB16, and variants thereof is increased, in particular where the expression of at least one of ATF5, CREB3L3, FOXA1, FOXA2, FOXA3, GATA4, HHEX, HNF4A, HNF4G, KLF9, MLXIPL, NR1I2, NR1I3, ONECUT1, RXRA, SREBF1, and variants thereof is increased.

In one embodiment, the method comprises increasing the expression of two or more transcription factors, in particular three or more, four or more, five or more, and six or more, selected from the group consisting of: AR, ARID3C, ATF5, CEBPA, CREB3L3, CUX2, EPAS1, FOXA1, FOXA2, FOXA3, GATA4, HHEX, HLF, HNF1A, HNF4A, HNF4G, KLF15, KLF9, MLXIPL, NCOA2, NR0B2, NR1H4, NR1I2, NR1I3, NR5A2, ONECUT1, ONECUT2, PPARA, PROX1, RORA, RORC, RXRA, SALL1, SMAD1, SREBF1, STAT3, TSHZ2, XBP1, ZBTB16, and variants thereof.

In one embodiment, the (e.g., at least one or more, such as at least three or more) transcription factors are selected from the group consisting of: AR, ATF5, CEBPA, CREB3L3, EPAS1, FOXA1, FOXA2, FOXA3, GATA4, HHEX, HLF, HNF1A, HNF4A, HNF4G, KLF15, KLF9, MLXIPL, NCOA2, NR1H4, NR1I2, NR1I3, NR5A2, ONECUT1, PPARA, PROX1, RORA, RORC, RXRA, SMAD1, SREBF1, STAT3, TSHZ2, XBP1, ZBTB16, and variants thereof.

In one embodiment, the method comprises increasing the expression of two or more transcription factors, in particular three or more, four or more, five or more, six or more, selected from the group consisting of: AR, ATF5, CEBPA, CREB3L3, EPAS1, FOXA1, FOXA2, FOXA3, GATA4, HHEX, HLF, HNF1A, HNF4A, HNF4G, KLF15, KLF9, MLXIPL, NCOA2, NR1H4, NR1I2, NR1I3, NR5A2, ONECUT1, PPARA, PROX1, RORA, RORC, RXRA, SMAD1, SREBF1, STAT3, TSHZ2, XBP1, ZBTB16, and variants thereof.

In one embodiment, the (e.g., at least one or more, such as at least three or more) transcription factors are selected from the group consisting of: ATF5, ARID3C, CREB3L3, CUX2, FOXA1, FOXA2, FOXA3, GATA4, HHEX, HNF4A, HNF4G, KLF9, MLXIPL, NR0B2, NR1I2, NR1I3, ONECUT1, ONECUT2, RXRA, SALL1, SREBF1, and variants thereof.

In one embodiment, the method comprises increasing the expression of two or more transcription factors, in particular three or more, four or more, five or more and six or more, selected from the group consisting of: ATF5, ARID3C, CREB3L3, CUX2, FOXA1, FOXA2, FOXA3, GATA4, HHEX, HNF4A, HNF4G, KLF9, MLXIPL, NR0B2, NR1I2, NR1I3, ONECUT1, ONECUT2, RXRA, SALL1, SREBF1, and variants thereof.

In one embodiment, the (e.g., at least one or more, such as at least three or more) transcription factors are selected from the group consisting of: ATF5, CREB3L3, FOXA1, FOXA2, FOXA3, GATA4, HHEX, HNF4A, HNF4G, KLF9, MLXIPL, NR1I2, NR1I3, ONECUT1, RXRA, SREBF1, and variants thereof.

In one embodiment, the method comprises increasing the expression of two or more transcription factors, in particular three or more, four or more, five or more and six or more, selected from the group consisting of: ATF5, CREB3L3, FOXA1, FOXA2, FOXA3, GATA4, HHEX, HNF4A, HNF4G, KLF9, MLXIPL, NR1I2, NR1I3, ONECUT1, RXRA, SREBF1, and variants thereof.

In one embodiment, the (e.g., at least one or more, such as at least three or more) transcription factors are selected from the group consisting of: ATF5, CREB3L3, FOXA1, FOXA2, FOXA3, GATA4, HHEX, HNF4A, KLF9, MLXIPL, NR1I2, NR1I3, RXRA, SREBF1, and variants thereof.

In one embodiment, the (e.g., at least one or more, such as at least three or more) transcription factors are selected from the group consisting of: ATF5, CREB3L3, FOXA1, FOXA2, FOXA3, GATA4, HHEX, KLF9, MLXIPL, NR1I2, NR1I3, and variants thereof.

In one embodiment, the transcription factor comprises FOXA1. FOXA1 may be used in combination with one or more, such as one, two, three, four, or five transcription factors selected from the list in Tables 1, 2, 3 or 4. In a further embodiment, the method comprises increasing the expression of between two and six transcription factors selected from FOXA1 in combination with ATF5, CREB3L3, FOXA2, FOXA3, GATA4, HHEX, HNF4A, HNF4G, KLF9, MLXIPL, NR1I2, NR1I3, ONECUT1, RXRA, SREBF1, or variants thereof.

In one embodiment, the transcription factor comprises CREB3L3. CREB3L3 may be used in combination with one or more, such as one, two, three, four, or five transcription factors selected from the list in Tables 1, 2, 3 or 4. In a further embodiment, the method comprises increasing the expression of between two and six transcription factors selected from CREB3L3 in combination with ATF5, FOXA1, FOXA2, FOXA3, GATA4, HHEX, HNF4A, HNF4G, KLF9, MLXIPL, NR1I2, NR1I3, ONECUT1, RXRA, SREBF1, or variants thereof.

In one embodiment, the method comprises increasing the expression of FOXA1 and CREB3L3 in combination with one, two, three, or four (in particular one or two) transcription factors selected from the list in Tables 1, 2, 3 or 4. In a further embodiment, FOXA1 and CREB3L3 are used in combination with one or two transcription factors selected from the list consisting of: ATF5, FOXA2, FOXA3, GATA4, HHEX, HNF4A, HNF4G, KLF9, MLXIPL, NR1I2, NR1I3, ONECUT1, RXRA, SREBF1, or variants thereof, in particular in combination with HHEX, HNF4G, KLF9, MLXIPL, RXRA, SREBF1, or variants thereof.

In one embodiment, the transcription factor comprises HHEX. HHEX may be used in combination with one or more, such as one, two, three, four, or five transcription factors selected from the list in Tables 1, 2, 3 or 4. In a further embodiment, the method comprises increasing the expression of between two and six transcription factors selected from HHEX in combination with ATF5, CREB3L3, FOXA1, FOXA2, FOXA3, GATA4, HNF4A, HNF4G, KLF9, MLXIPL, NR1I2, NR1I3, ONECUT1, RXRA, SREBF1, or variants thereof.

In one embodiment, the method comprises increasing the expression of FOXA1 and HHEX in combination with one, two, three or four (in particular one or two) transcription factors selected from the list in Tables 1, 2, 3 or 4. In a further embodiment, FOXA1 and HHEX are used in combination with one or two transcription factors selected from the list consisting of: ATF5, CREB3L3, FOXA2, FOXA3, GATA4, HNF4A, HNF4G, KLF9, MLXIPL, NR1I2, NR1I3, ONECUT1, RXRA, SREBF1, or variants thereof, in particular in combination with CREB3L3, HNF4G, KLF9, MLXIPL, RXRA, SREBF1, or variants thereof.

In one embodiment, the method comprises increasing the expression of FOXA1, CREB3L3 and HHEX in combination with one, two, three or four (in particular one) transcription factors selected from the list in Tables 1, 2, 3 or 4. In a further embodiment, FOXA1, CREB3L3 and HHEX are used in combination with a transcription factors selected from the list consisting of: ATF5, FOXA2, FOXA3, GATA4, HNF4A, HNF4G, KLF9, MLXIPL, NR1I2, NR1I3, ONECUT1, RXRA, SREBF1, or variants thereof, in particular in combination with HNF4G, KLF9, MLXIPL, RXRA, SREBF1, or variants thereof.

In one embodiment, the transcription factor comprises NR1I2. NR1I2 may be used in combination with one or more, such as one, two, three, four or five, transcription factors selected from the list in Tables 1, 2, 3 or 4. In a further embodiment, the method comprises increasing the expression of between two and six transcription factors selected from NR1I2 in combination with ATF5, CREB3L3, FOXA1, FOXA2, FOXA3, GATA4, HHEX, HNF4A, HNF4G, KLF9, MLXIPL, NR1I3, ONECUT1, RXRA, SREBF1, or variants thereof.

In one embodiment, the transcription factor comprises FOXA3. FOXA3 may be used in combination with one or more, such as one, two, three, four or five, transcription factors selected from the list in Tables 1, 2, 3 or 4. In a further embodiment, the method comprises increasing the expression of between two and six transcription factors selected from FOXA3 in combination with ATF5, CREB3L3, FOXA1, FOXA2, GATA4, HHEX, HNF4A, HNF4G, KLF9, MLXIPL, NR1I2, NR1I3, ONECUT1, RXRA, SREBF1, or variants thereof.

In one embodiment, the transcription factor comprises NR1I3. NR1I3 may be used in combination with one or more, such as one, two, three, four or five transcription factors selected from the list in Tables 1, 2, 3 or 4. In a further embodiment, the method comprises increasing the expression of between two and six transcription factors selected from NR1I3 in combination with ATF5, CREB3L3, FOXA1, FOXA2, FOXA3, GATA4, HHEX, HNF4A, HNF4G, KLF9, MLXIPL, NR1I2, ONECUT1, RXRA, SREBF1, or variants thereof.

In one embodiment, the three or more transcription factors are selected from: FOXA1, FOXA2, FOXA3, CREB3L3, HHEX, NR1I2, NR1I3, or variants thereof.

The present inventors have shown herein that the FOXA factors (also known as the HNF3 subfamily of transcription factors) may be used interchangeably. Therefore in one embodiment, the three or more transcription factors are selected from: FOXA1, FOXA2 or FOXA3, in combination with two or more transcription factors selected from the group consisting of: NR1I2; NR1I3; HHEX; CREB3L3; GATA4; KLF9; ATF5; MLXIPL; AR; ARID3C; CEBPA; CUX2; EPAS1; HLF; HNF1A; HNF4A; HNF4G; KLF15; NCOA2; NR0B2; NR1H4; NR5A2; ONECUT1; ONECUT2; PPARA; PROX1; RORA; RORC; RXRA; SALL1; SMAD1; SREBF1; STAT3; TSHZ2; XBP1; ZBTB16; and variants thereof. In a further embodiment, the three or more transcription factors are selected from: FOXA1, FOXA2 or FOXA3; CREB3L3; HHEX; NR1I2; NR1I3; or variants thereof.

Furthermore, the factors NR1I2 and NR1I3 (members of the Nuclear Receptor Subfamily 1 Group I family) may also be used interchangeably. Therefore in a further embodiment, the three or more transcription factors are selected from: NR1I2 or NR1I3, in combination with two or more transcription factors selected from the group consisting of: FOXA1; FOXA2; FOXA3; CREB3L3; HHEX; GATA4; KLF9; ATF5; MLXIPL; AR; ARID3C; CEBPA; CUX2; EPAS1; HLF; HNF1A; HNF4A; HNF4G; KLF15; NCOA2; NR0B2; NR1H4; NR5A2; ONECUT1; ONECUT2; PPARA; PROX1; RORA; RORC; RXRA; SALL1; SMAD1; SREBF1; STAT3; TSHZ2; XBP1; ZBTB16; and variants thereof. In a further embodiment, the three or more transcription factors are selected from: NR1I2 or NR1I3; FOXA1; FOXA2; FOXA3; CREB3L3; HHEX; or variants thereof.

According to a further aspect of the invention, there is provided a method of generating hepatic cells comprising increasing the expression of at least three or more transcription factors wherein the three or more transcription factors are selected from:
(a) FOXA1, FOXA2 or FOXA3;
(b) NR1I2 or NR1I3; and
(c) at least one or more additional transcription factors selected from the group consisting of: HHEX; CREB3L3; GATA4; KLF9; ATF5; MLXIPL; FOXA2; AR; ARID3C; CEBPA; CUX2; EPAS1; HLF; HNF1A; HNF4A; HNF4G; KLF15; NCOA2; NR0B2; NR1H4; NR5A2; ONECUT1; ONECUT2; PPARA; PROX1; RORA; RORC; RXRA; SALL1; SMAD1; SREBF1; STAT3; TSHZ2; XBP1; ZBTB16; and variants thereof,
in a (non-hepatic) cell population and culturing the cell population to obtain hepatic cells.

In a one embodiment, the transcription factors comprise: (i) FOXA1, FOXA2 or FOXA3, (ii) CREB3L3 and (iii) NR1I2 or NR1I3. In a further embodiment, the transcription factors comprise FOXA1, CREB3L3 and NR1I2.

In one embodiment, the transcription factors comprise: (i) FOXA1, FOXA2 or FOXA3, (ii) HHEX and (iii) NR1I2 or NR1I3. In a further embodiment, the transcription factors comprise FOXA1, HHEX and NR1I2.

In one embodiment, the transcription factors comprise: (i) FOXA1, FOXA2 or FOXA3, (ii) CREB3L3, (iii) HHEX and (iv) NR1I2 or NR1I3. In a further embodiment, the method comprises increasing the expression of FOXA1, CREB3L3, NR1I2 and HHEX. Therefore, according to another aspect of the invention, there is provided a method of generating hepatic cells comprising increasing the expression of (i) FOXA1, FOXA2 or FOXA3, (ii) CREB3L3, (iii) HHEX and (iv) NR1I2 or NR1I3 in a non-hepatic cell population and culturing the cell population to obtain hepatic cells. According to a further aspect of the invention, there is provided a method of generating hepatic cells comprising increasing the expression of FOXA1, CREB3L3, NR1I2 and HHEX in a non-hepatic cell population and culturing the cell population to obtain hepatic cells.

In one embodiment, the transcription factor comprises GATA4. GATA4 may be used in combination with one or more, such as one, two, three, four or five, transcription factors selected from the list in Tables 1, 2, 3 or 4. In a further embodiment, the method comprises increasing the expression of between two and six transcription factors selected from GATA4 in combination with ATF5, CREB3L3, FOXA1, FOXA2, FOXA3, HHEX, HNF4A, HNF4G, KLF9, MLXIPL, NR1I2, NR1I3, ONECUT1, RXRA, SREBF1, or variants thereof.

In one embodiment, the transcription factor comprises HNF4A. HNF4A may be used in combination with one or more, such as one, two, three, four or five, transcription factors selected from the list in Tables 1, 2, 3 or 4. In a further embodiment, the method comprises increasing the expression of between two and six transcription factors selected from HNF4A in combination with ATF5, CREB3L3, FOXA1, FOXA2, FOXA3, GATA4, HHEX, HNF4G, KLF9, MLXIPL, NR1I2, NR1I3, ONECUT1, RXRA, SREBF1, or variants thereof.

In one embodiment, the transcription factor comprises ATF5. ATF5 may be used in combination with one or more, such as one, two, three, four or five, transcription factors selected from the list in Tables 1, 2, 3 or 4. In a further embodiment, the method comprises increasing the expression of between two and six transcription factors selected from ATF5 in combination with CREB3L3, FOXA1, FOXA2, FOXA3, GATA4, HHEX, HNF4A, HNF4G, KLF9, MLXIPL, NR1I2, NR1I3, ONECUT1, RXRA, SREBF1, or variants thereof.

In one embodiment, the transcription factor comprises MLXIPL. MLXIPL may be used in combination with one or more, such as one, two, three, four or five, transcription factors selected from the list in Tables 1, 2, 3 or 4. In a further embodiment, the method comprises increasing the expression of between two and six transcription factors selected from MLXIPL in combination with ATF5, CREB3L3, FOXA1, FOXA2, FOXA3, GATA4, HHEX, HNF4A, HNF4G, KLF9, NR1I2, NR1I3, ONECUT1, RXRA, SREBF1, or variants thereof.

In one embodiment, the transcription factor comprises KLF9. KLF9 may be used in combination with one or more, such as one, two, three, four or five, transcription factors selected from the list in Tables 1, 2, 3 or 4. In a further embodiment, the method comprises increasing the expression of between two and six transcription factors selected from KLF9 in combination with ATF5, CREB3L3, FOXA1, FOXA2, FOXA3, GATA4, HHEX, HNF4A, HNF4G, MLXIPL, NR1I2, NR1I3, ONECUT1, RXRA, SREBF1, or variants thereof.

In one embodiment, the transcription factor comprises RXRA. RXRA may be used in combination with one or more, such as one, two, three, four or five, transcription factors selected from the list in Tables 1, 2, 3 or 4. In a further embodiment, the method comprises increasing the expression of between two and six transcription factors selected from RXRA in combination with ATF5, CREB3L3, FOXA1, FOXA2, FOXA3, GATA4, HHEX, HNF4A, HNF4G, KLF9, MLXIPL, NR1I2, NR1I3, ONECUT1, SREBF1, or variants thereof.

In one embodiment, the transcription factor comprises FOXA2. FOXA2 may be used in combination with one or more, such as one, two, three, four or five, transcription factors selected from the list in Tables 1, 2, 3 or 4. In a further embodiment, the method comprises increasing the expression of between two and six transcription factors selected from FOXA2 in combination with ATF5, CREB3L3, FOXA1, FOXA3, GATA4, HHEX, HNF4A, HNF4G, KLF9, MLXIPL, NR1I2, NR1I3, ONECUT1, RXRA, SREBF1, or variants thereof.

In one embodiment, the transcription factor comprises SREBF1. SREBF1 may be used in combination with one or more, such as one, two, three, four or five, transcription factors selected from the list in Tables 1, 2, 3 or 4. In a further embodiment, the method comprises increasing the expression of between two and six transcription factors selected from SREBF1 in combination with ATF5, CREB3L3, FOXA1, FOXA2, FOXA3, GATA4, HHEX, HNF4A, HNF4G, KLF9, MLXIPL, NR1I2, NR1I3, ONECUT1, RXRA, or variants thereof.

In one embodiment, the transcription factor comprises ONECUT1. ONECUT1 may be used in combination with one or more, such as one, two, three, four or five, transcription factors selected from the list in Tables 1, 2, 3 or 4. In a further embodiment, the method comprises increasing the expression of between two and six transcription factors selected from ONECUT1 in combination with ATF5, CREB3L3, FOXA1, FOXA2, FOXA3, GATA4, HHEX, HNF4A, HNF4G, KLF9, MLXIPL, NR1I2, NR1I3, RXRA, SREBF1, or variants thereof.

In one embodiment, the transcription factor comprises HNF4G. HNF4G may be used in combination with one or more, such as one, two, three, four or five, transcription factors selected from the list in Tables 1, 2, 3 or 4. In a further embodiment, the method comprises increasing the expression of between two and six transcription factors selected from HNF4G in combination with ATF5, CREB3L3, FOXA1, FOXA2, FOXA3, GATA4, HHEX, HNF4A, KLF9, MLXIPL, NR1I2, NR1I3, ONECUT1, RXRA, SREBF1, or variants thereof.

In one embodiment, the method comprises increasing the expression of two or more transcription factors, in particular three or more, four or more, five or more and six or more, selected from the group consisting of: ATF5, CREB3L3, FOXA1, FOXA2, FOXA3, GATA4, HHEX, HNF4A, KLF9, MLXIPL, NR1I2, NR1I3, RXRA, SREBF1, and variants thereof.

In one embodiment, the transcription factors are selected from the group consisting of AR, ARID3C, CUX2, EPAS1, FOXA3, HNF4G, KLF15, KLF9, MLXIPL, NCOA2, ONECUT2, PPARA, RORA, RORC, RXRA, SALL1, SMAD1, SREBF1, STAT3, TSHZ2, XBP1, ZBTB16, and variants thereof. In a further embodiment, the transcription factors are selected from the group consisting of: AR, ARID3C, CUX2, EPAS1, HNF4G, KLF15, KLF9, MLXIPL, NCOA2, ONECUT2, PPARA, RORA, RORC, RXRA, SALL1, SMAD1, SREBF1, STAT3, TSHZ2, XBP1, ZBTB16, and variants thereof. In a yet further embodiment, the transcription factors are selected from the group consisting of: AR, ARID3C, CUX2, EPAS1, HNF4G, KLF15, KLF9, MLXIPL, NCOA2, RORA, RORC, RXRA, SALL1, SMAD1, SREBF1, STAT3, TSHZ2, XBP1, ZBTB16, and variants thereof.

In one embodiment, the transcription factors are selected from the group consisting of: AR, EPAS1, FOXA3, HNF4G, KLF15, KLF9, MLXIPL, NCOA2, PPARA, RORA, RORC, RXRA, SMAD1, SREBF1, STAT3, TSHZ2, XBP1, ZBTB16, and variants thereof. In a further embodiment, the transcription factors are selected from the group consisting of: AR, EPAS1, HNF4G, KLF15, KLF9, MLXIPL, NCOA2, PPARA, RORA, RORC, RXRA, SMAD1, SREBF1, STAT3, TSHZ2, XBP1, ZBTB16, and variants thereof. In a yet further embodiment, the transcription factors are selected from the group consisting of: AR, EPAS1, HNF4G, KLF15, KLF9, MLXIPL, NCOA2, RORA, RORC, RXRA, SMAD1, SREBF1, STAT3, TSHZ2, XBP1, ZBTB16, and variants thereof.

In one embodiment, the transcription factors are selected from the group consisting of: FOXA3, HNF4G, KLF9, MLXIPL, RXRA, SREBF1, and variants thereof. In a further embodiment, the transcription factors are selected from the group consisting of: HNF4G, KLF9, MLXIPL, RXRA, SREBF1, and variants thereof.

In one embodiment, the expression of at least one of ARID3C, CUX2, HNF4G, KLF9, MLXIPL, RXRA, SALL1, or SREBF1 is increased, preferably in combination with one or more transcription factors selected from the group consisting of: ATF5, CREB3L3, FOXA1, FOXA2, FOXA3, GATA4, HHEX, HNF4A, NR0B2, NR1I2, NR1I3, ONECUT1, ONECUT2, and variants thereof.

In one embodiment, the expression of at least one of HNF4G, KLF9, MLXIPL, RXRA, or SREBF1 is increased, preferably in combination with one or more transcription factors selected from the group consisting of: ATF5, CREB3L3, FOXA1, FOXA2, FOXA3, GATA4, HHEX, HNF4A, NR1I2, NR1I3, ONECUT1, and variants thereof.

In one embodiment, the expression of at least one of KLF9, MLXIPL, RXRA, or SREBF1 is increased, preferably in combination with one or more transcription factors selected from the group consisting of: ATF5, CREB3L3, FOXA1, FOXA2, FOXA3, GATA4, HHEX, HNF4A, NR1I2, NR1I3, and variants thereof.

As shown by the data presented herein (see, for example, Tables 5 and 6 of FIG. 12), multiple combinations comprising at least three or four of the transcription factors listed in Tables 1, 2, 3 and 4 were present in the cells reprogrammed as adult hepatocytes. Therefore, in one embodiment, the transcription factors used in the methods of the invention comprise one of the combinations listed in Tables 5 and 6.

Methods of the invention encompass the use of variants of the transcription factors of interest (i.e., as described in Tables 1, 2, 3 and 4). References to the transcription factors also encompasses species variants, homologues, allelic forms, mutant forms, and equivalents thereof, including conservative substitutions, additions, deletions therein not adversely affecting the structure of function. Changes in the nucleic acid sequence of the transcription factor gene can result in conservative changes or substitutions in the amino acid sequence. Therefore, the invention includes polypeptides having conservative changes or substitutions. The invention includes sequences where conservative substitutions are made that do not alter the activity of the transcription factor protein of interest.

TABLE 1

Transcription factors for generation of hepatic cells, including accession numbers (as accessed on 11 Mar. 2020)

| Transcription Factor Gene name | Ensembl Gene ID |
| --- | --- |
| AR | ENSG00000169083 |
| ARID3C | ENSG00000205143 |
| ATF5 | ENSG00000169136 |
| CEBPA | ENSG00000245848 |
| CREB3L3 | ENSG00000060566 |
| CUX2 | ENSG00000111249 |
| EPAS1 | ENSG00000116016 |
| FOXA1 | ENSG00000129514 |
| FOXA2 | ENSG00000125798 |
| FOXA3 | ENSG00000170608 |
| GATA4 | ENSG00000136574 |
| HHEX | ENSG00000152804 |
| HLF | ENSG00000108924 |
| HNF1A | ENSG00000135100 |
| HNF4A | ENSG00000101076 |
| HNF4G | ENSG00000164749 |
| KLF15 | ENSG00000163884 |
| KLF9 | ENSG00000119138 |
| MLXIPL | ENSG00000009950 |
| NCOA2 | ENSG00000140396 |
| NR0B2 | ENSG00000131910 |
| NR1H4 | ENSG00000012504 |
| NR1I2 | ENSG00000144852 |
| NR1I3 | ENSG00000143257 |
| NR5A2 | ENSG00000116833 |
| ONECUT1 | ENSG00000169856 |
| ONECUT2 | ENSG00000119547 |
| PPARA | ENSG00000186951 |
| PROX1 | ENSG00000117707 |
| RORA | ENSG00000069667 |
| RORC | ENSG00000143365 |
| RXRA | ENSG00000186350 |
| SALL1 | ENSG00000103449 |
| SMAD1 | ENSG00000170365 |
| SREBF1 | ENSG00000072310 |
| STAT3 | ENSG00000168610 |
| TSHZ2 | ENSG00000182463 |
| XBP1 | ENSG00000100219 |
| ZBTB16 | ENSG00000109906 |

The transcription factors described in Table 1 are shown in the examples presented herein to induce source cells to differentiate into hepatic cells. Different combinations of the transcription factors may be used. For example, one, two, three, four, five, six, seven, eight, nine, ten, or more of the genes as listed in Table 1 (and isoforms or variants thereof) may be used in methods of the invention. In a further embodiment, the transcription factors used may be selected from Tables 2, 3 or 4 (and isoforms or variants thereof). Many of these genes have different isoforms, which might have similar functions and therefore are contemplated for use in the invention.

In one embodiment, the method comprises increasing the expression of two or more of the transcription factors, in particular three, four, five or six or more of the transcription factors. Preferably, the method comprises increasing the expression of three or more of the transcription factors. More preferably, the method comprises increasing the expression of four or more of the transcription factors.

In one embodiment, the method comprises increasing the expression of between three and eight of the transcription factors, such as between four and seven of the transcription factors, in particular four or five of the transcription factors. In one embodiment, the method comprises increasing the expression of two to eight of the transcription factors, in particular three to six or three to five of the transcription factors. In one embodiment, the method comprises increasing the expression of two of the transcription factors, three of the transcription factors, four of the transcription factors, five of the transcription factors or six of the transcription factors.

The method may comprise introducing into a source cell a nucleic acid or protein preparation which encodes or provides a combination of transcription factors as described herein, and culturing the cell under conditions suitable for reprogramming the cell into a hepatic cell.

According to one aspect, there is provided a method of producing hepatic cells from source cells comprises inducing increased expression of a gene encoding one of more of the transcription factors described herein (e.g., as listed in Table 1), wherein the source cells differentiate to form hepatic cells.

In one embodiment, the gene is induced to express the gene at levels greater than the expression levels endogenous to the source cell.

In one embodiment, the method comprises generating hepatic cells by cellular reprogramming of pluripotent stem cells (in particular induced pluripotent stem cells).

According to a further aspect of the invention, there is provided a use of one or more transcription factors selected from the group consisting of: AR, ARID3C, ATF5, CEBPA, CREB3L3, CUX2, EPAS1, FOXA1, FOXA2, FOXA3, GATA4, HHEX, HLF, HNF1A, HNF4A, HNF4G, KLF15, KLF9, MLXIPL, NCOA2, NR0B2, NR1H4, NR1I2, NR1I3, NR5A2, ONECUT1, ONECUT2, PPARA, PROX1, RORA, RORC, RXRA, SALL1, SMAD1, SREBF1, STAT3, TSHZ2, XBP1, ZBTB16 and variants thereof, to generate hepatic cells. According to a further aspect of the invention, there is provided a use of at least three or more transcription factors wherein the three or more transcription factors are selected from the group consisting of: FOXA1 or FOXA3; NR1I2 or NR1I3; HHEX; CREB3L3; GATA4; KLF9; ATF5; MLXIPL; FOXA2; AR; ARID3C; CEBPA; CUX2; EPAS1; HLF; HNF1A; HNF4A; HNF4G; KLF15; NCOA2; NR0B2; NR1H4; NR5A2; ONECUT1; ONECUT2; PPARA; PROX1; RORA; RORC; RXRA; SALL1; SMAD1; SREBF1; STAT3; TSHZ2; XBP1; ZBTB16; and variants thereof, to generate hepatic cells. These aspects of the invention may be used with any of the combinations of transcription factors described herein.

Cell Types

The method may be used on any cell type, including stem cells. In the case of stem cells, the generation of hepatic cells using the method may be referred to as "cellular reprogramming", "forward reprogramming", "direct programming" or "direct differentiation", i.e., the pluripotent stem cell is differentiated into a hepatic cell. Furthermore, hepatic cell cellular reprogramming may be used as generic terminology referring to the use of transcription factors to differentiate a source cell into hepatic cells.

Sources of cells suitable for methods of the invention may include, for example, any stem cells or non-hepatic cells. For example, the stem cells may be pluripotent stem cells, for example induced pluripotent stem cells, embryonic stem cells or pluripotent stem cells derived by nuclear transfer or cell fusion. It may be preferred that the embryonic stem cell is derived without destruction of the embryo, particularly where the cells are human. In some embodiments, the stem cells are not derived from human or animal embryos, i.e., the invention does not extend to any methods which involve the destruction of human or animal embryos. The stem cells may also include multipotent stem cells, oligopotent stem cells, or unipotent stem cells. The stem cells may also include fetal stem cells or adult stem cells, such as hematopoietic stem cells, mesenchymal stem cells, neural stem cells, epithelial stem cells, skin stem cells. In certain aspects, the stem cells may be isolated from umbilical, placenta, amniotic fluid, chorion villi, blastocysts, bone marrow, adipose tissue, brain, peripheral blood, cord blood, menstrual blood, blood vessels, skeletal muscle, skin and liver.

In one embodiment, the cell population is of human origin. The source cell e.g., a non-hepatic cell, may be of human origin.

In one embodiment, the cell population comprises stem cells, e.g., induced pluripotent stem cells (iPSCs), embryonic stem cells (ESCs), haematopoietic stem cells, mesenchymal stem cells or neuronal stem cells. In a further embodiment, the cell population comprises pluripotent stem cells, e.g., iPSCs or ESCs.

In one embodiment, the source cell is a stem cell, e.g., an iPSC, an ESC, a haematopoietic stem cell, a mesenchymal stem cell or a neuronal stem cell. In a further embodiment, the source cell is a pluripotent stem cell, e.g., an iPSC or an ESC. In some embodiments, the source cell is an iPSC.

Methods of preparing induced pluripotent stem cells from mouse are also known in the art. Induction of iPSCs typically require the expression of or exposure to at least one member from Sox family and at least one member from Oct family. Sox and Oct are thought to be central to the transcriptional regulatory hierarchy that specifies ES cell identity. For example, Sox may be Sox-1, Sox-2, Sox-3, Sox-15, or Sox-18; Oct may be Oct-4. Additional factors may increase the reprogramming efficiency, like Nanog, Lin28, Klf4, or c-Myc; specific sets of reprogramming factors may be a set comprising Sox-2, Oct-4, Nanog and, optionally, Lin-28; or comprising Sox-2, Oct4, Klf and, optionally, c-Myc. In one method, iPSC may be generated by transfecting cells with transcription factors Oct4, Sox2, c-Myc and Klf4 using viral transduction.

In one embodiment, the hepatic cells are human hepatic cells.

In one embodiment, the induced pluripotent stem cells are derived from somatic or germ cells of the patient. Such use of autologous cells would remove the need for matching cells to a recipient. Alternatively, commercially available iPSC may be used, such as those available from WICELL (WiCell Research Institute, Inc, Wisconsin, US). Alternatively, the cells may be a tissue-specific stem cell which may also be autologous or donated.

Delivery of Transcription Factors

It will be understood that methods for increasing the expression of the transcription factors in the cells to be programmed into hepatic cells may include any method known in the art, for example, by induction of expression of one or more expression cassettes previously introduced into the cells, or by introduction of nucleic acids (such as DNA or RNA), polypeptides, or small molecules to the cells. Increasing the expression of certain endogenous but transcriptionally repressed genes may also reverse the silencing or inhibitory effect on the expression of these genes by regulating the upstream transcription factor expression or epigenetic modulation. Therefore, methods of the invention may involve culturing the cell population under conditions to artificially increase the expression level of one or more of the transcription factors described herein.

In one embodiment, the expression of the transcription factors is increased by contacting the cell population with the transcription factors (i.e., the proteins encoding the transcription factors). Delivery of the transcription factors may occur using direct electroporation of transcription factor proteins to the cells.

In an alternative embodiment, the expression of the transcription factors is increased by contacting the cell population with one or more agents that activate or increase the expression or amount of the transcription factors.

In one embodiment, the agent is selected from the group consisting of: a nucleic acid polynucleotide, e.g., messenger RNA (mRNA), coding DNA sequence), a protein, an aptamer and small molecule, ribosome, RNAi agent, guide RNA (gRNA) and peptide-nucleic acid (PNA) and analogues or variants thereof. In one embodiment, the agent is a transcriptional activation system (e.g., a gRNA for use in a gene activation system such as CRISPR/Cas9 or TALEN) for increasing the expression of the one or more endogenous transcription factors.

The method of inducing differentiation of the cell population (i.e., source cells), may comprise delivering to the cells a nucleic acid comprising an open reading frame encoding one or more of the transcription factors (e.g., in an expression cassette), the transcription factor protein, or an activator of transcription of the open reading frame encoding the transcription factor. This results in the amount of the transcription factor in the cells being increased, and the cells differentiate to form hepatic cells. Said open reading frame may be part of a recombinant expression cassette.

In one embodiment, the nucleic acid comprises a recombinant or exogenous expression cassette comprising the one or more transcription factor sequences (or genes) in a sufficient number to cause cellular reprogramming of source cells to hepatic cells. The exogenous expression cassette may comprise an externally inducible transcriptional regulatory element for inducible expression of the one or more transcription factors, such as an inducible promoter, e.g., comprising a tetracycline response element or variant thereof.

If expression of the transcription factors is increased by introducing an exogenous sequence encoding the transcription factor (e.g., the transcription factor gene), then it would be understood that any suitable system for delivering the sequence may be used. The gene delivery system may be a transposon system; a viral gene delivery system; an episomal gene delivery system; or a homologous recombination system such as utilizing a zinc finger nuclease, a transcription activator-like effector nuclease (TALENs), or a meganuclease, or a CRISPR/Cas9, or the like.

Alternatively, introduction of a nucleic acid, such as DNA or RNA, into cells may use any suitable methods for nucleic acid delivery for transformation of a cell, as described herein or as would be known to one of ordinary skill in the art. Such methods include, but are not limited to, direct delivery of DNA such as by ex vivo transfection, by injection (including microinjection), by electroporation, by calcium phosphate precipitation, by using DEAE-dextran followed by polyethylene glycol, by direct sonic loading, by liposome mediated transfection, by receptor-mediated transfection, by microprojectile bombardment, by agitation with silicon carbide fibers, by Agrobacterium-mediated transformation, and any combination of such methods. Through the application of these techniques, cells may be stably or transiently transformed.

Further, the expression cassette (e.g., an inducible recombinant expression cassette) may include cleavable sequences. Such sequences are sequences that are recognised by an entity capable of specifically cutting DNA, and include restriction sites, which are the target sequences for restriction enzymes or sequences for recognition by other DNA cleaving entities, such as nucleases, recombinases, ribozymes or artificial constructs. At least one cleavable sequence may be included, but preferably two or more are present. These cleavable sequences may be at any suitable point in the cassette, such that a selected portion of the cassette, or the entire cassette, can be selectively removed if desired. The cleavable sites may thus flank the part/all of the genetic sequence that it may be desired to remove. The method may therefore also comprise removal of the expression cassette and/or the genetic material.

Vectors

In one embodiment, the transcription factors (e.g., combinations of transcription factors) are introduced into the cell population using a vector. One of skill in the art would be well equipped to construct a vector through standard recombinant techniques. Vectors include but are not limited to plasmids, cosmids, viruses (bacteriophage, animal viruses, and plant viruses), and artificial chromosomes (e.g., YACs).

In one embodiment, the vector is a viral vector. The viral gene delivery system may be an RNA-based or DNA-based viral vector. Viral vectors include retroviral vectors, lentiviral vectors (e.g., derived from HIV-1, HIV-2, SIV, BIV, FIV etc.), gammaretroviral vectors, adenoviral (Ad) vectors (including replication competent, replication deficient and gutless forms thereof), adeno-associated virus-derived (AAV) vectors, simian virus 40 (SV-40) vectors, bovine papilloma virus vectors, Epstein-Barr virus vectors, herpes virus vectors, vaccinia virus vectors, Harvey murine sarcoma virus vectors, murine mammary tumour virus vectors, Rous sarcoma virus vectors and Sendai virus vectors. In a further embodiment, the viral vector is selected from: a lentiviral vector, an adeno-associated virus vector or a Sendai virus vector. In a yet further embodiment, the viral vector is a lentiviral vector.

Lentiviral vectors are well known in the art. Lentiviral vectors are complex retroviruses capable of integrating randomly into the host cell genome, which, in addition to the common retroviral genes gag, pol, and env, contain other genes with regulatory or structural function (e.g., accessory genes Vif, Nef, Vpu, Vpr). Lentiviral vectors have the advantage of being able to infect non-dividing cells and can be used for both in vivo and ex vivo gene transfer and expression of nucleic acid sequences. For example, recombinant lentiviral vector capable of infecting a non-dividing cell wherein a suitable host cell is transfected with two or more vectors carrying the packaging functions, namely gag, pol and env, as well as rev and tat.

In one embodiment, the viral vector is used at a high multiplicity of infection (MOI). A high MOI helps to ensure that more than one transcription factor is introduced into the source cell. In one embodiment, the MOI is greater than 0.5, such as 1.0 or above.

In one embodiment, a nucleic acid sequence encoding the one or more transcription factors is introduced into a cell by a plasmid. In one embodiment, at least one nucleic acid sequence encoding the transcription factors is introduced into a cell on a single plasmid.

In one embodiment, the plasmid is episomal. Episomal vectors are able to introduce large fragments of DNA into a cell but are maintained extra-chromosomally, replicated once per cell cycle, partitioned to daughter cells efficiently, and elicit substantially no immune response. In alternative embodiments, an Epstein-Barr virus (EBV)-based episomal vector, a yeast-based vector, an adenovirus-based vector, a simian virus 40 (SV40)-based episomal vector, or a bovine papilloma virus (BPV)-based vector may be used.

Site-Specific Delivery

Any suitable technique for insertion of a nucleic acid sequence into a specific sequence may be used, and several are described in the art. Suitable techniques include any method which introduces a break at the desired location and permits recombination of the vector into the gap. Thus, a crucial first step for targeted site-specific genomic modification is the creation of a double-strand DNA break (DSB) at the genomic locus to be modified. Distinct cellular repair mechanisms can be exploited to repair the DSB and to introduce the desired sequence, and these are non-homologous end joining repair (NHEJ), which is more prone to error; and homologous recombination repair (HR) mediated by a donor DNA template, that can be used to insert inducible cassettes.

Several techniques exist to allow customized site-specific generation of DSB in the genome. Many of these involve the use of customized endonucleases, such as zinc finger nucleases, TALENs or the clustered regularly interspaced short palindromic repeats/CRISPR associated protein (CRISPR/Cas9) system.

Zinc finger nucleases are artificial enzymes which are generated by fusion of a zinc-finger DNA-binding domain to the nuclease domain of the restriction enzyme FokI. The latter has a non-specific cleavage domain which must dimerise in order to cleave DNA. This means that two zinc finger nuclease monomers are required to allow dimerisation of the FokI domains and to cleave the DNA. The DNA binding domain may be designed to target any genomic sequence of interest, is a tandem array of Cys2His2 zinc fingers, each of which recognises three contiguous nucleotides in the target sequence. The two binding sites are separated by 5-7 bp to allow optimal dimerization of the FokI domains. The enzyme thus is able to cleave DNA at a specific site, and target specificity is increased by ensuring that two proximal DNA-binding events must occur to achieve a double-strand break.

Transcription activator-like effector nucleases, or TALENs, are dimeric transcription factor/nucleases. They are made by fusing a TAL effector DNA-binding domain to a DNA cleavage domain (a nuclease). Transcription activator-like effectors (TALEs) can be engineered to bind practically any desired DNA sequence, so when combined with a nuclease, DNA can be cut at specific locations. TAL effectors are proteins that are secreted by *Xanthomonas* bacteria, the DNA binding domain of which contains a repeated highly conserved 33-34 amino acid sequence with divergent 12th and 13th amino acids. These two positions are highly variable and show a strong correlation with specific nucleotide recognition. This straightforward relationship between amino acid sequence and DNA recognition has allowed for the engineering of specific DNA-binding domains by selecting a combination of repeat segments containing appropriate residues at the two variable positions. TALENs are thus built from arrays of 33 to 35 amino acid modules, each of which targets a single nucleotide. By selecting the array of the modules, almost any sequence may be targeted. Again, the nuclease used may be FokI or a derivative thereof.

Three types of CRISPR mechanisms have been identified, of which type II is the most studied. The CRISPR/Cas9 system (type II) utilises the Cas9 nuclease to make a double-stranded break in DNA at a site determined by a short guide RNA. The CRISPR/Cas system is a prokaryotic immune system that confers resistance to foreign genetic elements. CRISPR are segments of prokaryotic DNA containing short repetitions of base sequences. Each repetition is followed by short segments of "protospacer DNA" from previous exposures to foreign genetic elements. CRISPR spacers recognize and cut the exogenous genetic elements using RNA interference. The CRISPR immune response occurs through two steps: CRISPR-RNA (crRNA) biogenesis and crRNA-guided interference. CrRNA molecules are composed of a variable sequence transcribed from the protospacer DNA and a CRISPR repeat. Each crRNA molecule then hybridizes with a second RNA, known as the trans-activating CRISPR RNA (tracrRNA) and together these two eventually form a complex with the nuclease Cas9. The protospacer DNA encoded section of the crRNA directs Cas9 to cleave complementary target DNA sequences, if they are adjacent to short sequences known as protospacer adjacent motifs (PAMs). This natural system has been engineered and exploited to introduce DSB breaks in specific sites in genomic DNA, amongst many other applications. In particular, the CRISPR type II system from *Streptococcus pyogenes* may be used. At its simplest, the CRISPR/Cas9 system comprises two components that are delivered to the cell to provide genome editing: the Cas9 nuclease itself and a gRNA. The gRNA is a fusion of a customised, site-specific crRNA (directed to the target sequence) and a standardised tracrRNA.

Once a DSB has been made, a donor template with homology to the targeted locus is supplied; the DSB may be repaired by the homology-directed repair (HDR) pathway allowing for precise insertions to be made.

Derivatives of this system are also possible. Mutant forms of Cas9 are available, such as Cas9D10A, with only nickase activity. This means it cleaves only one DNA strand, and does not activate NHEJ. Instead, when provided with a homologous repair template, DNA repairs are conducted via the high-fidelity HDR pathway only. Cas9D10A may be used in paired Cas9 complexes designed to generate adjacent DNA nicks in conjunction with two sgRNAs complementary to the adjacent area on opposite strands of the target site, which may be particularly advantageous.

The elements for making the double-strand DNA break may be introduced in one or more vectors, such as plasmids, for expression in the cell.

Thus, any method of making specific, targeted double strand breaks in the genome in order to effect the insertion of a gene/inducible cassette may be used in the method of the invention. It may be preferred that the method for inserting the gene/inducible cassette utilises any one or more of zinc finger nucleases, TALENs and/or CRISPR/Cas9 systems or any derivative thereof.

Once the DSB has been made by any appropriate means, the gene/inducible cassette for insertion may be supplied in any suitable fashion as described below. The gene/inducible cassette and associated genetic material form the donor DNA for repair of the DNA at the DSB and are inserted using standard cellular repair machinery/pathways. How the break is initiated will alter which pathway is used to repair the damage, as noted above.

Controlled Expression

In one embodiment, expression of the transcription factors is under controlled transcription. In this aspect of the invention, the transcription and translation (expression) of the transcription factors may be controlled within the cell. This permits overexpression of the transcription factor(s), if required.

An exogenous expression cassette carrying the transcription factors may comprise an externally inducible transcriptional regulatory element (i.e., an inducible promoter) for inducible expression of the transcription factors. Said inducible expression cassette may be controlled by addition of an exogenous substance. Whatever culturing conditions are used, the exogenous substance will control expression of the genetic sequence within the inducible expression cassette;

and may either be supplied continuously and then withdrawn in order to induce transcription or supplied as transcription is required, dependent upon its mode of action.

Expression of the transcription factors described herein may be increased using the dual cassette expression system described in WO2018096343, which is incorporated herein by reference. This system targets genetic safe harbour (GSH) sites which provides a reduced risk of epigenetic silencing of the inserted genetic material.

Therefore, in one embodiment, a sequence encoding one or more (e.g., three or more) of the transcription factors is introduced into the cell population using a method comprising:
  targeted insertion of a gene encoding a transcriptional regulator protein into a first genetic safe harbour site of the cell; and
  targeted insertion of an inducible cassette into a second genetic safe harbour site of the cell, wherein said inducible cassette comprises said transcription factor sequence operably linked to an inducible promoter, and said promoter is regulated by the transcriptional regulator protein.

This embodiment of the invention provides a dual expression cassette system. The insertion of the gene encoding a transcriptional regulator protein into the first GSH provides the control mechanism for the expression of the inducible cassette which is operably linked to the inducible promoter and inserted into a second GSH site. In one embodiment, the first and second GSH are different.

A GSH site is a locus within the genome wherein a gene or other genetic material may be inserted without any deleterious effects on the cell or on the inserted genetic material. Most beneficial is a GSH site in which expression of the inserted gene sequence is not perturbed by any read-through expression from neighbouring genes and expression of the inducible cassette minimizes interference with the endogenous transcription programme. More formal criteria have been proposed that assist in the determination of whether a particular locus is a GSH site in future (Papapetrou et al., (2011)) These criteria include a site that is (i) 50 kb or more from the 5' end of any gene, (ii) 300 kb or more from any gene related to cancer, (iii) 300 kb or more from any microRNA (miRNA), (iv) located outside a transcription unit and (v) located outside ultraconserved regions (UCR). It may not be necessary to satisfy all of these proposed criteria, since GSH already identified do not fulfil all of the criteria. It is thought that a suitable GSH will satisfy at least 2, 3, 4 or all of these criteria. Any suitable GSH site may be used in the method of the invention, on the basis that the site allows insertion of genetic material without deleterious effects to the cell and permits transcription of the inserted genetic material. Those skilled in the art may use these simplified criteria to identify a suitable GSH, and/or the more formal criteria set out above.

In one embodiment, the first and second genetic safe harbour sites (GSHs) are selected from (in particular any two) of the hROSA26 locus, the AAVS1 locus, the CLYBL gene, the CCR5 gene or the HPRT gene. Insertions specifically within genetic safe harbour sites is preferred over random genome integration, since this is expected to be a safer modification of the genome, and is less likely to lead to unwanted side effects such as silencing natural gene expression or causing mutations that lead to cancerous cell types.

The adeno-associated virus integration site 1 locus (AAVS1) is located within the protein phosphatase 1, regulatory subunit 12C (PPP1R12C) gene on human chromosome 19, which is expressed uniformly and ubiquitously in human tissues. AAVS1 has been shown to be a favourable environment for transcription, since it comprises an open chromatin structure and native chromosomal insulators that enable resistance of the inducible cassettes against silencing. There are no known adverse effects on the cell resulting from disruption of the PPP1R12C gene. Moreover, an inducible cassette inserted into this site remains transcriptionally active in many diverse cell types.

The hROSA26 site has been identified on the basis of sequence analogy with a GSH from mice (ROSA26—reverse oriented splice acceptor site #26). The hROSA26 locus is on chromosome 3 (3p25.3), and can be found within the Ensembl database (GenBank: CR624523). The integration site lies within the open reading frame (ORF) of the THUMPD3 long non-coding RNA (reverse strand). Since the hROSA26 site has an endogenous promoter, the inserted genetic material may take advantage of that endogenous promoter, or alternatively may be inserted operably linked to a promoter.

Intron 2 of the Citrate Lyase Beta-like (CLYBL) gene, on the long arm of Chromosome 13, was identified as a suitable GSH since it is one of the identified integration hot-spots of the phage derived phiC31 integrase. Studies have demonstrated that randomly inserted inducible cassettes into this locus are stable and expressed. It has been shown that insertion of inducible cassettes at this GSH do not perturb local gene expression (Cerbini et al., (2015)). CLYBL thus provides a GSH which may be suitable for use in the present invention.

CCR5, which is located on chromosome 3 (position 3p21.31) is a gene which codes for HIV-1 major co-receptor. Interest in the use of this site as a GSH arises from the null mutation in this gene that appears to have no adverse effects, but predisposes to HIV-1 infection resistance. Zinc-finger nucleases that target the third exon have been developed, thus allowing for insertion of genetic material at this locus.

The hypoxanthine-guanine phosphoribosyltransferase (HPR7) gene encodes a transferase enzyme that plays a central role in the generation of purine nucleotides through the purine salvage pathway.

GSH in other organisms have been identified and include ROSA26, HRPT and Hipp11 (H11) loci in mice. Mammalian genomes may include GSH sites based upon pseudo attP sites. For such sites, hiC31 integrase, the *Streptomyces* phage-derived recombinase, has been developed as a non-viral insertion tool, because it has the ability to integrate an inducible cassette-containing plasmid carrying an attB site into pseudo attP sites.

Technically, the insertions into the first and/or second GSH may occur on one chromosome, or on both chromosomes. The GSH exists at the same genetic loci on both chromosomes of diploid organisms. Insertion within both chromosomes is advantageous since it may enable an increase in the level of transcription from the inserted genetic material within the inducible cassette, thus achieving particularly high levels of transcription.

Specific insertion of genetic material into the particular GSH based upon customised site-specific generation of DNA double-strand breaks at the GSH may be achieved. The genetic material may then be introduced using any suitable mechanism, such as homologous recombination. Any method of making a specific DSB in the genome may be used, but preferred systems include CRISPR/Cas9 and modified versions thereof, zinc finger nucleases and the TALEN system.

One or more genetic sequences may be controllably transcribed from within the second and/or further GSH. Indeed, the inducible cassette may contain 1, 2, 3, 4, 5, 6, 7, 8, 9 or 10 genetic sequences (e.g., transcription factor sequences) which it is desired to insert into the GSH and the transcription of which be controllably induced. Therefore, the transcription factors required by the present invention may be included within the same cassette introduced into the second genetic safe harbour site. For example, the three or more transcription factors may be included in, for example, three mono-cistronic constructs, one mono-cistronic and one bi-cistronic construct or one tri-cistronic construct. It will be understood that similar combinations of constructs may be used to achieve higher orders of transcription factor expression.

Alternatively, if a combination of transcription factors is used, the individual transcription factors may be introduced into separate GSHs and/or under the control of different inducible promoters. Therefore, in one embodiment, the at least three or more transcription factors are introduced into separate GSHs. This may be achieved by utilising three or more different GSH sites for the three or more transcription factors (i.e., wherein the transcription factors are introduced as mono-cistronic cassettes). Alternatively, this may be achieved by utilising the fact that a GSH exists at the same genetic loci on both chromosomes of diploid organisms, e.g., introducing one transcription factor into the GSH on one chromosome and a different transcription factor into the same GSH on the other chromosome. This embodiment is advantageous if different expression levels or timing of expression of the transcription factors is desired. In one embodiment, the method comprises targeted insertion of the at least three or more transcription factors, each operably linked to an inducible promoter into a second, third and fourth genetic safe harbour site of the source cell. The inducible promoter may be the same of each transcription factor and therefore are all regulated by the transcriptional regulator protein.

A transcriptional regulator protein is a protein that binds to DNA, preferably sequence-specifically to a DNA site located in or near a promoter, and either facilitating the binding of the transcription machinery to the promoter, and thus transcription of the DNA sequence (a transcriptional activator) or blocks this process (a transcriptional repressor).

The DNA sequence that a transcriptional regulator protein binds to is called a transcription factor-binding site or response element, and these are found in or near the promoter of the regulated DNA sequence. Transcriptional activator proteins bind to the response element and promote gene expression. Such proteins are preferred in the methods of the present invention for controlling inducible cassette expression. Transcriptional repressor proteins bind to the response element and prevent gene expression.

Transcriptional regulator proteins may be activated or deactivated by a number of mechanisms including binding of a substance, interaction with other transcription factors (e.g., homo- or hetero-dimerization) or coregulatory proteins, phosphorylation, and/or methylation. The transcriptional regulator protein may be controlled by activation or deactivation.

If the transcriptional regulator protein is a transcriptional activator protein, it is preferred that the transcriptional activator protein requires activation. This activation may be through any suitable means, but it is preferred that the transcriptional regulator protein is activated through the addition to the cell of an exogenous substance. The supply of an exogenous substance to the cell can be controlled, and thus the activation of the transcriptional regulator protein can be controlled. Alternatively, an exogenous substance can be supplied in order to deactivate a transcriptional regulator protein, and then supply withdrawn in order to activate the transcriptional regulator protein.

If the transcriptional regulator protein is a transcriptional repressor protein, it is preferred that the transcriptional repressor protein requires deactivation. Thus, a substance is supplied to prevent the transcriptional repressor protein repressing transcription, and thus transcription is permitted.

Any suitable transcriptional regulator protein may be used, preferably one that may be activated or deactivated. It is preferred that an exogenous substance may be supplied to control the transcriptional regulator protein. Such transcriptional regulator proteins are also called inducible transcriptional regulator proteins.

Tetracycline-Controlled Transcriptional Activation is a method of inducible gene expression where transcription is reversibly turned on or off in the presence of the antibiotic tetracycline or one of its derivatives (e.g., doxycycline which is more stable). In this system, the transcriptional activator protein is tetracycline—responsive transcriptional activator protein (rtTa) or a derivative thereof. The rtTA protein is able to bind to DNA at specific TetO operator sequences. Several repeats of such TetO sequences are placed upstream of a minimal promoter (such as the CMV promoter), which together form a tetracycline response element (TRE). There are two forms of this system, depending on whether the addition of tetracycline or a derivative activates (Tet-On) or deactivates (Tet-Off) the rtTA protein.

In a Tet-Off system, tetracycline or a derivative thereof binds rtTA and deactivates the rtTA, rendering it incapable of binding to TRE sequences, thereby preventing transcription of TRE-controlled genes. This system was first described in Gossen et al., (1992).

The Tet-On system is composed of two components; (1) the constitutively expressed tetracycline-responsive transcriptional activator protein (rtTa) and the rtTa-sensitive inducible promoter (Tet Responsive Element, TRE). This may be bound by tetracycline or its more stable derivatives, including doxycycline (dox), resulting in activation of rtTa, allowing it to bind to TRE sequences and inducing expression of TRE-controlled genes. The use of this may be preferred in the method of the invention.

Thus, the transcriptional regulator protein may thus be tetracycline-responsive transcriptional activator protein (rtTa) protein, which can be activated or deactivated by the antibiotic tetracycline or one of its derivatives, which are supplied exogenously. If the transcriptional regulator protein is rtTA, then the inducible promoter inserted into the second GSH site includes the tetracycline response element (TRE). The exogenously supplied substance is the antibiotic tetracycline or one of its derivatives. Variants and modified rtTa proteins may also be used in the methods of the invention, these include Tet-On Advanced transactivator (also known as rtTA2S-M2) and Tet-On 3G (also known as rtTA-V16, derived from rtTA2S-52).

The tetracycline response element (TRE) generally consists of 7 repeats of the 19 bp bacterial TetO sequence separated by spacer sequences, together with a minimal promoter. Variants and modifications of the TRE sequence are possible, since the minimal promoter can be any suitable promoter. Preferably the minimal promoter shows no or minimal expression levels in the absence of rtTa binding. The inducible promoter inserted into the second GSH may thus comprise a TRE.

A modified system based upon tetracycline control is the T-REX System (Thermo-Fisher Scientific), in which the transcriptional regulator protein is a transcriptional repressor protein, TetR. The components of this system include (i) an inducible promoter comprising a strong human cytomegalovirus immediate-early (CMV) promoter and two tetracycline operator 2 (TetO2) sites, and a Tet repressor (TetR). In the absence of tetracycline, the Tet repressor forms a homodimer that binds with extremely high affinity to each TetO2 sequence in the inducible promoter, and prevent transcription from the promoter. Once added, tetracycline binds with high affinity to each Tet repressor homodimer rendering it unable to bind to the Tet operator. The Tet repressor: tetracycline complex then dissociates from the Tet operator and allows induction of expression. In this instance, the transcriptional regulator protein is TetR and the inducible promoter comprises two TetO2 sites. The exogenously supplied substance is tetracycline or a derivative thereof.

Other inducible expression systems are known and can be used in the method of the invention. These include the Complete Control Inducible system from Agilent Technologies. This is based upon the insect hormone ecdysone or its analogue ponasterone A (ponA) which can activate transcription in mammalian cells which are transfected with both the gene for the *Drosophila melanogaster* ecdysone receptor (EcR) and an inducible promoter comprising a binding site for the ecdysone receptor. The EcR is a member of the retinoid-X-receptor (RXR) family of nuclear receptors. In humans, EcR forms a heterodimer with RXR that binds to the ecdysone-responsive element (EcRE). In the absence of PonA, transcription is repressed by the heterodimer.

Thus, the transcriptional regulator protein can be a repressor protein, such as an ecdysone receptor or a derivative thereof. Examples of the latter include the VgEcR synthetic receptor from Agilent technologies which is a fusion of EcR, the DNA binding domain of the glucocorticoid receptor and the transcriptional activation domain of Herpes Simplex Virus VP16. The inducible promoter comprises the EcRE sequence or modified versions thereof together with a minimal promoter. Modified versions include the E/GRE recognition sequence of Agilent Technologies, in which mutations to the sequence have been made. The E/GRE recognition sequence comprises inverted half-site recognition elements for the retinoid-X-receptor (RXR) and GR binding domains. In all permutations, the exogenously supplied substance is ponasterone A, which removes the repressive effect of EcR or derivatives thereof on the inducible promoter, and allows transcription to take place.

Alternatively, inducible systems may be based on the synthetic steroid mifepristone as the exogenously supplied substance. In this scenario, a hybrid transcriptional regulator protein is inserted, which is based upon a DNA binding domain from the yeast GAL4 protein, a truncated ligand binding domain (LBD) from the human progesterone receptor and an activation domain (AD) from the human NF-κB. This hybrid transcriptional regulator protein is available from Thermo-Fisher Scientific (Gene Switch™). Mifepristone activates the hybrid protein, and permits transcription from the inducible promoter which comprises GAL4 upstream activating sequences (UAS) and the adenovirus E1b TATA box. This system is described in Wang et al., (1994).

The transcriptional regulator protein can thus be any suitable regulator protein, either an activator or repressor protein. Suitable transcriptional activator proteins are tetracycline—responsive transcriptional activator protein or the Gene Switch hybrid transcriptional regulator protein. Suitable repressor proteins include the Tet-Off version of rtTA, TetR or EcR. The transcriptional regulator proteins may be modified or derivatised as required.

The inducible promoter can comprise elements which are suitable for binding or interacting with the transcriptional regulator protein. The interaction of the transcriptional regulator protein with the inducible promoter is preferably controlled by the exogenously supplied substance.

The exogenously supplied substance can be any suitable substance that binds to or interacts with the transcriptional regulator protein. Suitable substances include tetracycline (or derivatives thereof, such as doxycycline), ponasterone A and mifepristone.

It is preferred that the gene encoding the transcriptional regulator protein is operably linked to a constitutive promoter. Alternatively, the first GSH can be selected such that it already has a constitutive promoter than can also drive expression of the transcriptional regulator protein gene and any associated genetic material. Constitutive promoters ensure sustained and high-level gene expression. Commonly used constitutive promoters, including the human β-actin promoter (ACTB), cytomegalovirus (CMV), elongation factor-1α, (EF1α), phosphoglycerate kinase (PGK) and ubiquitin C (UbC). The CAG promoter is a strong synthetic promoter frequently used to drive high levels of gene expression and was constructed from the following sequences: (C) the cytomegalovirus (CMV) early enhancer element, (A) the promoter, the first exon and the first intron of chicken beta-actin gene, and (G) the splice acceptor of the rabbit beta-globin gene.

According to a further aspect of the invention, there is provided a method for the production of hepatic cells from a source cell, comprising the steps of:
  a) targeted insertion of a gene encoding a transcriptional regulator protein into a first genetic safe harbour site of the source cell; and
  b) targeted insertion of one or more (e.g., at least three or more) genes encoding transcription factors selected from the group consisting of: AR, ARID3C, ATF5, CEBPA, CREB3L3, CUX2, EPAS1, FOXA1, FOXA2, FOXA3, GATA4, HHEX, HLF, HNF1A, HNF4A, HNF4G, KLF15, KLF9, MLXIPL, NCOA2, NR0B2, NR1H4, NR1I2, NR1I3, NR5A2, ONECUT1, ONECUT2, PPARA, PROX1, RORA, RORC, RXRA, SALL1, SMAD1, SREBF1, STAT3, TSHZ2, XBP1, ZBTB16, and variants thereof, operably linked to an inducible promoter into a second genetic safe harbour site of the source cell, wherein said inducible promoter is regulated by the transcriptional regulator protein; and
  c) culturing the source cell(s) comprising the insertions to obtain hepatic cells.

According to a further aspect of the invention, there is provided a method for the production of hepatic cells from a source cell, comprising the steps of:
  a) inserting a gene encoding a transcriptional regulator protein into a first genetic safe harbour site of the source cell; and
  b) inserting one or more (e.g., at least three or more) genes encoding transcription factors selected from the group consisting of: AR, ARID3C, ATF5, CEBPA, CREB3L3, CUX2, EPAS1, FOXA1, FOXA2, FOXA3, GATA4, HHEX, HLF, HNF1A, HNF4A, HNF4G, KLF15, KLF9, MLXIPL, NCOA2, NR0B2, NR1H4, NR1I2, NR1I3, NR5A2, ONECUT1, ONECUT2, PPARA, PROX1, RORA, RORC, RXRA, SALL1, SMAD1, SREBF1, STAT3, TSHZ2, XBP1, ZBTB16, and variants thereof, operably linked to an inducible promoter into a second genetic safe harbour site of the source cell, wherein said inducible promoter is regulated by the transcriptional regulator protein; and c) culturing the source cell(s) comprising the insertions to obtain hepatic cells.

It will be understood that this aspect of the invention may be used with any of the combinations of transcription factors described herein.

Obtaining Hepatic Cells

In one embodiment, the method additionally comprises monitoring the cell population for at least one characteristic of a hepatic cell. Cells may be monitored throughout culturing to identify expression of key lineage markers.

For example, monitoring may be through bespoke reporter lines or immunostaining, using fluorescence microscopy or flow cytometry. Such material includes genes for markers or reporter molecules, such as genes that induce visually identifiable characteristics including fluorescent and luminescent proteins. Examples include the gene that encodes jellyfish green fluorescent protein (GFP), which causes cells that express it to glow green under blue/UV light, luciferase, which catalyses a reaction with luciferin to produce light, and the red fluorescent protein from the gene dsRed.

The cell may further comprise a screenable and/or selectable reporter expression cassette, e.g., comprising a hepatic-specific promoter operably linked to a reporter gene.

Selectable markers may include resistance genes to antibiotics or other drugs. Examples of drug resistance genes may include: a puromycin resistance gene, an ampicillin resistance gene, a neomycin resistance gene, a tetracycline resistance gene, a kanamycin resistance gene or a chloramphenicol resistance gene. Cells can be cultured on a medium containing the appropriate drug (i.e., a selection medium) and only those cells which incorporate and express the drug resistance gene will survive. Therefore, by culturing cells using a selection medium, it is possible to easily select cells comprising and expressing a drug resistance gene.

Examples of fluorescent protein genes which may be used as markers include: a green fluorescent protein (GFP) gene, yellow fluorescent protein (YFP) gene, red fluorescent protein (RFP) gene or aequorin gene. Cells expressing the fluorescent protein gene can be detected using a fluorescence microscope and be selected using a cell sorter, such as a flow cytometer. Fluorescence activated cell sorting (FACS) is a specialised type of flow cytometry that can be used to select the cells expressing the fluorescent protein.

Examples of chromogenic enzyme genes which may be used as markers include but are not limited to: β-galactosidase gene, β-glucuronidase gene, alkaline phosphatase gene, or secreted alkaline phosphatase SEAP gene. Cells expressing these chromogenic enzyme genes can be detected by applying the appropriate chromogenic substrate (e.g., X-gal for β galatosidase) so that cells expressing the marker gene will produce a detectable colour (e.g., blue in a blue-white screen test).

The method may therefore comprise a selection or enrichment step for the hepatic cells provided from the methods described herein. In one embodiment, the method comprises the step of sorting the hepatic cells using fluorescence activated cell sorting (FACS) or immunomagnetic sorting methods based on the expression of hepatic markers and/or absence of non-hepatic markers. In another embodiment, hepatic cells are enriched by drug-resistance selection from genetically engineered source cells expressing an antibiotic-resistance gene under the control of a hepatic specific promoter (e.g., Albumin or CYP3A4 promoter).

The method may generate cells (i.e., differentiated cells) exhibiting at least one characteristic of a hepatic cell. One or more characteristics may be used to select for the hepatic cells generated by methods of the invention.

Characteristics include but are not limited to the detection or quantitation of expressed cell markers, enzymatic activity, and the characterization of morphological features and intercellular signalling. The biological function of a hepatic cell may also be evaluated, for example, by analysing glycogen storage, albumin and biliary secretion, lipid synthesis or urea production.

In one embodiment, the characteristic (i.e., of a hepatic cell, in particular a human hepatic cell) is selected from one or more of:

(i) expression of one or more hepatic cell markers, such as Glucose-6-phosphatase, Albumin, a1-Antitrypsin (AAT), Fumarylacetoacetase (FAH), Cytokeratin 8 (CK8), Cytokeratin 18 (CK18), Asialoglycoprotein Receptor (ASGR), Alcohol Dehydrogenase 1, Arginase Type I, Cytochrome p450 3A4 (CYP3A4), Cytochrome p450 2C9 (CYP2C9), UDP glucuronosyltransferase 1 family, polypeptide A1 (UGT1A1), Liver-specific Organic Anion Transporter (LST-1), or a combination thereof;

(ii) activity of glucose-6-phosphatase, CYP3A4, CYP2C9, albumin synthesis and secretion, bile production or secretion, urea production, or xenobiotic detoxification; or (iii) hepatic cell morphological features.

In one embodiment, the cells are sorted on the basis of acquisition of expression of a hepatic cell marker, such as Albumin or CYP3A4, which have been associated with hepatic cells and mature adult hepatic cells.

Therefore, in a further embodiment, the characteristic comprises a hepatic cell marker selected from Albumin and CYP3A4.

The hepatic cell markers may be markers obtained by transcriptome analysis. For example, single cell RNA sequencing has been used to provide detailed transcriptional profiles of human liver cells obtained from donors. This information can be used to identify hepatic cells generated by the methods described herein. Single cell RNA sequencing data is provided in Aizarani et al., (2019); MacParland et al., (2018) and Segal et al., (2019), which are herein incorporated by reference.

The method may comprise assaying the differentiated cells obtained by the method described herein and determining a set of transcribed genes; comparing the set of transcribed genes of the differentiated cells to one or more reference sets of transcribed genes from one or more reference hepatic cells; and identifying a match between the differentiated cells and a reference hepatic cell.

In one embodiment, the method comprises the step of identifying differentiated cells as a type of hepatic cell by assaying morphological features of the differentiated cells and matching the morphological features to a reference tissue or cell's morphological features.

In one embodiment, the method comprises the step of identifying differentiated cells as a type of hepatic cell by assaying protein marker expression of the differentiated cells and matching the protein marker expression to a reference hepatic cell protein marker expression.

In one embodiment, the method comprises the step of identifying differentiated cells as a type of hepatic cell by assaying a function and matching the function to a function of a reference hepatic cell.

In one embodiment, the cells obtained by the methods of the invention express a liver committed endodermal phenotype. In one embodiment, the cells obtained by the methods of the invention express a hepatoblast phenotype. In one embodiment, the cells obtained by the methods of the invention express a hepatocyte phenotype.

Alternatively, certain differentiated cells may be sorted from other differentiated cells and from cells on the basis of their expression of a lineage-specific cell surface antigen. Yet another means is by assessing expression at the RNA level, e.g., by RT-qPCR methods or by single cell RNA sequencing without any sorting or pre-selection step. Such techniques are known in the art.

Cell Culturing

In one embodiment, the method includes culturing the cell population for a sufficient time and under conditions to allow differentiation to a hepatic cell. Generally, cells of the present invention are cultured in a culture medium, which is a nutrient-rich buffered solution capable of sustaining cell growth.

The cell culture medium may contain any of the following in an appropriate combination: salt(s), buffer(s), amino acids, glucose or other sugar(s), antibiotics, serum or serum replacement, and other components such as peptide growth factors, etc. Cell culture media ordinarily used for particular cell types are known to those skilled in the art. Exemplary cell culture media for use in methods of the invention are described in Ang et al., (2018).

Hepatic cells may be obtained using methods of the invention at least about 3, 4, 5, 6, 7, 8, 9, 10, 11, 12, 13, 14, 15, 16, 17, 18, 19, or 20 days after culturing. In one embodiment, the method comprises culturing under suitable conditions for at least 4 days, such as at least 6 days or at least 11 days. In further embodiments, method comprises culturing cells for a duration (e.g., at least 4 days, at least 5 days, at least 6 days, at least 7 days, at least 8 days, at least 9 days, at least 10 days, at least 11 days, at least 12 days, at least 13 days, at least 14 days, at least 21 days, at least 28 days, or longer, e.g., from 5 days to 40 days, from 7 days to 35 days, from 14 days to 28 days, or about 21 days) which is sufficient to generate hepatic cells. In some embodiments, the cells are cultured for a period of several hours (e.g., about 2, 3, 4, 5, 6, 7, 8, 9, 10, 15, 18, or 21 hours) to about 35 days (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, or 35 days). In one embodiment, the method comprises culturing the cells for at least about 5, 10, 15 or 20 days to produce hepatic cells. In one embodiment, the cells are cultured for a period of between 4 and 25 days, such as between 14 and 21 days.

After culturing, the cell population may comprise two cell types. For example, such a cell population may have two cell types including the stem cells and hepatic cells. In one embodiment, the cell population comprises up to 1, 5, 10, 15, 20, 25, 30, 35, 40, 45, 50, 60, 70, 80, 85, 90, 91, 92, 93, 94, 95, 96, 97, 98, 99 or 99.5% (or any intermediate ranges) of hepatic cells in the resulting cell population.

Culturing the cells may either help to induce cells to commit to a more mature phenotype, preferentially promote survival of the mature cells, or have a combination of both these effects.

According to a further aspect of the invention, there is provided a cell obtainable by any one of the methods defined herein.

According to a further aspect of the invention, there is provided a cell comprising one or more exogenous expression cassettes encoding one or more (e.g., at least three or more) transcription factors selected from the group consisting of: AR, ARID3C, ATF5, CEBPA, CREB3L3, CUX2, EPAS1, FOXA1, FOXA2, FOXA3, GATA4, HHEX, HLF, HNF1A, HNF4A, HNF4G, KLF15, KLF9, MLXIPL, NCOA2, NR0B2, NR1H4, NR1I2, NR1I3, NR5A2, ONECUT1, ONECUT2, PPARA, PROX1, RORA, RORC, RXRA, SALL1, SMAD1, SREBF1, STAT3, TSHZ2, XBP1, ZBTB16 and variants thereof. It will be understood that this aspect of the invention may be used with any of the combinations of transcription factors described herein.

According to a further aspect of the invention, there is provided a cell comprising one or more exogenous expression cassettes encoding at least three or more transcription factors, wherein the three or more transcription factors are selected from the group consisting of: FOXA1 or FOXA3; NR1I2 or NR1I3; HHEX; CREB3L3; GATA4; KLF9; ATF5; MLXIPL; FOXA2; AR; ARID3C; CEBPA; CUX2; EPAS1; HLF; HNF1A; HNF4A; HNF4G; KLF15; NCOA2; NR0B2; NR1H4; NR5A2; ONECUT1; ONECUT2; PPARA; PROX1; RORA; RORC; RXRA; SALL1; SMAD1; SREBF1; STAT3; TSHZ2; XBP1; ZBTB16; and variants thereof.

In one embodiment, the cell is a hepatic cell, in particular an engineered hepatic cell.

As described herein, the exogenous expression cassettes encoding the three or more transcription factors may be integrated into the genome of the cell. In a further embodiment, exogenous expression cassettes encoding the three or more transcription factors are integrated into a (specific) target site in the genome of the cell. Alternatively, exogenous expression cassettes encoding the three or more transcription factors are integrated into a non-specific target site in the genome of the cell.

Cell Compositions

According to a further aspect, there is provided a pharmaceutical composition comprising the hepatic cells produced by the method as described herein and a pharmaceutically acceptable carrier.

Pharmaceutical compositions may include hepatic cells as described herein in combination with one or more pharmaceutically or physiologically acceptable carrier, diluents, or excipients. Such compositions may include buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminium hydroxide); and preservatives. Cryopreservation solutions which may be used in the pharmaceutical compositions of the invention include, for example, DMSO.

For purposes of manufacture, distribution, and use, the hepatic cells described herein may be supplied in the form of a cell culture or suspension in an isotonic excipient or culture medium, optionally frozen to facilitate transportation or storage.

Uses of Hepatic Cells

The cells produced according to any of the methods of the invention have applications in basic and medical research, diagnostic and therapeutic methods. The cells may be used in vitro to study cellular development, provide test systems for new drugs, enable screening methods to be developed, scrutinise therapeutic regimens, provide diagnostic tests and the like. These uses form part of the present invention. Alternatively, the cells may be transplanted into a human or animal patient for diagnostic or therapeutic purposes. The use of the cells in therapy is also included in the present invention.

Hepatic cells generated by methods of the invention find particular use in drug screening. Therefore, in one embodiment, the method additionally comprises contacting the hepatic cells with a test substance and observing a change (e.g., an effect) in the hepatic cells induced by the test substance. The change or effect may be observed using methods known in the art, for example using pharmacological or toxicological assays. In one aspect, the cells may be used in a method of assessing a test substance (e.g., a drug, such as a compound), comprising assaying a pharmacological or toxicological property of the test substance on the hepatic cells provided by the methods described herein. The method may comprise: a) contacting the hepatic cell described herein with the test substance; and b) assaying an effect of the test substance on the hepatic cell.

Assessment of the activity of a candidate molecule may involve combining the hepatic cells described herein with the candidate molecule, determining any change in the morphology, phenotype, or metabolic activity of the hepatic cells that is attributable to the molecule (i.e., compared with a control, such as untreated cells or cells treated with an inert compound), and then correlating the effect of the molecule with the observed change. The screening may be done either because the candidate molecule is designed to have a pharmacological effect on hepatic cells, or because the molecule is designed to have effects elsewhere but there is a need to determine if it has and unintended hepatic side effects.

Cytotoxicity can be determined in the first instance by the effect on cell viability, survival, morphology, and leakage of enzymes into the culture medium. More detailed analysis may be conducted to determine whether a test substance affects cell function (e.g., gluconeogenesis, ureagenesis, and plasma protein synthesis) without causing toxicity.

Alternatively, the cells can be used to assess changes in gene expression patterns caused by a potential drug candidate. In this embodiment, the changes in gene expression pattern from addition of the candidate drug can be compared with the gene expression pattern caused by a control drug with a known effect on the liver.

Therefore, according to a further aspect, there is provided a method for drug screening (e.g., evaluating drug reactivity), comprising a step of using the hepatic cells produced by the method as described herein. According to a further aspect of the invention, there is provided a method of drug screening comprising contacting a hepatic cell generated using the method as defined herein, or a hepatic cell as defined herein, with the drug and observing a change in the hepatic cells induced by the drug.

Hepatic cells of the invention may also be used in screens to assess how the drug is metabolised in the liver, e.g., through production of any drug by-products. Therefore, according to a further aspect, there is provided a method of drug screening comprising contacting a hepatic cell generated using the method as defined herein, or a hepatic cell as defined herein, with the drug and observing a change in the metabolism of the drug.

According to a further aspect of the invention, there is provided a method for drug target identification in hepatic cells, e.g., using genetic perturbation screening combined to drug addiction.

According to a further aspect of the invention, there is provided the hepatic cell as defined herein for use in therapy. In one embodiment, the therapy comprises tissue regeneration. References herein to "tissue regeneration" refer to therapies which restore the function of diseased and damaged organs and tissues by re-creating lost or damaged tissues.

Therefore, hepatic cells of the invention may also be used to restore a degree of liver function to a subject in need of such therapy. Therefore, in one embodiment, the method additionally comprises transplanting the hepatic cells into a patient. In this aspect of the invention, the cells used to generate the hepatic cells may be autologous (i.e., mature cells removed, modified and returned to the same individual) or from a donor (i.e., allogeneic, including a stem cell line).

According to a further aspect, there is provided a method for cell transplantation into the liver, comprising the step of transplanting the hepatic cells produced by the method as described herein.

In one embodiment, the hepatic cells are encapsulated, such as alginate-encapsulated. For example, hepatic cells may be encapsulated using commercially available alginate beads and techniques known in the art. This embodiment has the advantage of avoiding implantation in the liver or being subject to immune rejection and therefore the hepatic cells do not need to be HLA-matched between the donor and patient. Treatment by administration of encapsulated hepatic cells may be used in patients suffering from acute (e.g., from acetaminophen overdose) or chronic liver failure (e.g., from cirrhosis).

In a further aspect, there may also be provided a method for treating a subject having or at risk of a liver dysfunction comprising administering to the subject a therapeutically effective amount of hepatic cells or a hepatic cell-containing cell population provided herein.

According to a further aspect, there is provided a method for treating a disease comprising the step of using the hepatic cells produced by the method as described herein. Said disease may be a disease which comprises an acute or chronic liver dysfunction. Diseases suitable for therapy with the hepatic cells described herein include diseases which are associated with acute or chronic liver dysfunction, such as autoimmune liver disease (such as autoimmune chronic hepatitis or primary biliary cirrhosis), cirrhosis, acute drug-induced liver injury (e.g., acetaminophen overdose), fulminant hepatic failure, hepatobiliary carcinoma, inherited hepatic insufficiency (such as Wilson's disease, Gilbert's syndrome, or α1-antitrypsin deficiency), viral hepatitis, and any other condition that results in impaired liver function.

The hepatic cells can be administered at any site that has adequate access to the circulation, typically within the abdominal cavity. For some metabolic and detoxification functions, it is advantageous for the hepatic cells to have access to the biliary tract. Accordingly, the hepatic cells may be administered near the liver (e.g., in the treatment of chronic liver disease) or the spleen (e.g., in the treatment of fulminant hepatic failure). In one method, the hepatic cells are administered into the hepatic circulation either through the hepatic artery or through the portal vein. As described hereinbefore, the hepatic cells may be encapsulated, such as alginate-encapsulated.

According to a further aspect of the invention, there is provided a bio-artificial liver comprising the hepatic cells as defined herein. Development of bio-artificial livers have been widely described in the art, for example see Selden et al. (2017) Scientific Reports 7: 14518 and exemplification in U.S. Pat. Nos. U.S. Pat. Nos. 5,837,234, 6,582,955, 7,824, 912 and 9,402,944. Bio-artificial livers can be used to temporarily replace the functions of the liver, allowing the patient's liver to repair and regenerate. They can also be used to imitate liver-specific functions, analyse the effects of genetic alterations on tissue functioning and to provide highly differentiated tissue that can be used as a model for screening of drugs or treatments. Bio-artificial livers rely on the use of hepatic cells to perform detoxification and secretion of liver-synthesized factors. Bio-artificial livers may comprise hepatic cells suspended in plate dialysers, microencapsulated in a suitable substrate, or attached to microcarrier beads coated with extracellular matrix. Alternatively, hepatic cells can be placed on a solid support in a packed bed, in a multiplate flat bed, on a microchannel screen, or surrounding hollow fibre capillaries. The bio-artificial liver may be part of a device that has an inlet and outlet through which the subject's blood is passed, optionally with additional ports for supplying nutrients to the cells.

Differentiation Kits

According to a further aspect, there is provided a kit for differentiating a cell into a hepatic cell comprising:
  (i) a source cell and an agent that activates or increases the expression or amount of one or more (e.g., at least three or more) transcription factors; or
  (ii) one or more expression cassette(s) encoding one or more (e.g., at least three or more) transcription factors;
  wherein the one or more (e.g., three or more) transcription factors is selected from the group consisting of: AR, ARID3C, ATF5, CEBPA, CREB3L3, CUX2, EPAS1, FOXA1, FOXA2, FOXA3, GATA4, HHEX, HLF, HNF1A, HNF4A, HNF4G, KLF15, KLF9, MLXIPL, NCOA2, NR0B2, NR1H4, NR1I2, NR1I3, NR5A2, ONECUT1, ONECUT2, PPARA, PROX1, RORA, RORC, RXRA, SALL1, SMAD1, SREBF1, STAT3, TSHZ2, XBP1, ZBTB16, and variants thereof.

According to a further aspect, there is provided a kit for differentiating a cell into a hepatic cell comprising:
  (i) a source cell and an agent that activates or increases the expression or amount of at least three or more transcription factors; or
  (ii) one or more expression cassette(s) encoding at least three or more transcription factors,
  wherein the three or more transcription factors is selected from the group consisting of: FOXA1 or FOXA3; NR1I2 or NR1I3; HHEX; CREB3L3; GATA4; KLF9; ATF5; MLXIPL; FOXA2; AR; ARID3C; CEBPA; CUX2; EPAS1; HLF; HNF1A; HNF4A; HNF4G; KLF15; NCOA2; NR0B2; NR1H4; NR5A2; ONECUT1; ONECUT2; PPARA; PROX1; RORA; RORC; RXRA; SALL1; SMAD1; SREBF1; STAT3; TSHZ2; XBP1; ZBTB16; and variants thereof.

In one embodiment, the expression cassette comprises an inducible expression construct comprising a sequence encoding one or more transcription factors.

As described herein, combinations of the transcription factors described herein are of particular use in the present invention. If a combination of transcription factors is required, these may be encoded on the same or on different expression cassettes. Therefore, in one embodiment, the kit comprises an expression cassette (preferably an inducible expression cassette) encoding two or more transcription factors, such as three, four, five, six, seven or eight transcription factors. Preferably, the kit comprises an expression cassette encoding three or more, more preferably four or more, transcription factors.

According to a further aspect, there is provided a use of a kit as defined herein, for differentiating a cell into a hepatic cell.

The kit may include one or more articles and/or reagents for performance of the method. For example, one or more transcription factor genes, derivatives, variants or fragments thereof, for use in the methods described herein may be provided in isolated form and may be part of a kit, e.g., in a suitable container such as a vial in which the contents are protected from the external environment.

In one embodiment, the kit additionally comprises at least one source cell, such as a pluripotent stem cell (such as an induced pluripotent stem cell) or a non-pluripotent, non-hepatic cell.

In one embodiment, the kit additionally comprises a medium for culturing the cell and instructions for preparing the enhanced potency cells or reprogrammed pluripotent cells in accordance with the method defined herein.

It will be understood that all embodiments described herein may be applied to all aspects of the invention.

Other features and advantages of the present invention will be apparent from the description provided herein. It should be understood, however, that the description and the specific examples while indicating preferred embodiments of the invention are given by way of illustration only, since various changes and modifications will become apparent to those skilled in the art. The invention will now be described using the following, non-limiting examples:

EXAMPLES

Introduction

A screening method was conducted to identify transcription factors (TFs) that are involved in reprogramming induced pluripotent stem cells (iPSCs) to hepatic cells.

Figure 1:
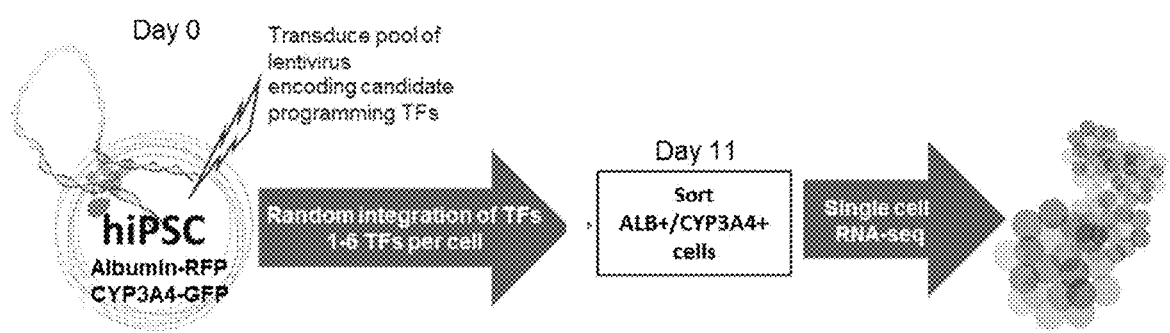
FIG. 1. Screening strategy for TFs with hepatic reprogramming activity

TFs that are listed in Table 1 were introduced to iPSCs by transducing pools of lentiviral vector (LV) each carrying a single TF in order to stably integrate multiple unique TF coding sequences into the genome in a random manner and overexpress them (FIG. 1). Multiplicity of Infection (MOI) was adjusted to result in integration of 1-6 different TFs per cell on average in the majority of starting iPSC population. The transduced iPSCs and non-transduced controls were cultured in parallel under identical conditions. The starting iPSCs carry red and green fluorescent protein reporters, RFP and GFP, for Albumin and CYP3A4, respectively, that are knocked in the respective endogenous gene loci. Albumin (ALB) is the main protein of plasma secreted by liver. It is expressed in fetal and adult hepatocytes and hepatobiliary bipotential progenitors. CYP3A4 is a member of CYP450 family of oxidizing enzymes that are involved in xenobiotic excretion and its expression is restricted to mature adult hepatocytes (Aizarani et al., 2019; MacParland et al., 2018; Segal et al., 2019). Thus, post-LV transduction hepatic cells of different developmental stages and types can be tracked with ALB:RFP alone. In contrast, co-expression of ALB:RFP and CYP3A4:GFP marks potential mature hepatic cells. The cells were imaged daily following LV transduction using a fluorescent microscope to monitor expression of the two fluorescent reporters. On day 11 RFP+/GFP+ cells were sorted and subjected to single cell RNA sequencing. The single cell transcriptomes were analysed to identify exogenous reprogramming TFs that were overexpressed in each cell. The single cell transcriptomes were also compared to those of primary hepatocytes to determine the degree of transcriptome similarity at the single cell level. This general strategy is depicted in FIG. 1.

Results

ALB+/CYP3A4+ Cells can be Generated within 11 Days Upon Overexpression of a Pool of 39 or 34 Programming TFs Upon transduction of pool lentiviral vectors carrying all 39 TFs (Table 1) or 34 that were selected for initial screening (Table 2), ALB:RFP was expressed by day 7 (FIGS. 2 and 3, panels a-c) in a subpopulation of cells. In contrast, CYP3A4:GFP expression was detected only by day 10, in a smaller fraction of ALB:RFP+ cells (FIGS. 2 and 3, panels d-f, arrowheads), consistent with in vivo expression profile of CYP3A4. Importantly, neither RFP nor GFP expression were detected in non-transduced cells cultured under identical conditions, demonstrating that culture medium alone is not sufficient to induce hepatic markers (FIGS. 2 and 3, panels g-i). These results establish that combinations of the TFs in the 39 or 34 candidates are required for hepatic reprogramming of iPSCs.

TABLE 2

Transcription factors for generation of hepatic cells, including accession numbers (as accessed on 11 Mar. 2020)

| Transcription Factor Gene name | Ensembl Gene ID |
| --- | --- |
| AR | ENSG00000169083 |
| ATF5 | ENSG00000169136 |
| CEBPA | ENSG00000245848 |
| CREB3L3 | ENSG00000060566 |
| EPAS1 | ENSG00000116016 |
| FOXA1 | ENSG00000129514 |
| FOXA2 | ENSG00000125798 |
| FOXA3 | ENSG00000170608 |
| GATA4 | ENSG00000136574 |
| HHEX | ENSG00000152804 |
| HLF | ENSG00000108924 |
| HNF1A | ENSG00000135100 |
| HNF4A | ENSG00000101076 |
| HNF4G | ENSG00000164749 |
| KLF15 | ENSG00000163884 |
| KLF9 | ENSG00000119138 |
| MLXIPL | ENSG00000009950 |
| NCOA2 | ENSG00000140396 |
| NR1H4 | ENSG00000012504 |
| NR1I2 | ENSG00000144852 |
| NR1I3 | ENSG00000143257 |
| NR5A2 | ENSG00000116833 |
| ONECUT1 | ENSG00000169856 |
| PPARA | ENSG00000186951 |
| PROX1 | ENSG00000117707 |
| RORA | ENSG00000069667 |
| RORC | ENSG00000143365 |
| RXRA | ENSG00000186350 |
| SMAD1 | ENSG00000170365 |
| SREBF1 | ENSG00000072310 |
| STAT3 | ENSG00000168610 |
| TSHZ2 | ENSG00000182463 |
| XBP1 | ENSG00000100219 |
| ZBTB16 | ENSG00000109906 |

Day 11 ALB+/CYP3A4+ Cells are Transcriptionally Similar to Primary Hepatocytes

On day 11 post-LV transduction of pool of 34 TFs (Table 2), cultures were dissociated and subjected to flow cytometry (FIG. 4A). ALB:RFP+ and ALB:RFP+/CYP3A4:GFP+ cells constituted 5.7 and 0.08 percent of the population, respectively (FIG. 4A). ALB:RFP+/CYP3A4:GFP+ cells were sorted and single cell RNA-sequencing was performed. In order to assess the relationship of the sorted cells to hepatocytes residing in human liver, day 11 single cell RNA-seq datasets were compared to the published single cell RNA-seq datasets of human liver cells from MacParland et al., 2018. In addition to hepatocytes, human liver contains non-hepatocyte cell types such as cholangiocytes, Kuppfer cells, stellate cells, endothelial cells and immune cells, which are included in MacParland et al., 2018 datasets. We used Uniform Manifold Approximation and Projection (UMAP) to group cells based on differential gene expression of all genes expressed in sorted day 11 cells and MacParland dataset (FIG. 4B). We found that a subset of day 11 RFP+/GFP+ cells are clustered together with hepatocytes isolated from human liver, showing that day 11 reprogrammed cells have acquired transcriptomes that are similar to their in vivo counterparts. This result consolidates hepatic reprogramming capacity of the 34 TFs. Despite expressing Albumin and CYP3A4 reporters, a fraction of Day 11 cells did not cluster with hepatocytes, which suggests that they were incompletely programmed with respect to global gene expression.

Identification of Adult and Fetal Hepatocyte-Like Cells in Reprogrammed Populations A similar analysis as shown in FIG. 4 was run again with a larger reference cell dataset to determine the cell type identity of populations that emerge during hepatic cell reprogramming. We first constructed a reference single cell RNA-sequencing (scRNA-seq) dataset panel, consisting of a core iPSC line from Bit Bio and publicly available data from human adult liver (MacParland et al, 2018) and fetal liver (Popescu et al, 2019) (FIG. 5A).

We then sampled several reprogrammed populations at different timepoints of reprogramming, after transduction of iPSCs with a pool of lentiviruses (LVs) for 34 TFs (from Table 2) or for 17 TFs (those on Table 3 plus PROX1). We sorted the reprogrammed cells based on expression of ALB-RFP and CYP3A4-GFP reporters, including double positive, single positive and double negative populations (FIG. 5C). Using the reference library, we trained a classifier to cluster different cell types based on their transcriptome (genome-wide gene expression). We then used UMAP, a non-linear dimensionality reduction technique (Becht et al. 2019), to visualize the different cell types. UMAP plots show the clear distinction between four different cell types within the reference cells (FIG. 6A): (1) iPSCs (2), adult hepatocytes (3), fetal hepatocytes (4) and non-hepatocyte cell types. The non-hepatocyte cluster includes other cell types found in the liver such as blood cells, immune cells, endothelial cells, cholangiocytes, Kupffer cells and stellate cells. In order to test if the classifier can identify cell types from a new dataset correctly, we used a control scRNA-seq dataset that we generated using cryopreserved adult hepatocytes that were obtained from a commercial source (FIG. 5B). These are clustered together with reference adult hepatocytes (FIG. 6B), confirming that the classifier can correctly identify cell types. We then used the classifier for reprogrammed populations. Projection of reprogrammed cells onto the reference cells showed expected heterogeneity with a diverse distribution across the cell type landscape (FIG. 6C). We observed a subpopulation of reprogrammed cells that clustered with the reference adult hepatocytes (FIGS. 6C and D). The percentage of reprogrammed cells that are identified as adult hepatocytes increased with the duration of reprogramming and positively correlated with expression of ALB and CYP3A4 reporters (FIG. 6E). Among the cells obtained from the 34 TF screen, Day 11 (D11) ALB+/CYP3A+ cells exhibited the highest percentage of cells clustering with adult hepatocytes. This percentage was further increased in the Day 10 (D11) ALB+/CYP3A4+ population obtained from the 17 TF screen, consistent with increased reprogramming capacity of this set of TFs as predicted from our bioinformatic analysis. In contrast, Day 2 (D2) cells, and reporter-negative populations from Day 7 (D7) and Day 11 (D11) cells made the lowest contributions to the adult or fetal hepatocyte population and majority of these cells aligned with iPSCs.

A Subset of Programming TFs are Enriched in Day 11 RFP+/GFP+ Cells

Transduced exogeneous TF (eTF) sequences expressed in each cell were selectively identified from the sequencing reads. 55% of day 11 RFP+/GFP+ cells expressed equal to or fewer than 6 unique TFs per cell (FIG. 7). Expression level of each TF in single cells were plotted. This analysis showed that a set of 16 TFs (Table 3) were enriched in the fraction of day 11 RFP+/GFP+ cells that show high similarity to in vivo hepatocytes.

TABLE 3

Transcription factors for generation of hepatic cells, including accession numbers (as accessed on 11 Mar. 2020)

| Transcription Factor Gene name | Ensembl Gene ID |
| --- | --- |
| ATF5 | ENSG00000169136 |
| CREB3L3 | ENSG00000060566 |
| FOXA1 | ENSG00000129514 |
| FOXA2 | ENSG00000125798 |
| FOXA3 | ENSG00000170608 |
| GATA4 | ENSG00000136574 |
| HHEX | ENSG00000152804 |
| HNF4A | ENSG00000101076 |
| HNF4G | ENSG00000164749 |
| KLF9 | ENSG00000119138 |
| MLXIPL | ENSG00000009950 |
| NR1I2 | ENSG00000144852 |
| NR1I3 | ENSG00000143257 |
| ONECUT1 | ENSG00000169856 |
| RXRA | ENSG00000186350 |
| SREBF1 | ENSG00000072310 |

Hepatic Cells Expressing Mature Hepatocyte Markers are Generated by Overexpression of a Pool of 14 TFs 14 TFs were selected out of 16 TFs listed in Table 3, based on high frequency of expression in day 11 RFP+/GFP+ cells. These 14 TFs (Table 4) were transduced to iPSCs as a pool. On day 13 post-LV transduction, we performed immunofluorescence staining using an antibody against CYP3A4. GFP signal from the CYP3A4:GFP reporter colocalized with endogenous CYP3A4 protein, confirming the functionality of the reporter (FIG. 8A). We also stained the cells for other mature hepatocyte markers, including CYP2C9, another member of the CYP450 family of oxidizing enzymes and UGT1A1, a UDP-glucuronosyltransferase involved in drug, steroid hormone and bilirubin excretion. We found that a subpopulation of cells co-express both CYP2C9 and UGT1A1 in addition to CYP3A4:GFP and ALB:RFP (FIG. 8B), indicating that the 14 TFs can generate hepatic cells which synthesize key hepatocyte enzymes involved in drug metabolism and excretion.

TABLE 4

Transcription factors for generation of hepatic cells, including accession numbers (as accessed on 11 Mar. 2020)

| Transcription Factor Gene name | Ensembl Gene ID |
| --- | --- |
| ATF5 | ENSG00000169136 |
| CREB3L3 | ENSG00000060566 |
| FOXA1 | ENSG00000129514 |
| FOXA2 | ENSG00000125798 |

TABLE 4-continued

Transcription factors for generation of hepatic cells, including accession numbers (as accessed on 11 Mar. 2020)

| Transcription Factor Gene name | Ensembl Gene ID |
| --- | --- |
| FOXA3 | ENSG00000170608 |
| GATA4 | ENSG00000136574 |
| HHEX | ENSG00000152804 |
| HNF4A | ENSG00000101076 |
| KLF9 | ENSG00000119138 |
| MLXIPL | ENSG00000009950 |
| NR1I2 | ENSG00000144852 |
| NR1I3 | ENSG00000143257 |
| RXRA | ENSG00000186350 |
| SREBF1 | ENSG00000072310 |

Comparison of Hepatocyte-Specific Gene Expression Between Reprogrammed Cells and Reference Primary Hepatocytes We selected a set of genes whose expression is unique to adult and/or fetal hepatocytes and pluripotent stem cells, using the PanglaoDB database (https://panglaodb.se/) and published literature (Segal et al. 2019), and are robustly expressed in the reference cells (summarised in FIG. 5). This set consisted of marker genes associated specifically with adult hepatocytes (28 genes), fetal hepatocytes (8 genes) and genes expressed in both adult and fetal hepatocytes (41 genes) and iPSCs (6 genes). We plotted the expression level of each gene in single cells of the reference cells and reprogrammed cells (FIG. 9A-D) and grouped them according to their association with different cell type clusters as per FIGS. 6C and D.

Notably, both the reference and cryopreserved control hepatocytes exhibited significant heterogeneity with respect to expression of many genes in the cell type-specific gene panel. This is likely a reflection of heterogeneity of hepatocytes in the human liver which arises from the presence of different hepatocyte subtypes with different functions in different liver zones (Kietzmann, 2017). Alternatively, the observed heterogeneity might be resulting from the variability in detection of transcripts, which is known as drop-out (Hague et al., 2017). We asked to what extent the reprogrammed cells recapitulated the gene expression profiles of reference cell types. In general, we observed a high level of concordance between the matching cell type clusters identified in reference and reprogrammed cells (FIG. 9A-D). Genes that are robustly expressed in reference adult hepatocytes or cryopreserved hepatocytes used as internal control, were expressed at similar levels in the adult hepatocyte cluster of the reprogrammed cells.

Figure 10:
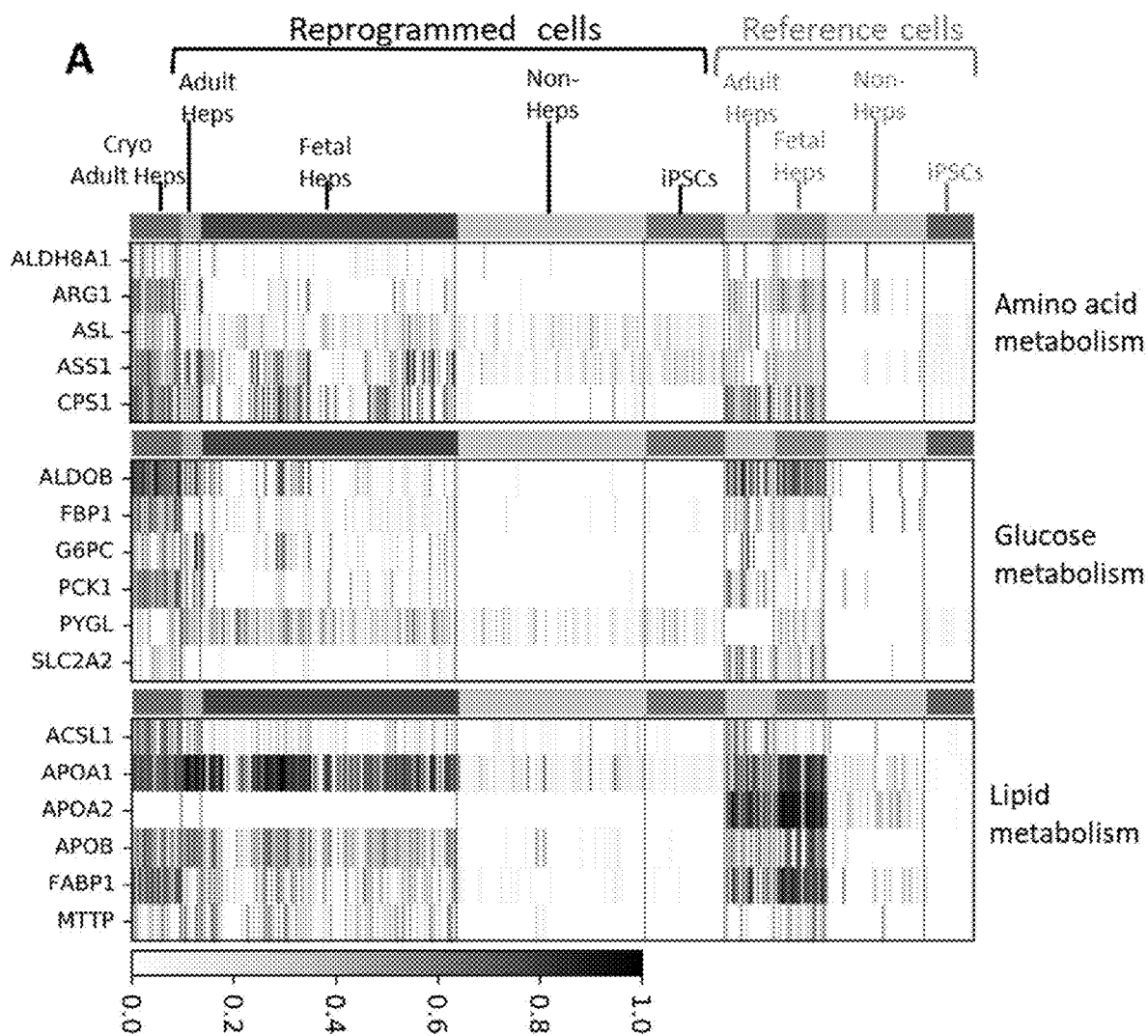
Figure 10:
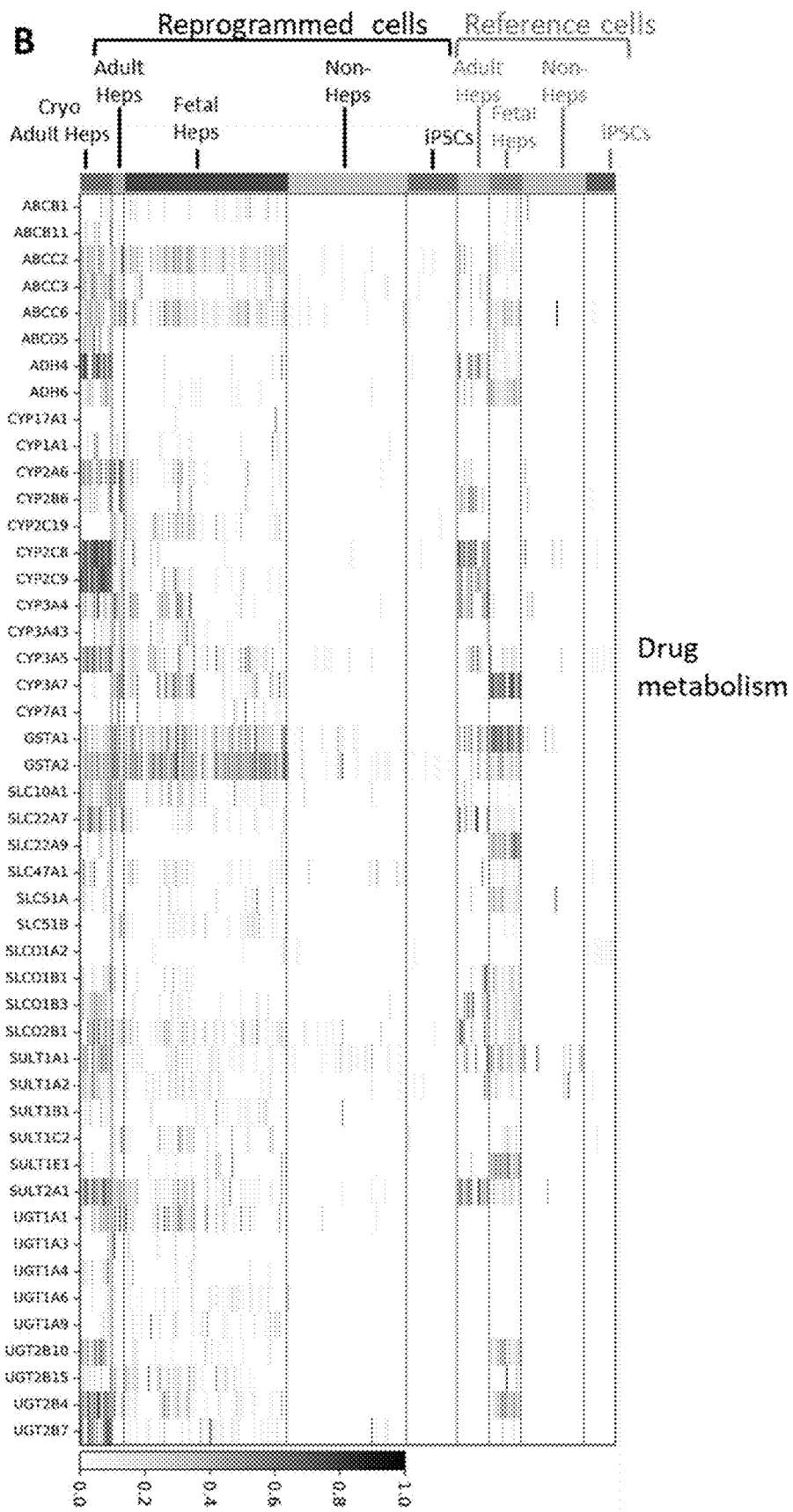

Hepatocytes in the liver can perform multiple functions including metabolism of drugs and toxins, regulation of synthesis, breakdown, storage and release of glucose and lipids, synthesis and storage of amino acids and vitamins. We compared the expression of the genes for specific hepatocyte-functions in reference and reprogrammed cells (FIG. 10). Reprogrammed cells from the adult hepatocyte cluster, exhibited a similar gene expression profile to reference and control hepatocytes both in expression levels and heterogeneity.

In order to assess the similarity of adult hepatocyte-like cells from the reprogrammed populations to reference hepatocytes in an unbiased and quantitative way, we used Pearson correlation analysis to score the different classes of cells after hierarchical clustering based on genome-wide gene expression. These results were plotted on a heatmap to show how well different clusters correlate with each other (FIG.

11). Supporting the classifier results, near-perfect correlation was observed between reference and control cryopreserved hepatocytes. Reprogrammed cells that are classified as adult hepatocytes clustered with the two adult cell populations based on the correlation matrix, demonstrating that their transcriptome is very closely related to adult hepatocytes.

Altogether, scRNA-seq analyses demonstrate that reprogrammed cultures contain cells that match primary adult hepatocyte identity with respect to the single cell genome-wide gene expression profiles, and exhibit several key gene expression signatures including those associated with hepatocyte specific metabolic pathways. Dissimilar expression that is observed in a minority of genes might reflect sampling of different hepatocyte subtypes isolated from liver and generated in vitro. Alternatively, it might indicate absence of optimal paracrine signaling or in vitro culture conditions which may be developed further. Gene expression profiles can be improved by culturing reprogrammed cells under optimized conditions developed for culturing primary hepatocytes (Swift et al., 2010; Xiang et al., 2019). Identification of TF Combinations that are Required for Hepatocyte Reprogramming The reprogrammed cells that align with adult hepatocytes express different numbers of unique exogenous reprogramming TFs (eTFs) per cell ranging from 1 to 16 (FIG. 12A). Single TFs showed differential expression across the reprogrammed populations (FIGS. 12B and C). Based on this and data from the literature on cellular reprogramming, we tested whether 4 transcription factors would be sufficient to reprogram cells to hepatocyte-like cells. To identify specific 4 TF combinations that might lead to reprogramming, we asked which unique 4 TF combinations out of all possible 4 TF combinations that can be generated from the set of 34 or 17 TFs are detected in the cells that align with each reference cell type. We ranked each TF combination based on the percentage of cells that express it within each cell type cluster and selected the combinations that are expressed in 20% or more of the cells in a given cluster. The combinations that were observed in the reprogrammed cells that cluster with adult hepatocytes in the 34 TF and 17 TF screens are comparable and are summarised in Table 5 (FIG. 12D). Analysis was performed in a similar manner for TF combinations containing 3 TFs and the combinations are summarised in Table 6 (FIG. 12E). We surmise that specific TF combinations shown in Table 5 and 6 alone, or with addition of other TFs, e.g., as shown herein can reprogram iPSCs to hepatocytes.
Validation of the Method of TF Combination Identification by Demonstration of Reprogramming Using the Combination CREB3L3-FOXA1-NR1I2-HHEX To test if our method described above can correctly identify TF combinations that can reprogram cells to hepatocyte-like cells, we tested one of the top 4 TF combinations identified—CREB3L3-FOXA1-NR1I2-HHEX—which includes the 4 of the most enriched single TFs that are found in the adult hepatocyte cluster from the reprogrammed cells.

On day 8, following transduction with a pool of lentiviral particles carrying these 4 TFs (4TF-LV), cells that express the ALB-RFP reporter emerged (FIG. 13A), showing that the cells acquired hepatic cell identity. By day 14, ALB+ colonies grew larger and a subset of these also expressed the CYP3A4-GFP reporter, indicating that these cells progressed to an adult hepatocyte-like state (FIG. 13A). Importantly, non-treated iPSCs did not induce any of the hepatic reporters. Some reporter-negative cells were also detectable in the 4TF-LV cultures, however this is likely due to not all of the 4 TFs being introduced into every single cell across the culture using a pool of lentiviral particles that carry single factors independently. We also observed some heterogeneous expression of the CYP3A4 reporter within ALB+ cell clusters, which might occur for one or more of the following reasons: (1) presence of CYP3A4-hepatocyte-like cells in the colonies, as in the adult liver, (2) some ALB+ cells might be missing one or more of the eTFs required for CYP3A4+ expression due to lack of genomic integration, or (3) silencing of the lentiviral transgene over the culture period.

We tested expression of specific proteins that are associated with hepatocyte functions, including CYP3A4, CYP1A2, CYP2D6 and CYP2C9 (Phase 1 drug metabolism), UGT1A1 (Phase II metabolism), ASGR1 (serum homeostasis) and PCK2 (glucose homeostasis) using specific antibodies (FIG. 13B). All the proteins were expressed in 4TF-LV cultures and showed a high level of overlap with ALB and CYP3A4 expression, demonstrating that the combination CREB3L3-FOXA1-NR1I2-HHEX can drive cells to a hepatocyte-like state with expression of multiple proteins involved in functionally independent pathways that operate in the hepatocytes of the adult liver.

To assess if the hepatocyte-like cells obtained by reprogramming can perform functions of adult hepatocytes, we subjected the cells to a CYP3A4-dependent drug metabolism assay, known as CYP3A4-GLO assay (Promega). For this, the cells were treated with a luminogenic substrate that is converted to a luciferin product by CYP3A4 and luminescence was measured as a readout (FIG. 13C). Huh7 and HepG2 hepatocarcinoma cells were used as positive control as these cells are established in vitro models to study drug metabolism and are commonly used to test cytochrome P450 activity (Bulutoglu et al., 2020). Cells reprogrammed with CREB3L3-FOXA1-NR1I2-HHEX from 3 independent iPSC lines (4TF-LV) exhibited functional levels that were multiple orders of magnitude over the control Huh7 and HepG2 cells. These results demonstrate that reprogrammed cells have established a functional drug metabolism pathway that involves uptake of a substrate/drug, oxidation through cytochrome P450 activity and export of by-products outside of the cells.
Complementary Activities of FOXA1, HHEX and NR1I2 are Used for Reprogramming Using CREB3L3-FOXA1-NR1I2-HHEX We aimed to determine if our method of TF combination identification can identify particular TF combinations for successful reprogramming. For this, we tested if reprogramming still occurs when a single TF is omitted from the combination CREB3L3-FOXA1-NR1I2-HHEX (FIG. 14). We found that omission of FOXA1 abolished progression of iPSCs to ALB+ hepatic cells on day 8 and ALB+/CYP3A4+ cells on day 14 of reprogramming, demonstrating that FOXA1 is used for the initial phase of reprogramming when cells acquire early hepatic identity, reflected by ALB expression. Upon exclusion of HHEX, no ALB+ cells were detected on day 8, however, ALB+ and ALB+/CYP3A4+ colonies emerged by day 14, albeit at numbers reduced compared to the 4TF combination. Interestingly, exclusion of NR1I2 did not affect progression of iPSCs to ALB+ cells, however, it abolished formation of ALB+/CYP3A4+ cells on day 14. Withdrawal of CREB3L3, however, did not lead to any discernible change in reprogramming based on expression of ALB and CYP3A4 reporters. Overall, these results demonstrate that FOXA1, HHEX and NR1I2 each perform unique functions during reprogramming and are each used in the context of reprogramming with CREB3L3-FOXA1-NR1I2-HHEX combination. Moreover, FOXA1-

NR1I2-HHEX is sufficient for reprogramming progression to ALB+/CYP3A4+ state, without the need of CREB3L3. However, it should be noted that since our readout was limited to expression of ALB and CYP3A4 reporters, we cannot currently exclude effects of CREB3L3 exclusion on other features of reprogrammed cells, such as the activity of functional pathways as CREB3L3 was shown to be involved in several metabolic processes in the adult liver (Khan & Margulies, 2019).

FOXA3 can Replace FOXA1 in Reprogramming to Hepatocyte-Like Cells

FOXA1 is a member of FOXA subfamily (also known as the HNF3 subfamily) of FOX transcription factors. The FOXA subfamily includes structurally related proteins, FOXA1, FOXA2 and FOXA3 (Golson and Kaestner, 2016). All 3 Proteins are expressed during liver development and their expression is maintained in the liver during adulthood. Several studies in mice have shown that these 3 FOXA factors can compensate for each other, including in the liver during embryonic development and adult life ((Iwafuchi-Doi et al., 2016; Kaestner et al., 1999; Lee et al., 2005; Shen et al., 2001)). FOXA3 is highly enriched in reprogrammed cells that cluster with adult hepatocytes (FIGS. 12B and C) and readily detected in the high frequency TF combinations (Table 5 and 6). We asked if FOXA3 when combined with CREB3L3, NR1I2 and HHEX can reprogram iPSCs to ALB+/CYP3A4+ hepatocyte-like cells. For this we reprogrammed iPSCs in parallel by overexpression of CREB3L3-FOXA1-NR1I2-HHEX or CREB3L3-FOXA3-NR1I2-HHEX (FIG. 15). Both cultures gave rise to similar numbers of ALB+/CYP3A4+ cells, demonstrating that FOXA3 might be interchangeable with FOXA1 during reprogramming to hepatocyte-like cells, consistent with the observation of FOXA3 in the TF combinations detected in reprogrammed cells that cluster with adult hepatocytes (Table 5 and 6).

NR1I3 can Replace NR1I2 in Reprogramming to Hepatocyte-Like Cells

NR1I2 and NR1I3 are functionally and structurally related TFs of the nuclear receptor family (Banerjee et al., 2015). We asked if reprogramming can be achieved when NR1I3 is combined with CREB3L3, FOXA1 and HHEX (FIG. 16). In cultures reprogrammed in parallel with CREB3L3-FOXA1-NR1I2-HHEX or CREB3L3-FOXA1-NR1I3-HHEX, ALB+/CYP3A4+ cells were detectable on day 13 at similar levels, demonstrating that a potential functional similarity might exist between NR1I2 and NR1I3 in the context of hepatocyte reprogramming.

Methods

Generation of Lentiviral Vectors Encoding the Reprogramming TFs and Transduction A single TF encoding sequence was cloned into a lentiviral vector (LV). Lentiviral vectors were generated and titrated by standard methods.

Generation of iPSC Lines Carrying Albumin and CYP3A4 Reporters

Reporter cell lines were generated using standard gene editing methods. Briefly, two knock-in homology directed repair (HDR) donor plasmids were constructed, one each for Albumin and CYP3A4, that inserted before the stop codon of the native genes a P2A peptide followed by a red or green fluorescent protein coding sequence (for Albumin or CYP3A4 respectively). These donor plasmids were introduced into iPSC lines at sites in the corresponding genetic loci using HDR. Clonal iPSC lines were isolated and shown to contain the desired knock in by genotyping PCR.

Cell Culture and Transduction of Lentiviral Vector

Induced pluripotent stem cells (iPSC) lines were routinely cultured in Essential 8 (E8) medium (ThermoFisher Scientific) on standard tissue culture plates coated with Vitronectin (Life Technologies). Cells were passaged every 3-6 days using 0.5 mM EDTA/Tris (Life Technologies) in clumps. The day before transduction (day −1), iPSCs were washed once with PBS and dissociated to single cells by treating with TrypLE (Life Technologies). Cells were counted and plated at a density of 12500 cells per cm2 in E8 (Supp) supplemented with 10 uM ROCK inhibitor, Y-27632. The next day (day 0), lentiviral vector (LV) pool consisting of all or a subset of 39 TFs was resuspended in culture media used by Ang and colleagues (Ang et al., 2018), with modifications, and supplemented with 10 ug/ml protamine sulphate (PS). E8 media was exchanged with media containing the LV. The next day (Day 1), the media was exchanged with fresh culture medium and refreshed every other day.

Fluorescence Microscopy and Immunofluorescence Staining

In order to detect Albumin-2A-RFP and CYP3A4-2A-GFP, cells were imaged using Revolve4 (Echo Labs). For immunofluorescence staining the following antibodies were used: CYP2C9 (Abcam, ab4236), CYP3A4 (Santa Cruz Biotechnology, sc53850), UGT1A1 (R&D Systems).

Cell Sorting and Single Cell RNA Sequencing (SC RNA-Seq)

For FACS, cultures were dissociated to single cells on day 11 post LV-transduction and resuspended in culture medium. Sorted cell populations were processed according to the standard protocol recommended by 10× Genomics.

REFERENCES

Aizarani et al. (2019). A human liver cell atlas reveals heterogeneity and epithelial progenitors. Nature 572 (7768):199-204

Ang et al. (2018). A Roadmap for Human Liver Differentiation from Pluripotent Stem Cells. Cell Reports 22(8): 2190-2205

Banerjee et al. (2015). Targeting xenobiotic receptors PXR and CAR in human diseases. In Drug Discovery Today (Vol. 20, Issue 5, pp. 618-628). Elsevier Ltd.

Becht et al. (2019). Dimensionality reduction for visualizing single-cell data using UMAP. Nature Biotechnology, 37(1), 38-47.

Bulutoglu et al. (2020). A comparison of hepato-cellular in vitro platforms to study CYP3A4 induction. PLOS ONE, 15(2), e0229106.

Cerbini et al. (2015) *PLOS One,* 10(1): e0116032

Golson and Kaestner, (2016) Fox transcription factors: From development to disease. Development (Cambridge), 143 (24), 4558-4570

Gossen et al. (1992) *Proc. Natl. Acad. Sci. U.S.A.* 89 (12): 5547-51 #

Hague et al. (2017). A practical guide to single-cell RNA-sequencing for biomedical research and clinical applications. In Genome Medicine (Vol. 9, Issue 1). BioMed Central Ltd.

Iwafuchi-Doi et al. (2016). The Pioneer Transcription Factor FoxA Maintains an Accessible Nucleosome Configuration at Enhancers for Tissue-Specific Gene Activation. Molecular Cell, 62(1), 79-91.

Iansante et al. (2018). Human hepatocyte transplantation for liver disease: current status and future perspectives. Pediatric Research 2018 83(1-2):232-240

Kaestner et al. (1999). Inactivation of the winged helix transcription factor HNF3a affects glucose homeostasis and islet glucagon gene expression in vivo. Genes and Development, 13(4), 495-504.

Khan & Margulies (2019). The role of mammalian Creb3-like transcription factors in response to nutrients. In Frontiers in Genetics (Vol. 10, Issue JUN, p. 591). Frontiers Media S.A.

Kietzmann, T. (2017). Metabolic zonation of the liver: The oxygen gradient revisited. In Redox Biology (Vol. 11, pp. 622-630). Elsevier B. V.

Lee et al. (2005). Foxa2 is required for the differentiation of pancreatic α-cells. Developmental Biology, 278(2), 484-495. MacParland et al. (2018). Single cell RNA sequencing of human liver reveals distinct intrahepatic macrophage populations. Nature Communications 9(1):4383

Nishikawa et al. (2015). Resetting the transcription factor network reverses terminal chronic hepatic failure. Journal of Clinical Investigation 125(4):1533-44

Papapetrou et al. (2011) *Nature Biotechnology*, 29(1): 73-8

Popescu et al. (2019). Decoding human fetal liver haematopoiesis. Nature, 574(7778), 365-371. Qian et al. (2012). In vivo reprogramming of murine cardiac fibroblasts into induced cardiomyocytes. Nature. 485(7400):593-8

Segal et al. (2019). Single cell analysis of human fetal liver captures the transcriptional profile of hepatobiliary hybrid progenitors. Nature Communications 10(1):3350

Selden et al. (2017) Scientific Reports 7: 14518

Shen et al. (2001). Foxa3 (Hepatocyte Nuclear Factor 3γ) is Required for the Regulation of Hepatic GLUT2 Expression and the Maintenance of Glucose Homeostasis during a Prolonged Fast. Journal of Biological Chemistry, 276 (46), 42812-42817.

Swift et al. (2010). Sandwich-cultured hepatocytes: An in vitro model to evaluate hepatobiliary transporter-based drug interactions and hepatotoxicity. In Drug Metabolism Reviews (Vol. 42, Issue 3, pp. 446-471). Informa Healthcare.

Wang et al. (1994) *Proc. Natl. Acad. Sci. USA* 91: 8180-8184

Williams D P. (2018). Application of hepatocyte-like cells to enhance hepatic safety risk assessment in drug discovery. Philosophical Transactions The Royal Society B Biological Sciences 373(1750)

Xiang et al. (2019). Long-term functional maintenance of primary human hepatocytes in vitro. Science, 364(6438), 399-402.

What is claimed is:

1. A cell comprising one or more exogenous expression cassettes encoding at least three or more transcription factors, wherein the at least three or more transcription factors comprise (1) FOXA1 or FOXA3; (2) HHEX; and (3) NR1I2 or NR1I3, and wherein the cell is a pluripotent stem cell comprising increased expression of the at least three or more transcription factors.

2. The cell of claim 1, wherein the at least three or more transcription factors are integrated into a genome of the cell.

3. The cell of claim 2, wherein the at least three or more transcription factors are integrated into a target site in the genome of the cell.

4. The cell of claim 1, wherein the increased expression is relative to an otherwise identical pluripotent stem cell but that lacks the one or more exogenous expression cassettes.

5. The cell of claim 1, wherein the at least three or more transcription factors further comprise GATA4.

6. The cell of claim 1, wherein the at least three or more transcription factors further comprise CREB3L3.

7. The cell of claim 1, wherein the at least three or more transcription factors comprise (1) FOXA1; (2) HHEX; and (3) NR1I2 or NR1I3.

8. The cell of claim 1, wherein the at least three or more transcription factors comprise (1) FOXA1 or FOXA3; (2) HHEX; and (3) NR1I2.

9. The cell of claim 1, wherein the cell further comprises one or more exogenous expression cassettes encoding one or more additional transcription factors.

10. The cell of claim 1, wherein the pluripotent stem cell is an induced pluripotent stem cell.

11. The cell of claim 1, wherein expression of the at least three or more transcription factors is under controlled transcription.

12. The cell of claim 1, wherein the at least three or more transcription factors comprise (1) FOXA1; (2) HHEX; and (3) NR1I2.

* * * * *